United States Patent
Boylan et al.

(10) Patent No.: US 10,619,160 B2
(45) Date of Patent: Apr. 14, 2020

(54) COMPOSITIONS AND METHODS FOR INHIBITING EXPRESSION OF RRM2 GENES

(71) Applicant: Arrowhead Pharmaceuticals, Inc., Pasadena, CA (US)

(72) Inventors: John Frederick Boylan, Bedminster, NJ (US); Birgit Bramlage, Meggen (CH); Markus Hossbach, Kulmbach (DE); John Reidhaar-Olson, New York, NY (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 15/906,054

(22) Filed: Feb. 27, 2018

(65) Prior Publication Data
US 2018/0195074 A1  Jul. 12, 2018

Related U.S. Application Data

(63) Continuation of application No. 15/415,415, filed on Jan. 25, 2017, now Pat. No. 9,938,531, which is a continuation of application No. 14/578,716, filed on Dec. 22, 2014, now abandoned, which is a continuation of application No. 13/275,377, filed on Oct. 18, 2011, now Pat. No. 8,946,176.

(30) Foreign Application Priority Data

Oct. 18, 2010  (EP) .................................... 10187851

(51) Int. Cl.
| | | |
|---|---|---|
| C12N 15/113 | (2010.01) | |
| A61K 48/00 | (2006.01) | |
| A61K 31/713 | (2006.01) | |
| C12N 9/02 | (2006.01) | |
| A01K 67/00 | (2006.01) | |

(52) U.S. Cl.
CPC .......... *C12N 15/1137* (2013.01); *A01K 67/00* (2013.01); *C12N 9/0093* (2013.01); *C12N 15/1135* (2013.01); *C12Y 117/04001* (2013.01); *A61K 48/00* (2013.01); *C12N 2310/14* (2013.01); *C12N 2310/315* (2013.01); *C12N 2310/321* (2013.01); *C12N 2310/33* (2013.01); *C12N 2310/335* (2013.01); *C12N 2310/346* (2013.01); *C12N 2310/351* (2013.01); *C12N 2310/50* (2013.01); *C12N 2310/53* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 5,023,243 A | 6/1991 | Tullis |
| 5,034,506 A | 7/1991 | Summerton et al. |
| 5,134,066 A | 7/1992 | Rogers et al. |
| 5,212,295 A | 5/1993 | Cook |
| 5,214,134 A | 5/1993 | Weis et al. |
| 5,216,141 A | 6/1993 | Benner |
| 5,218,105 A | 6/1993 | Cook et al. |
| 5,264,423 A | 11/1993 | Cohen et al. |
| 5,264,562 A | 11/1993 | Matteucci |
| 5,321,131 A | 6/1994 | Agrawal et al. |
| 5,328,470 A | 7/1994 | Nabel et al. |
| 5,359,044 A | 10/1994 | Cook et al. |
| 5,399,676 A | 3/1995 | Froehler |
| 5,405,939 A | 4/1995 | Suhadolnik et al. |
| 5,453,496 A | 9/1995 | Caruthers et al. |
| 5,455,233 A | 10/1995 | Spielvogel et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,489,677 A | 2/1996 | Sanghvi et al. |
| 5,506,351 A | 4/1996 | McGee |
| 5,519,134 A | 5/1996 | Acevedo et al. |
| 5,521,302 A | 5/1996 | Cook |
| 5,539,082 A | 7/1996 | Nielsen et al. |
| 5,541,307 A | 7/1996 | Cook et al. |
| 5,552,540 A | 9/1996 | Haralambidis |

(Continued)

FOREIGN PATENT DOCUMENTS

| | | |
|---|---|---|
| EP | 1752536 | 2/2007 |
| WO | 1991/006309 | 5/1991 |

(Continued)

OTHER PUBLICATIONS

Avolio TM et al. "RNA interference targeting the R2 subunit of ribonucleotide reductase inhibits growth of tumor cells in vitro and in vivo" Anti-Cancer Drugs 2007 vol. 18(4):377-388.

Reid G et al. "Potent subunit-specific effects on cell growth and drug sensitivity from optimised siRNA-mediated silencing of ribonucleotide reductase." Journal of RNAi and Gene Silencing, 2009 vol. 5(1): 321-330.

Duxbury MS et al. "Retrovirally mediated RNA interference targeting the M2 subunit of ribonucleotide reductase: A novel therapeutic strategy in pancreatic cancer" Surgury, 2004 vol. 136(2):261-269.

(Continued)

*Primary Examiner* — Tracy Vivlemore
(74) *Attorney, Agent, or Firm* — Robert M. Teigen; Paul Vander Velde

(57) ABSTRACT

The invention relates to a double-stranded ribonucleic acid (dsRNA) for inhibiting the expression of a RRM2 gene. The invention also relates to a pharmaceutical composition comprising the dsRNA or nucleic acid molecules or vectors encoding the same together with a pharmaceutically acceptable carrier; methods for treating diseases caused by the expression of a RRM2 gene using said pharmaceutical composition; and methods for inhibiting the expression of RRM2 in a cell.

21 Claims, 8 Drawing Sheets

Figure 1:
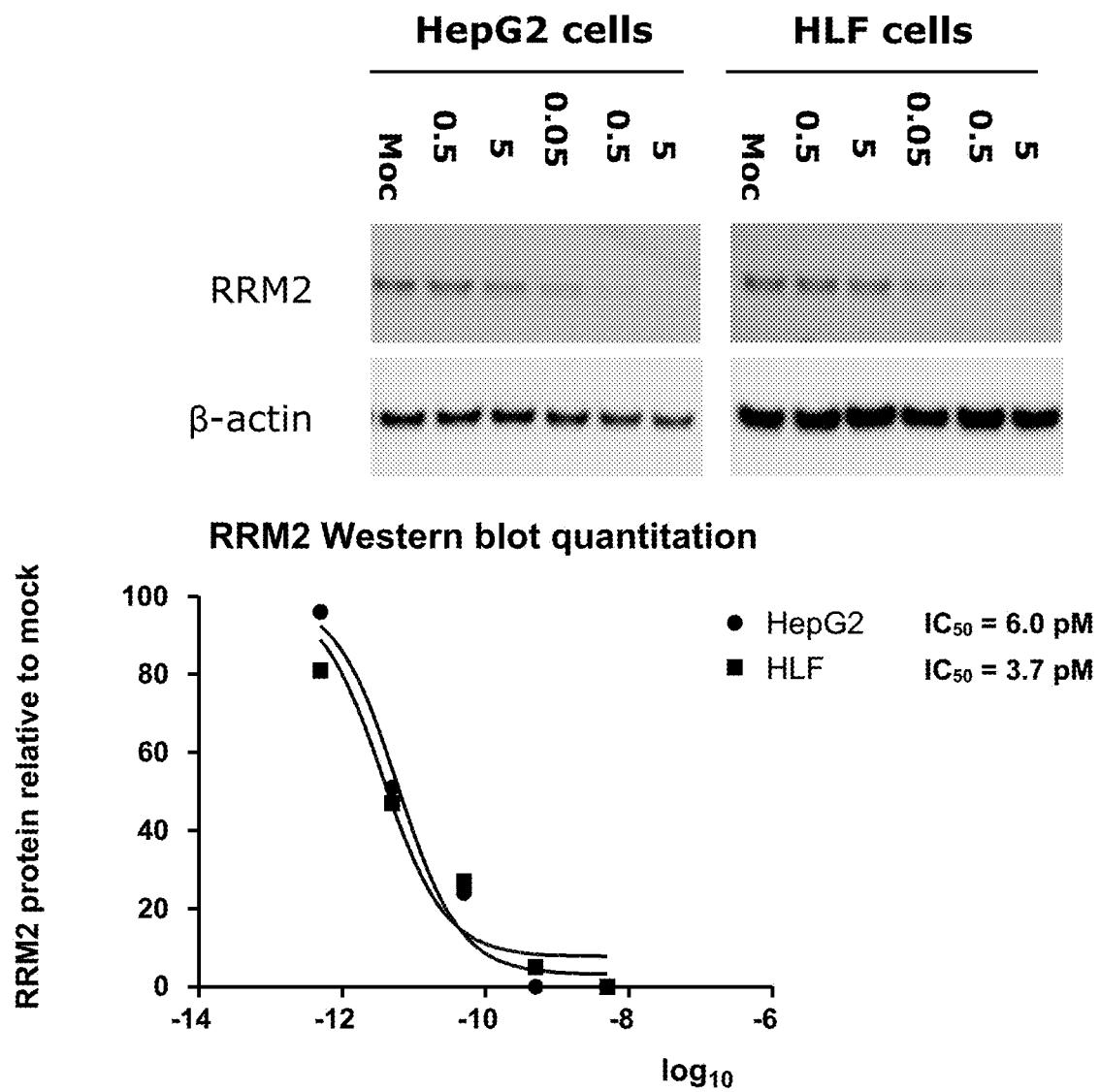

Specification includes a Sequence Listing.

(56) References Cited

U.S. PATENT DOCUMENTS

| | | | |
|---|---|---|---|
| 5,554,746 | A | 9/1996 | Ravikjumar et al. |
| 5,571,902 | A | 11/1996 | Ravikumar et al. |
| 5,578,718 | A | 11/1996 | Cook et al. |
| 5,581,469 | A | 12/1996 | Kim |
| 5,587,361 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,646,265 | A | 7/1997 | McGee |
| 5,663,312 | A | 9/1997 | Chaturvedula |
| 5,670,633 | A | 9/1997 | Cook et al. |
| 5,700,920 | A | 12/1997 | Altmann et al. |
| 6,127,533 | A | 10/2000 | Cook et al. |
| 6,166,197 | A | 12/2000 | Cook et al. |
| 6,172,209 | B1 | 1/2001 | Manoharan et al. |
| 6,262,241 | B1 | 7/2001 | Cook et al. |
| 6,271,358 | B1 | 8/2001 | Manoharan et al. |
| 2003/0050270 | A1 | 3/2003 | Monia et al. |
| 2008/0113351 | A1* | 5/2008 | Naito .................. A61K 31/713 435/6.11 |
| 2008/0227967 | A1 | 9/2008 | Khvorova et al. |

FOREIGN PATENT DOCUMENTS

| | | |
|---|---|---|
| WO | 1993/007883 | 4/1993 |
| WO | 2000/022113 | 4/2000 |
| WO | 2000/031105 | 6/2000 |
| WO | 2003/020931 | 3/2003 |
| WO | 2005/065719 A1 | 7/2005 |
| WO | 2006/017932 A1 | 2/2006 |
| WO | 2007/137220 | 11/2007 |
| WO | 2010/135322 | 11/2010 |

OTHER PUBLICATIONS

Heidel JD et al. "Potent siRNA inhibitors of ribonucleotide reductase subunit RRM2 reduce cell proliferation in vitro and in vivo." Clinical Cancer Research 2007, vol. 13(7):2207-2215.

Akhtar S et al., "Nonviral delivery of synthetic siRNAs in vivo," Journal of Clinical Investigation (2007) 117:3623-3632.

Atherton E et al., "The Fluorenylmethoxycarbonyl Amino Protecting Group" The Peptides, S. Udenfriend, J. Meienhofer, Eds., Academic Press, Inc. (1987) 9: 1-38.

Berkner KL et al., "Development of adenovirus vectors for the expression of heterologous genes," BioTechniques (1988) 6: 616-629.

Bucchini D et al., "Pancreatic expression of human insulin gene in transgenic mice," Proc. Natl. Acad. Sci. USA (1986) 83: 2511-2515.

Cook PD, "Medicinal Chemistry of Antisense Oligonucleotides—Future Opportunities." Anti-Cancer Drug Design (1991) 6: 585-607.

Chen S-H et al. "Gene therapy for brain tumors: Regression of experimental gliomas by adenovirus-mediated gene transfer in vivo," Proc. Natl. Acad. Sci. USA (1994) 91: 3054-3057.

Cone RD et al., "High-efficiency gene transfer into mammalian cells: Generation of helper-free recombinant retrovirus with broad mammalian host range," Proc. Natl. Acad. Sci. USA (1984) 81: 6349-6353.

Cornetta K et al., "Safety issues related to retroviral-mediated gene transfer in humans," Human Gene Therapy (1991) 2: 5-14.

Crooke et al., "Pharmacokinetic Properties of Several Novel Oligonucleotide Analogs in Mice." J. Pharmacal. Exp. Ther. (1996), 277: 923-927.

Danos O et al., "Safe and efficient generation of recombinant retroviruses with amphotropic and ecotropic host ranges," Proc. Natl. Acad. Sci. USA (1988) 85: 6460-6464.

Delgado C et al., "The Uses and Properties of PEG-Linked Proteins," Critical Reviews in Therapeutic Drug Carrier Systems (1992) 9(3,4): 249-304.

Docherty K et al., "Nutrient regulation of insulin gene expression," FASEB J. (1994) 8:20-24.

Englisch U et al., "Chemically Modified Oligonucleotides as Probes and Inhibitors," Angewandte Chemie, International Edition (1991) 30(6): 613-629.

Gassmann M et al., "Maintenance of an extrachromosomal plasmid vector in mouse embryonic stem cells," Proc. Natl. Acad. Sci. USA (1995) 92: 1292-1296.

Genbank NM_001034.3 (1987) and NM_001165931.1 (1987).

Greene et al. Protective Groups in Organic Synthesis, Chapter 2, 2d ed., John Wiley & Sons, New York, 1991, in Oligonucleotides and Analogues a Practical Approach, Ekstein, F. Ed., IRL Press, N.Y, 1991.

Guzaev AP et al., "A Conformationally Preorganized Universal Solid Support for Efficient Oligonucleotide Synthesis," J. Am. Chem. Soc. (2003) 125: 2380-2381.

Hamm ML et al., "Incorporation of 2'-Deoxy-2'-mercaptocytidine into Oligonucleotides via Phosphoramidite Chemistry," J. Org. Chem. (1997) 62: 3415-3420.

Hsu K-HL et al., "Immunogenicity of Recombinant Adenovirus-Respiratory Syncytial Virus Vaccines with Adenovirus Types 4, 5, and 7 Vectors in Dogs and a Chimpanzee," J. Infectious Disease, (1992) 166: 769-775.

Kabanov et al., "A new class of antivirals; antisense oligonucleotides combined with a hydrophobic substituent effectively inhibit influenza virus reproduction and synthesis of virus-specific proteins in MDCK cells," FEBS Lett. (1990) 259: 327-330.

Letsinger RL et al., "Cholesteryl-conjugated oligonucleotides: Synthesis, properties, and activity as inhibitors of replication of human immunodeficiency virus in cell culture," Proc. NatL Acad. Sci. USA (1989) 86: 6553-6556.

Li S et al., "Folate-Mediated Targeting of Antisense Oligodeoxynucleotides to Ovarian Cancer Cells," Pharmaceutical Research (1998) 15(10): 1540-1545.

Manoharan M et al., "Chemical Modifications to Improve Uptake and Bioavailability of Antisense Oligonucleotides," Ann. N.Y. Acad. Sci. (1992) 660: 306-309.

Manoharan M et al., "Introduction of a Lipophilic Thioether Tether in the Minor Groove of Nucleic Acids for Antisense Applications," Bioorg. & Med. Chem. Letters (1993) 3: 2765-2770.

Manoharan Met al., "Cholic Acid-Oligonucleotide Conjugates for Antisense Applications," Bioorg. Med. & Chem. Lett. (1994) 4: 1053-1060.

Manoharan M et al., "Oligonucleotide Conjugates: Alteration of the Pharmacokinetic Properties of Antisense Agents," Nucleosides & Nucleotides (1995) 14: 969-973.

Manoharan M et al., "Lipidic Nucleic Acids," Tetrahedron Letters (1995) 36: 3651-3654.

Manoharan M, "Oligonucleotide Conjugates as Potential Antisense Drugs with Improved Uptake, Biodistribution, Targeted Delivery, and Mechanism of Action," Antisense & Nucleic Acid Drug Devel. (2002) 12: 103-128.

Mishra RK et al., "Improved leishmanicidal effect of phosphorothioate antisense oligonucleotides by LDL-mediated delivery," Biochim. et Biophysica Acta (1995) 1264: 229-237.

Nawrot B et al., "Chemical and Structural Diversity of siRNA Molecules," Current Topics in Medicinal Chemistry (2006) 6: 913-925.

Nguyen T et al., "RNAi therapeutics: an update on delivery." Current Opinion in Molecular Therapeutics (2008) 10(2): 158-167.

Oberhauser et al., "Effective Incorporation of 2'-O-methyl-oligoribonucleotides Into Liposomes and Enhanced Cell Association Through Modification with Thiocholesterol," Nucl. Acids Research (1992) 20: 533-538.

Polushin NN et al., "Synthesis of Oligonucleotides Containing 2'-Azido- and 2'-Amino-2'-deoxyuridine Using Phosphotriester Chemistry," Tetrahedron Letters (1996) 37(19): 3227-3230.

Rosenfeld MA et al., "Adenovirus-mediated transfer of a recombinant alpha 1-antitrypsin gene to the lung epithelium in vivo," Science (1991) 252: 431-434.

(56) References Cited

OTHER PUBLICATIONS

Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.
Samukov VV et al., "2-(4-Nitrophenyl)sulfonylethoxycarbonyl (Nsc) Group as a Base-Labile α-Amino Protection for Solid Phase Peptide Synthesis," Tetrahedron Letters (1994) 35(42): 7821-7824.
Shea et al., "Synthesis, Hybridization Properties and Antiviral Activity of Lipid-oligodeoxynucleotide Conjugates," Nucl. Acids Research (1990) 18: 3777-3783.
Svinarchuk et al, "Inhibition of HIV proliferation in MT-4 cells by antisense oligonucleotide conjugated to lipophilic groups," Biochimie (1993) 75: 49-54.
Thomson JB et al., "Synthesis and Properties of Diuridine Phosphate Analogues Containing Thio and Amino Modifications," J. Org. Chem. (1996) 61: 6273-6281.
Wagner RW, "The state of the art in antisense research." Nature Medicine (1995) 1(11): 1116-1118.
Williams DJ et al., "Thermodynamic Comparison of the Salt Dependence of Natural RNA Hairpins and RNA Hairpins with Non-Nucleotide Spacers," Biochemistry (1996) 35: 14665-14670.
Zamboni, "Liposomal, Nanoparticle, and Conjugated Formulations of Anticancer Agents," Clin. Cancer Res. (2005) 11: 8230-8234.
Yun HJ et al., "Transcriptional targeting of gene expression in breast cancer by the promoters of protein regulator of cytokinesis 1 and ribonuclease reductase 2" Exper. Molec. Med. (2008) 40(3): 345-353.
Ikeda et al., "Ligand-Targeting Delivery of Therapeutic siRNA," Pharmaceutical Research (2006) 23: 1631-1640.
Rosenfeld MA et al., "In vivo transfer of the human cystic fibrosis transmembrane conductance regulator gene to the airway epithelium" Cell (1992) 68(1): 143-155.
Sanghvi, Antisense Research and Applications, (1993) Chapter 15, p. 289-301, Crooke ST and Lebleu B ed., CRC Press.
Kroschwitz JL, "Monomers," Encyclopedia of Polymer Science and Engineering, John Wiley & Sons, New York, pp. 715-727; (1990).
European Search Opinion for corresponding application EP14197970. (dated Jul. 20, 2015).
International Preliminary Report on Patentability for corresponding application PCT/EP2011/066718 dated Apr. 23, 2013.
Office Action for corresponding European Application 1497970.8 dated Aug. 18, 2016.

* cited by examiner

COMPOSITIONS AND METHODS FOR INHIBITING EXPRESSION OF RRM2 GENES

PRIORITY TO RELATED APPLICATION(S)

This application is a continuation of U.S. patent application Ser. No. 15/415,415, filed 25 Jan. 2017, which is a continuation of U.S. patent application Ser. No. 14/578,716, filed 22 Dec. 2014, now abandoned, which is a continuation of U.S. patent application Ser. No. 13/275,377, filed 18 Oct. 2011, now U.S. Pat. No. 8,946,176, which claims the benefit of European Patent Application No. 10187851.0, filed Oct. 18, 2010, all of which are hereby incorporated by reference in their entirety.

SEQUENCE LISTING

The present application is being filed along with a Sequence Listing, which is provided in electronic format. The Sequence Listing is provided as a file entitled 27028US4_SequenceListing.txt, created 26 Feb. 2018, and is approximately 294 KB in size. The Sequence Listing is hereby incorporated by reference in its entirety.

BACKGROUND OF THE INVENTION

Cancer remains an important area of high unmet medical need. The majority of current treatments provide small gains in overall survival requiring a delicate balance between efficacy and toxicity. Cancer is a disease characterized by uncontrolled growth and survival driven by improper regulation of the cell cycle. The cell cycle is divided up into four stages culminating in cytokinesis with checkpoint controls ensuring accurate completion of each phase. The cell cycle is designed to duplicate cellular material equally partitioning this material into what will become two new cells. DNA replication occurs during S-phase requiring pools of nucleic acid as the building blocks (dNTP) for new DNA as well as to repair DNA damage. Ribonucleotide reductase (RR) converts ribonucleoside 5'-diphosphates into 2'-deoxyribonucleotides which serve as the dNTP source for DNA synthesis and repair. RR catalyzes the rate-limiting step in the generation of dNTPs and represents an important part of cancer cell growth and repair. (RR) is made up of two subunits called RRM1 and RRM2 both of which are required for catalytic RR activity. RRM2 is overexpressed in a range of tumor types and elevated expression is associated with malignant transformation and metastasis. Overexpression of RRM2 cooperates with other oncogenes to drive the transformation and progression of normal cells. Tumor cells are particularly sensitive to changes in their dNTP pools because they have a high proliferation rate and lack checkpoint controls to monitor and repair DNA damage. Inhibition of RRM2 in tumor cells is expected to enhance DNA damage from a lack of sufficient dNTPs producing an apoptotic response. In nontransformed cells, checkpoint controls monitor the level of dNTPs and have the signaling ability to arrest cells before completing DNA replication and repair protecting cells from incurring incompletely replicated DNA or poorly repaired DNA damage.

Despite significant advances in the field of RNA interference (RNAi) and advances in the treatment of fibrosis and proliferative disorders, like cancers, there remains a need for an agent that can selectively and efficiently silence the RRM2 gene. A specific RRM2 inhibitor is expected to provide an improved therapeutic index over existing inhibitors because it is more selective and tumors cells lacking checkpoint controls are dependent on large dNTP pools to support their rapid proliferation and DNA repair. Also, preclinical data supports the potent tumor cell killing effects following RRM2 inhibition.

RRM2 mRNA overexpression is associated with rapidly proliferating tumor cells. RRM2 expression is cell cycle regulated peaking at S-phase when DNA replication and repair occur followed by rapid degradation during mitosis. RRM2 is overexpressed in Acute myeloid leukemia (AML), bladder cancer, prostate cancer, Non Small Cell Lung Cancer (NSCLC), breast cancer, Hepatocellular Carcinoma (HCC), and colorectal cancers to name a few.

Double-stranded ribonucleic acid (dsRNA) molecules have been shown to block gene expression in a highly conserved regulatory mechanism known as RNA interference (RNAi), which is a viable pathway in the development of therapeutically active substances for the treatment of a wide range of proliferating diseases. Accordingly, inhibition of RRM2 expression with the dsRNA molecules of this invention may be used in the treatment of cancer including but not limited to Hepatocellular Carcinoma (HCC) and leukemia as well as other solid tumor types.

SUMMARY OF THE INVENTION

The invention provides double-stranded ribonucleic acid molecules (dsRNAs), as well as compositions and methods for inhibiting the expression of the RRM2 gene, in particular the expression of the RRM2 gene, in a cell, tissue or mammal using such dsRNA. The invention also provides compositions and methods for treating pathological conditions and diseases caused by the expression of the RRM2 gene such as in proliferative disorders like cancer and inflammation.

In one preferred embodiment the described dsRNA molecule is capable of inhibiting the expression of a RRM2 gene by at least 60%, preferably by at least 70%, most preferably by at least 80%. The invention also provides compositions and methods for specifically targeting the liver with RRM2 dsRNA, for treating pathological conditions and diseases caused by the expression of the RRM2 gene including those described above.

DETAILED DESCRIPTION OF THE INVENTION

The invention provides double-stranded ribonucleic acid (dsRNA) molecules able to selectively and efficiently decrease the expression of RRM2. The use of RRM2 RNAi provides a method for the therapeutic and/or prophylactic treatment of diseases/disorders which are associated with inflammation and proliferative disorders, like cancers. Particular disease/disorder states include the therapeutic and/or prophylactic treatment of inflammation and proliferative disorders, like cancers, particularly HCC, leukemia and solid tumors, which method comprises administration of dsRNA targeting RRM2 to a human being or animal.

In one embodiment, the invention provides double-stranded ribonucleic acid (dsRNA) molecules for inhibiting the expression of a RRM2 gene, in particular the expression of the mammalian or human RRM2 gene. The dsRNA comprises at least two sequences that are complementary to each other. The dsRNA comprises a sense strand comprising a first sequence and an antisense strand comprising a second sequence, see sequences provided in the sequence listing and also the specific dsRNA pairs in the appended table 1 and table 2. In one embodiment the sense strand comprises a sequence which has an identity of at least 90% to at least a portion of an mRNA encoding RRM2. Said sequence is located in a region of complementarity of the sense strand to the antisense strand, preferably within nucleotides 2-7 of the 5' terminus of the antisense strand. In one preferred embodiment the dsRNA specifically targets the human RRM2 gene.

In one embodiment, the antisense strand comprises a nucleotide sequence which is substantially complementary to at least part of an mRNA encoding said RRM2 gene, and the region of complementarity is most preferably less than 30 nucleotides in length. Furthermore, it is preferred that the length of the herein described inventive dsRNA molecules (duplex length) is in the range of about 16 to 30 nucleotides, in particular in the range of about 18 to 28 nucleotides. Particularly useful in context of this invention are duplex lengths of about 19, 20, 21, 22, 23 or 24 nucleotides. Most preferred are duplex stretches of 19, 21 or 23 nucleotides. The dsRNA, upon delivery to a cell expressing a RRM2 gene, inhibits the expression of a RRM2 gene in vitro by at least 60%, preferably by at least 70%, and most preferably by 80%.

Appended Table 1 relates to preferred molecules to be used as dsRNA in accordance with this invention. Also modified dsRNA molecules are provided herein and are in particular disclosed in appended table 2, providing illustrative examples of modified dsRNA molecules of the present invention. As pointed out herein above, Table 2 provides for illustrative examples of modified dsRNAs of this invention (whereby the corresponding sense strand and antisense strand is provided in this table). The relation of the unmodified preferred molecules shown in Table 1 to the modified dsRNAs of Table 2 is illustrated in Table 5. Yet, the illustrative modifications of these constituents of the inventive dsRNAs are provided herein as examples of modifications.

Tables 3 and 4 provide for selective biological, clinical and pharmaceutical relevant parameters of certain dsRNA molecules of this invention.

Some of the preferred dsRNA molecules are provided in the appended table 1 and, inter alia and preferably, wherein the sense strand is selected from the group consisting of the nucleic acid sequences depicted in SEQ ID NOs: 8, 39, 56, 3, 82, 33, 9, 29, 444, 492 and 442 and the antisense strand is selected from the group consisting of the nucleic acid sequences depicted in SEQ ID NOs: 241, 272, 289, 236, 315, 266, 242, 262, 806, 852 and 851 Accordingly, the inventive dsRNA molecule may, inter alia, comprise the sequence pairs selected from the group consisting of SEQ ID NOs: 8/241, 39/272, 56/289, 3/236, 82/315, 33/266, 9/242, 29/262 444/806, 492/852 and 442/851. In the context of specific dsRNA molecules provided herein, pairs of SEQ ID NOs relate to corresponding sense and antisense strands sequences (5' to 3') as also shown in the tables.

In one embodiment the dsRNA molecules comprise an antisense strand with a 3' overhang of 1-5 nucleotides in length, preferably 1-2 nucleotides in length. Preferably said overhang of the antisense strand comprises uracil or nucleotides which are complementary to the mRNA encoding RRM2. In another preferred embodiment, said dsRNA molecules comprise a sense strand with a 3' overhang of 1-5 nucleotides in length, preferably 1-2 nucleotides in length. Preferably said overhang of the sense strand comprises uracil or nucleotides which are identical to the mRNA encoding RRM2.

In another preferred embodiment, the dsRNA molecules comprise a sense strand with a 3' overhang of 1-5 nucleotides in length, preferably 1-2 nucleotides in length, and an antisense strand with a 3' overhang of 1-5 nucleotides in length, preferably 1-2 nucleotides in length. Preferably said overhang of the sense strand comprises uracil or nucleotides which are at least 90% identical to the mRNA encoding RRM2 and said overhang of the antisense strand comprises uracil or nucleotides which are at least 90% complementary to the mRNA encoding RRM2.

The dsRNA molecules of the invention may be comprised of naturally occurring nucleotides or may be comprised of at least one modified nucleotide, such as a 2'-O-methyl modified nucleotide, inverted deoxythymidine, a nucleotide comprising a 5'-phosphorothioate group, and a terminal nucleotide linked to a cholesteryl derivative or dodecanoic acid bisdecylamide group. 2' modified nucleotides may have the additional advantage that certain immunostimulatory factors or cytokines are suppressed when the inventive dsRNA molecules are employed in vivo, for example in a medical setting. Alternatively and non-limiting, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In one preferred embodiment the dsRNA molecules comprises at least one of the following modified nucleotides: a 2'-O-methyl modified nucleotide, a nucleotide comprising a 5'-phosphorothioate group and a deoxythymidine. Preferred dsRNA molecules comprising modified nucleotides are given in table 2. In another preferred embodiment one of those deoxythymidine nucleotides at the 3' of both strand is a inverted deoxythymidine.

In a preferred embodiment the inventive dsRNA molecules comprise modified nucleotides as detailed in the sequences given in table 2. In one preferred embodiment the inventive dsRNA molecule comprises sequence pairs selected from the group consisting of SEQ ID NOs: 8/241, 39/272, 56/289, 3/236, 82/315, 33/266, 9/242, 29/262, 444/806, 492/852 and 442/851, and comprises overhangs at the antisense and/or sense strand of 1-2 deoxythymidines. In one preferred embodiment the inventive dsRNA molecule comprises sequence pairs selected from the group consisting of SEQ ID NOs: 8/241, 39/272, 56/289, 3/236, 82/315, 33/266, 9/242, 29/262 444/806, 492/852 and 442/851, and comprise modifications as detailed in table 2. Preferred dsRNA molecules comprising modified nucleotides are listed in table 2-4, with the most preferred dsRNA molecules depicted in SEQ ID Nos: 469/742, 475/884, 477/839, 497/711, 501/842, 553/968, 507/841, 525/885, 552/891, 477/963, 526/967 and 476/966.

In another embodiment, the inventive dsRNAs comprise modified nucleotides on positions different from those disclosed in table 2. In one preferred embodiment two deoxythymidine nucleotides are found at the 3' of both strands of the dsRNA molecule. Preferably said deoxythymidine nucleotides form an overhang.

In one embodiment the dsRNA molecules of the invention comprise a sense and an antisense strand wherein both strands have a half-life of at least 0.9 hours. In one preferred embodiment the dsRNA molecules of the invention comprise a sense and an antisense strand wherein both strands have a half-life of at least 48 hours, preferably in human serum. In another embodiment the dsRNA molecules of the invention are non-immunostimulatory, e.g. do not stimulate INF-alpha (INF-α) and TNF-alpha (TNF-α) in vitro. In another embodiment, the dsRNA molecules of the invention do stimulate INF-α and TNF-α in vitro to a very minor degree.

In another embodiment, a nucleic acid sequence encoding a sense strand and/or an antisense strand comprised in the dsRNAs as defined herein are provided.

The invention also provides for cells comprising at least one of the dsRNAs of the invention. The cell is preferably a mammalian cell, such as a human cell. Furthermore, tissues and/or non-human organisms comprising the herein defined dsRNA molecules are an embodiment of this invention, whereby said non-human organisms are particularly useful for research purposes or as research tools, for example in drug testing.

Furthermore, the invention relates to a method for inhibiting the expression of a RRM2 gene, in particular a mammalian or human RRM2 gene, in a cell, tissue or organism comprising the following steps:
 a) introducing into the cell, tissue or organism a double-stranded ribonucleic acid (dsRNA) as defined herein; and
 b) maintaining said cell, tissue or organism produced in step (a) for a time sufficient to obtain degradation of the mRNA transcript of a RRM2 gene, thereby inhibiting expression of a RRM2 gene in a given cell.

The invention also relates to pharmaceutical compositions comprising the inventive dsRNAs of the invention. These pharmaceutical compositions are particularly useful in the inhibition of the expression of a RRM2 gene in a cell, a tissue or an organism. The pharmaceutical composition comprising one or more of the dsRNA of the invention may also comprise (a) pharmaceutically acceptable carrier(s), diluent(s) and/or excipient(s).

In another embodiment, the invention provides methods for treating, preventing or managing inflammation and/or proliferative disorders like cancers which are associated with RRM2, said method comprising administering to a subject in need of such treatment, prevention or management a therapeutically or prophylactically effective amount of one or more of the dsRNAs of the invention. Preferably, said subject is a mammal, most preferably a human patient.

In one embodiment, the invention provides a method for treating a subject having a pathological condition mediated by the expression of a RRM2 gene. Such conditions comprise disorders associated with inflammation and proliferative disorders, like cancers, as described above. In this embodiment, the dsRNA acts as a therapeutic agent for controlling the expression of a RRM2 gene. The method comprises administering a pharmaceutical composition of the invention to the patient (e.g., human), such that expression of a RRM2 gene is silenced. Because of their high specificity, the dsRNAs of the invention specifically target mRNAs of a RRM2 gene. In one preferred embodiment the described dsRNAs specifically decrease RRM2 mRNA levels and do not directly affect the expression and/or mRNA levels of off-target genes in the cell.

In one preferred embodiment the described dsRNA decrease RRM2 mRNA levels in the liver by at least 60%, preferably by at least 70%, and most preferably by at least 80% in vivo. In another embodiment the described dsRNAs decrease RRM2 mRNA levels in vivo for at least 4 days. In another preferred embodiment, the dsRNAs of the invention are used for the preparation of a pharmaceutical composition for the treatment of inflammation and proliferative disorders, like cancer. Cancers to be treated with said pharmaceutical composition comprise but are not limited to: HCC, AML, leukemia, bladder cancer, prostate cancer, NSCLC, breast cancer and colorectal cancer.

In another embodiment, the invention provides vectors for inhibiting the expression of a RRM2 gene in a cell, in particular a RRM2 gene comprising a regulatory sequence operably linked to a nucleotide sequence that encodes at least one strand of the dsRNA molecules of the invention.

In another embodiment, the invention provides a cell comprising a vector for inhibiting the expression of a RRM2 gene in a cell. Said vector comprises a regulatory sequence operably linked to a nucleotide sequence that encodes at least one strand of the dsRNA molecule of the invention. Yet, it is preferred that said vector comprises, besides said regulatory sequence a sequence that encodes at least one "sense strand" of the inventive dsRNA and at least one "anti-sense strand" of said dsRNA. It is also envisaged that the claimed cell comprises two or more vectors comprising, besides said regulatory sequences, the herein defined sequence(s) that encode(s) at least one strand of the dsRNA molecules of the invention.

In one embodiment, the method comprises administering a composition comprising a dsRNA, wherein the dsRNA comprises a nucleotide sequence which is complementary to at least a part of an RNA transcript of a RRM2 gene of the mammal to be treated. As pointed out above, also vectors and cells comprising nucleic acid molecules that encode for at least one strand of the herein defined dsRNA molecules can be used as pharmaceutical compositions and may, therefore, also be employed in the herein disclosed methods of treating a subject in need of medical intervention. It is also of note that these embodiments relating to pharmaceutical compositions and to corresponding methods of treating a (human) subject also relate to approaches like gene therapy approaches. RRM2 specific dsRNA molecules as provided herein or nucleic acid molecules encoding individual strands of these inventive dsRNA molecules may also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In another aspect of the invention, RRM2 specific dsRNA molecules that modulate RRM2 gene expression activity are expressed from transcription units inserted into DNA or RNA vectors (see, e.g., Skillern, A., et al., International PCT Publication No. WO 00/22113). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively, each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka, et al., *Curr. Topics Micro. Immunol.* (1992) 158:97-129)); adenovirus (see, for example, Berkner, et al., *BioTechniques* (1998) 6:616), Rosenfeld et al. (1991, *Science* 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Danos and Mulligan, *Proc. Natl. Acad. Sci. USA* (1998) 85:6460-6464). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, *Human Gene Therapy* 2:5-10; Cone et al., 1984, *Proc. Natl. Acad. Sci. USA* 81:6349). Recombinant adenoviral vectors can be used to infect a wide variety of cells and tissues in susceptible hosts (e.g., rat, hamster, dog, and chimpanzee) (Hsu et al., 1992, *J. Infectious Disease*, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, *Proc. Natl. Acad. Sci. USA* 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, *FASEB J.* 8:20-24). Such inducible expression systems, suitable for the control of transgene expression in cells or in mammals include regulation by ecdysone, by estrogen, progesterone, tetracycline, chemical inducers of dimerization, and isopropyl-β-D1-thiogalactopyranoside (EPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single RRM2 gene or multiple RRM2 genes over a period of a week or more are also contemplated by the invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The following detailed description discloses how to make and use the dsRNA and compositions containing dsRNA to inhibit the expression of a target RRM2 gene, as well as compositions and methods for treating diseases and disorders caused by the expression of said RRM2 gene.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G", "C", "A", "U", and "T" or "dT" respectively, each generally stand for a nucleotide that contains guanine, cytosine, adenine, uracil and deoxythymidine as a base, respectively. However, the term "ribonucleotide" or "nucleotide" can also refer to a modified nucleotide, as further detailed below, or a surrogate replacement moiety. Sequences comprising such replacement moieties are embodiments of the invention. As detailed below, the herein described dsRNA molecules may also comprise "overhangs", i.e. unpaired, overhanging nucleotides which are not directly involved in the RNA double helical structure normally formed by the herein defined pair of "sense strand" and "anti-sense strand". Often, such an overhanging stretch comprises the deoxythymidine nucleotide, in most embodiments, 2 deoxythymidines in the 3' end. Such overhangs will be described and illustrated below.

The term "RRM2" as used herein relates in particular to the ribonucleotide reductase M2, also known as the ribonucleotide reductase M2 polypeptide, ribonucleoside-diphosphate reductase subunit M2, ribonucleotide reductase small chain, ribonucleotide reductase small subunit, with synonyms R2, RR2, RR2M, and the like and said term relates to the corresponding gene, encoded mRNA, encoded protein/polypeptide as well as functional fragments of the same. Preferred is the human RRM2 gene. In other preferred embodiments the dsRNAs of the invention target the RRM2 gene of human (*H. sapiens*) and cynomolgous monkey (*Macaca fascicularis*) RRM2 gene. Also dsRNAs targeting the rat (*Rattus norvegicus*) and mouse (*Mus musculus*) RRM2 gene are part of this invention. The term "RRM2 gene/sequence" does not only relate to (the) wild-type sequence(s) but also to mutations and alterations which may be comprised in said gene/sequence. Accordingly, the present invention is not limited to the specific dsRNA molecules provided herein. The invention also relates to dsRNA molecules that comprise an antisense strand that is at least 85% complementary to the corresponding nucleotide stretch of an RNA transcript of a RRM2 gene that comprises such mutations/alterations.

As used herein, "target sequence" refers to a contiguous portion of the nucleotide sequence of an mRNA molecule formed during the transcription of a RRM2 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature. However, as detailed herein, such a "strand comprising a sequence" may also comprise modifications, like modified nucleotides.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence. "Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

Sequences referred to as "fully complementary" comprise base-pairing of the oligonucleotide or polynucleotide comprising the first nucleotide sequence to the oligonucleotide or polynucleotide comprising the second nucleotide sequence over the entire length of the first and second nucleotide sequence.

However, where a first sequence is referred to as "substantially complementary" with respect to a second sequence herein, the two sequences can be fully complementary, or they may form one or more, but preferably not more than 13 mismatched base pairs upon hybridization.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

The term "double-stranded RNA", "dsRNA molecule", or "dsRNA", as used herein, refers to a ribonucleic acid molecule, or complex of ribonucleic acid molecules, having a duplex structure comprising two anti-parallel and substantially complementary nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. In addition to the duplex structure, a dsRNA may comprise one or more nucleotide overhangs. The nucleotides in said "overhangs" may comprise between 0 and 5 nucleotides, whereby "0" means no additional nucleotide(s) that form(s) an "overhang" and whereas "5" means five additional nucleotides on the individual strands of the dsRNA duplex. These optional "overhangs" are located in the 3' end of the individual strands. As will be detailed below, also dsRNA molecules which comprise only an "overhang" in one of the two strands may be useful and even advantageous in context of this invention. The "overhang" comprises preferably between 0 and 2 nucleotides. Most preferably 2 "dT" (deoxythymidine) nucleotides are found at the 3' end of both strands of the dsRNA. Also 2 "U" (uracil) nucleotides can be used as overhangs at the 3' end of both strands of the dsRNA. Accordingly, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. For example the antisense strand comprises 23 nucleotides and the sense strand comprises 21 nucleotides, forming a 2 nucleotide overhang at the 3' end of the antisense strand. Preferably, the 2 nucleotide overhang is fully complementary to the mRNA of the target gene. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence. Where the region of complementarity is not fully complementary to the target sequence, the mismatches are most tolerated outside nucleotides 2-7 of the 5' terminus of the antisense strand The term "sense strand," as used herein, refers to the strand of a dsRNA that includes a region that is substantially complementary to a region of the antisense strand. "Substantially complementary" means preferably at least 85% of the overlapping nucleotides in sense and antisense strand are complementary.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. It is, for example envisaged that the dsRNA molecules of this invention be administered to a subject in need of medical intervention. Such an administration may comprise the injection of the dsRNA, the vector or a cell of this invention into a diseased site in said subject, for example into liver tissue/cells or into cancerous tissues/cells, like liver cancer tissue. In addition, the injection is preferably in close proximity to the diseased tissue envisaged. In vitro introduction into a cell includes methods known in the art such as electroporation and lipofection.

As used herein, "proliferating" and "proliferation" refer to cells undergoing mitosis. Throughout this application, the term "proliferative disorder" refers to any disease/disorder marked by unwanted or aberrant proliferation of tissue. As used herein, the term "proliferative disorder" also refers to conditions in which the unregulated and/or abnormal growth of cells can lead to the development of an unwanted condition or disease, which can be cancerous or non-cancerous.

The term "inflammation" as used herein refers to the biologic response of body tissue to injury, irritation, or disease which can be caused by harmful stimuli, for example, pathogens, damaged cells, or irritants. Inflammation is typically characterized by pain and swelling. Inflammation is intended to encompass both acute responses, in which inflammatory processes are active (e.g., neutrophils and leukocytes), and chronic responses, which are marked by slow progress, a shift in the type of cell present at the site of inflammation, and the formation of connective tissue.

Cancers to be treated comprise, but are again not limited to leukemia, AML, solid tumors, liver cancer, brain cancer, breast cancer, lung cancer, NSCLC, colorectal cancer, bladder cancer and prostate cancer, whereby said liver cancer may, inter alia, be selected from the group consisting of hepatocellular carcinoma (HCC), hepatoblastoma, a mixed liver cancer, a cancer derived from mesenchymal tissue, a liver sarcoma or a cholangiocarcinoma.

The terms "silence", "inhibit the expression of" and "knock down", in as far as they refer to a RRM2 gene, herein refer to the at least partial suppression of the expression of a RRM2 gene, as manifested by a reduction of the amount of mRNA transcribed from a RRM2 gene which may be isolated from a first cell or group of cells in which a RRM2 gene is transcribed and which has or have been treated such that the expression of a RRM2 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to the RRM2 gene transcription, e.g. the amount of protein encoded by a RRM2 gene which is secreted by a cell, or the number of cells displaying a certain phenotype.

As illustrated in the appended examples and in the appended tables provided herein, the inventive dsRNA molecules are capable of inhibiting the expression of a human RRM2 by at least about 60%, preferably by at least 70%, most preferably by at least 80% in vitro assays, i.e. in vitro. The term "in vitro" as used herein includes but is not limited to cell culture assays. In another embodiment the inventive dsRNA molecules are capable of inhibiting the expression of a mouse or rat RRM2 by at least 60%. preferably by at least 70%, most preferably by at least 80%. The person skilled in the art can readily determine such an inhibition rate and related effects, in particular in light of the assays provided herein.

The term "off target" as used herein refers to all non-target mRNAs of the transcriptome that are predicted by in silico methods to hybridize to the described dsRNAs based on sequence complementarity. The dsRNAs of the present invention preferably do specifically inhibit the expression of RRM2, i.e. do not inhibit the expression of any off-target.

The term "half-life" as used herein is a measure of stability of a compound or molecule and can be assessed by methods known to a person skilled in the art, especially in light of the assays provided herein.

The term "non-immunostimulatory" as used herein refers to the absence of any induction of a immune response by the invented dsRNA molecules. Methods to determine immune responses are well known to a person skilled in the art, for example by assessing the release of cytokines, as described in the examples section.

The terms "treat", "treatment", and the like, mean in context of this invention the relief from or alleviation of a disorder related to RRM2 expression, like inflammation and proliferative disorders, like cancers.

As used herein, a "pharmaceutical composition" comprises a pharmacologically effective amount of a dsRNA and a pharmaceutically acceptable carrier. However, such a "pharmaceutical composition" may also comprise individual strands of such a dsRNA molecule or the herein described vector(s) comprising a regulatory sequence operably linked to a nucleotide sequence that encodes at least one strand of a sense or an antisense strand comprised in the dsRNAs of this invention. It is also envisaged that cells, tissues or isolated organs that express or comprise the herein defined dsRNAs may be used as "pharmaceutical compositions". As used herein, "pharmacologically effective amount," "therapeutically effective amount" or simply "effective amount" refers to that amount of an RNA effective to produce the intended pharmacological, therapeutic or preventive result.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives as known to persons skilled in the art.

It is in particular envisaged that the pharmaceutically acceptable carrier allows for the systemic administration of the dsRNAs, vectors or cells of this invention. Whereas also the enteric administration is envisaged the parenteral administration and also transdermal or transmucosal (e.g. insufflation, buccal, vaginal, anal) administration as well as inhalation of the drug are feasible ways of administering to a patient in need of medical intervention the compounds of this invention. When parenteral administration is employed, this can comprise the direct injection of the compounds of this invention into the diseased tissue or at least in close proximity. However, also intravenous, intraarterial, subcutaneous, intramuscular, intraperitoneal, intradermal, intrathecal and other administrations of the compounds of this invention are within the skill of the artisan, for example the attending physician.

For intramuscular, subcutaneous and intravenous use, the pharmaceutical compositions of the invention will generally be provided in sterile aqueous solutions or suspensions, buffered to an appropriate pH and isotonicity. In a preferred embodiment, the carrier consists exclusively of an aqueous buffer. In this context, "exclusively" means no auxiliary agents or encapsulating substances are present which might affect or mediate uptake of dsRNA in the cells that express a RRM2 gene. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in PCT publication WO 91/06309 which is incorporated by reference herein.

As used herein, a "transformed cell" is a cell into which at least one vector has been introduced from which a dsRNA molecule or at least one strand of such a dsRNA molecule may be expressed. Such a vector is preferably a vector comprising a regulatory sequence operably linked to nucleotide sequence that encodes at least one sense strand or antisense strand of a dsRNA of the present invention.

It can be reasonably expected that shorter dsRNAs comprising one of the sequences in Table 1 and 4 minus only a few nucleotides on one or both ends may be similarly effective as compared to the dsRNAs described above.

In one preferred embodiment the inventive dsRNA molecules comprise nucleotides 1-19 of the sequences given in Table 1.

As pointed out above, in most embodiments of this invention, the dsRNA molecules provided herein comprise a duplex length (i.e. without "overhangs") of about 16 to about 30 nucleotides. Particular useful dsRNA duplex lengths are about 19 to about 25 nucleotides. Most preferred are duplex structures with a length of 19 nucleotides. In the inventive dsRNA molecules, the antisense strand is at least partially complementary to the sense strand.

The dsRNA of the invention can contain one or more mismatches to the target sequence. In a preferred embodiment, the dsRNA of the invention contains no more than 13 mismatches. If the antisense strand of the dsRNA contains mismatches to a target sequence, it is preferable that the area of mismatch not be located within nucleotides 2-7 of the 5' terminus of the antisense strand. In another embodiment it is preferable that the area of mismatch not be located within nucleotides 2-9 of the 5' terminus of the antisense strand.

As mentioned above, at least one end/strand of the dsRNA may have a single-stranded nucleotide overhang of 1 to 5, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

The dsRNA of the present invention may also be chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages, inverted deoxythymidines. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds.

In certain embodiments, a chemical bond may be formed by means of one or several bonding groups, wherein such bonding groups are preferably poly-(oxyphosphinicooxy-1,3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, for example certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Introduction of a locked nucleotide into an oligonucleotide improves the affinity for complementary sequences and increases the melting temperature by several degrees.

Modifications of dsRNA molecules provided herein may positively influence their stability in vivo as well as in vitro and also improve their delivery to the (diseased) target side. Furthermore, such structural and chemical modifications may positively influence physiological reactions towards the dsRNA molecules upon administration, e.g. the cytokine release which is preferably suppressed. Such chemical and structural modifications are known in the art and are, inter alia, illustrated in Nawrot (2006) *Current Topics in Med Chem*, 6, 913-925.

Conjugating a ligand to a dsRNA can enhance its cellular absorption as well as targeting to a particular tissue. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Attachment of folic acid to the 3'-terminus of an oligonucleotide results in increased cellular uptake of the oligonucleotide (Li, S.; Deshmukh, H. M.; Huang, L. *Pharm. Res.* 1998, 15, 1540). Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. No. 5,218,105, drawn to polyamine conjugated oligonucleotides; U.S. Pat. No. 5,541,307, drawn to oligonucleotides having modified backbones; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. No. 5,587,361 drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,608,046, both drawn to conjugated 4'-desmethyl nucleoside analogs; U.S. Pat. No. 5,610,289, drawn to backbone-modified oligonucleotide analogs; U.S. Pat. No. 6,262,241 drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to commercially available phosphoramidites.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters.

The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p.1) and various substituted sulfonylethyl carbamates exemplified by the Nsc group (Samukov et al., *Tetrahedron Lett.*, 1994, 35:7821.

Additional amino-protecting groups include, but are not limited to, carbamate protecting groups, such as 2-trimethylsilylethoxycarbonyl (Teoc), 1-methyl-1-(4-biphenylyl)-ethoxycarbonyl (Bpoc), t-butoxycarbonyl (BOC), allyloxycarbonyl (Alloc), 9-fluorenyl-methyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support allows for the preparation of oligonucleotides having unusual or modified nucleotides located at the 3'-terminus of the oligonucleotide. For further details about universal supports see Scott et al., *Innovations and Perspectives in solid-phase Synthesis*, 3rd International Symposium, 1994, Ed. Roger Epton, Mayflower Worldwide, 115-124]. In addition, it has been reported that the oligonucleotide can be cleaved from the universal support under milder reaction conditions when the oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States Patents relating to the preparation of the above phosphorus-atom-containing linkages include, but are not limited to, U.S. Pat. Nos. 4,469,863; 5,023,243; 5,264,423; 5,321,131; 5,399,676; 5,405,939; 5,453,496; 5,455,233 and 5,466,677, each of which is herein incorporated by reference in their entirety.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,214,134; 5,216,141; 5,264,562; 5,466,677; 5,470,967; 5,489,677; 5,602,240 and 5,663,312, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Teaching of PNA compounds can be found for example in U.S. Pat. No. 5,539,082.

Some preferred embodiments of the invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 5,134,066; 5,459,255; 5,552,540; 5,594,121 and 5,596,091 all of which are hereby incorporated by reference.

In certain embodiments, the oligonucleotides employed in the ligand-conjugated oligonucleotides of the invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O—$CH_2CH_2OCH_3$, also known as 2'-O-(2-methoxyethyl) or 2'-MOE], i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula $(O-alkyl)_m$, wherein m is 1 to about 10. Preferred among these polyethers are linear and cyclic polyethylene glycols (PEGs), and (PEG)-containing groups, such as crown ethers and, inter alia, those which are disclosed by Delgardo et. al. (*Critical Reviews in Therapeutic Drug Carrier Systems* 1992, 9:249), which is hereby incorporated by reference in its entirety. Further sugar modifications are disclosed by Cook (*Anti-fibrosis Drug Design*, 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the invention include 2'-SR and 2'-NR$_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, 1997, 62:3415-3420). 2'-NR nucleosides are disclosed by Goettingen, M., *J. Org. Chem.*, 1996, 61, 6273-6281; and Polushin et al., *Tetrahedron Lett.*, 1996, 37, 3227-3230. Further representative 2'-substituent groups amenable to the invention include those having one of formula I or II:

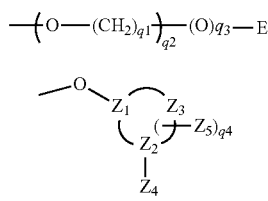

wherein,

E is $C_1$-$C_{10}$ alkyl, $N(Q_3)(Q_4)$ or $N=C(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;
$q_2$ is an integer from 1 to 10;
$q_3$ is 0 or 1;
$q_4$ is 0, 1 or 2;
each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

$Z_4$ is $OM_1$, $SM_1$, or $N(M_1)_2$; each $M_1$ is, independently, H, $C_1$-$C_8$ alkyl, $C_1$-$C_8$ haloalkyl, $C(=NH)N(H)M_2$, $C(=O)N(H)M_2$ or $OC(=O)N(H)M_2$; $M_2$ is H or $C_1$-$C_8$ alkyl; and $Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the invention. Representative substitutions for ring O include, but are not limited to, S, $CH_2$, CHF, and $CF_2$.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 5,359,044; 5,466,786; 5,519,134; 5,591,722; 5,597,909; 5,646,265 and 5,700,920, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO* 1, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

The invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO* 1, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphorylated.

Importantly, each of these approaches may be used for the synthesis of ligand conjugated oligonucleotides. Amino linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

The person skilled in the art is readily aware of methods to introduce the molecules of this invention into cells, tissues or organisms. Corresponding examples have also been provided in the detailed description of the invention above. For example, the nucleic acid molecules or the vectors of this invention, encoding for at least one strand of the inventive dsRNAs may be introduced into cells or tissues by methods known in the art, like transfections etc.

Also for the introduction of dsRNA molecules, means and methods have been provided. For example, targeted delivery by glycosylated and folate-modified molecules, including the use of polymeric carriers with ligands, such as galactose and lactose or the attachment of folic acid to various macromolecules allows the binding of molecules to be delivered to folate receptors. Targeted delivery by peptides and proteins other than antibodies, for example, including RGD-modified nanoparticles to deliver siRNA in vivo or multicomponent (nonviral) delivery systems including short cyclodextrins, adamantine-PEG are known. Yet, also the targeted delivery using antibodies or antibody fragments, including (monovalent) Fab-fragments of an antibody (or other fragments of such an antibody) or single-chain antibodies are envisaged. Injection approaches for target directed delivery comprise, inter alia, hydrodynamic i.v. injection. Also cholesterol conjugates of dsRNA may be used for targeted delivery, whereby the conjugation to lipohilic groups enhances cell uptake and improve pharmacokinetics and tissue biodistribution of oligonucleotides. Also cationic delivery systems are known, whereby synthetic vectors with net positive (cationic) charge to facilitate the complex formation with the polyanionic nucleic acid and interaction with the negatively charged cell membrane. Such cationic delivery systems comprise also cationic liposomal delivery systems, cationic polymer and peptide delivery systems. Other delivery systems for the cellular uptake of dsRNA/siRNA are aptamer-ds/siRNA. Also gene therapy approaches can be used to deliver the inventive dsRNA molecules or nucleic acid molecules encoding the same. Such systems comprise the use of non-pathogenic virus, modified viral vectors, as well as deliveries with nanoparticles or liposomes. Other delivery methods for the cellular uptake of dsRNA are extracorporeal, for example ex vivo treatments of cells, organs or tissues. Certain of these technologies are described and summarized in publications, like Akhtar (2007), *Journal of Clinical Investigation* 117, 3623-3632, Nguyen et al. (2008), *Current Opinion in Moleculare Therapeutics* 10, 158-167, Zamboni (2005), *Clin. Cancer Res.* 11, 8230-8234 or Ikeda et al. (2006), *Pharmaceutical Research* 23, 1631-1640

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The above provided embodiments and items of the present invention are now illustrated with the following, non-limiting examples.

DESCRIPTION OF FIGURES AND APPENDED TABLES

Table 1. Core sequences of dsRNAs targeting human RRM2 gene Letters in capitals represent RNA nucleotides.

Table 2. Characterization of dsRNAs targeting human RRM2: Activity testing with single dose in HeLa-S3 cells. Letters in capitals represent RNA nucleotides, lower case letters "c", "g", "a" and "u" represent 2'-O-methyl-modified nucleotides, "s" represents phosphorothioate, "dT" deoxythymidine, and "p" represents 5'-phosphate group (sequences without a "p" are lacking a 5'-phosphate group). S.d.=standard deviation, % mRNA=mean mRNA knockdown.

Table 3. Characterization of dsRNAs targeting human RRM2: Activity testing for dose response in HeLa-S3 cells. IC 50: 50% inhibitory concentration, IC 80: 80% inhibitory concentration, IC 20: 20% inhibitory concentration.

Table 4. Characterization of dsRNAs targeting human RRM2: Stability and Cytokine Induction. t ½: half-life of a strand as defined in examples, PBMC: Human peripheral blood mononuclear cells.

Table 5. Core sequences of dsRNAs targeting human RRM2 gene and their modified counterparts. Letters in capitals represent RNA nucleotides, lower case letters "c", "g", "a" and "u" represent 2'-O-methyl-modified nucleotides, "s" represents phosphorothioate, "dT" deoxythymidine, and "p" represents 5'-phosphate group (sequences without a "p" in columns 6 and 8 are lacking a 5'-phosphate group).

Table 6. Sequences of bDNA probes for determination of human RRM2. LE=label extender, CE=capture extender, BL=blocking probe.

Table 7. Sequences of bDNA probes for determination of human GAPDH. LE=label extender, CE=capture extender, BL=blocking probe.

Table 8. mRNA knockdown and cell viability dose-response curves, IC50 summary.

Table 9. Time course of mRNA knockdown: >80% mRNA knockdown observed at 24 hr, Percent mRNA knockdown with 5 nM siRNA, relative to mock transfection.

FIG. 1. RRM2 protein knockdown dose-response 24 h post-transfection. A: Western blot B: Quantitation of RRM2 protein in Western blot.

Figure 2:
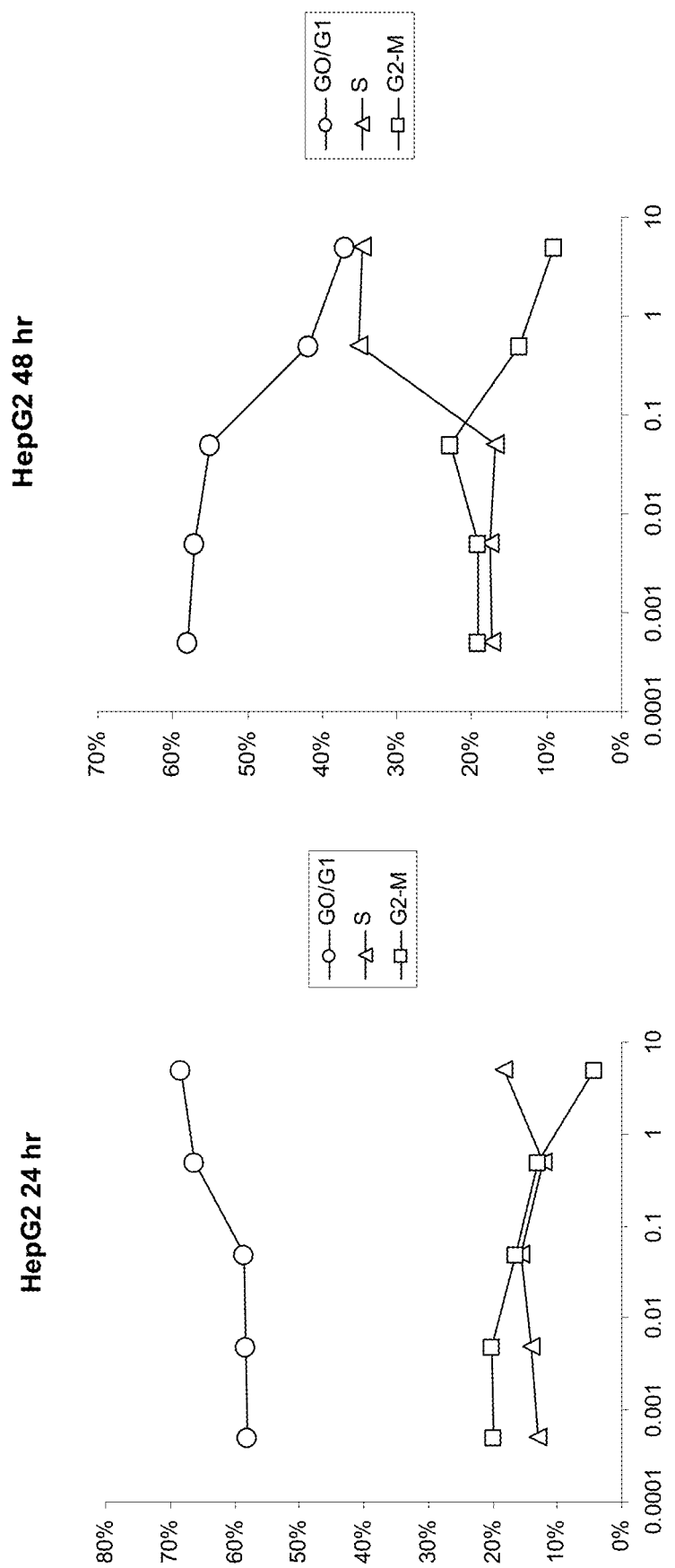

FIG. 2. Cell cycle analysis of HepG2 cells with dsRNA 477/839: FACS analysis following propidium iodide staining indicates that following siRNA treatment cells accumulate in S-phase.

Figure 3:
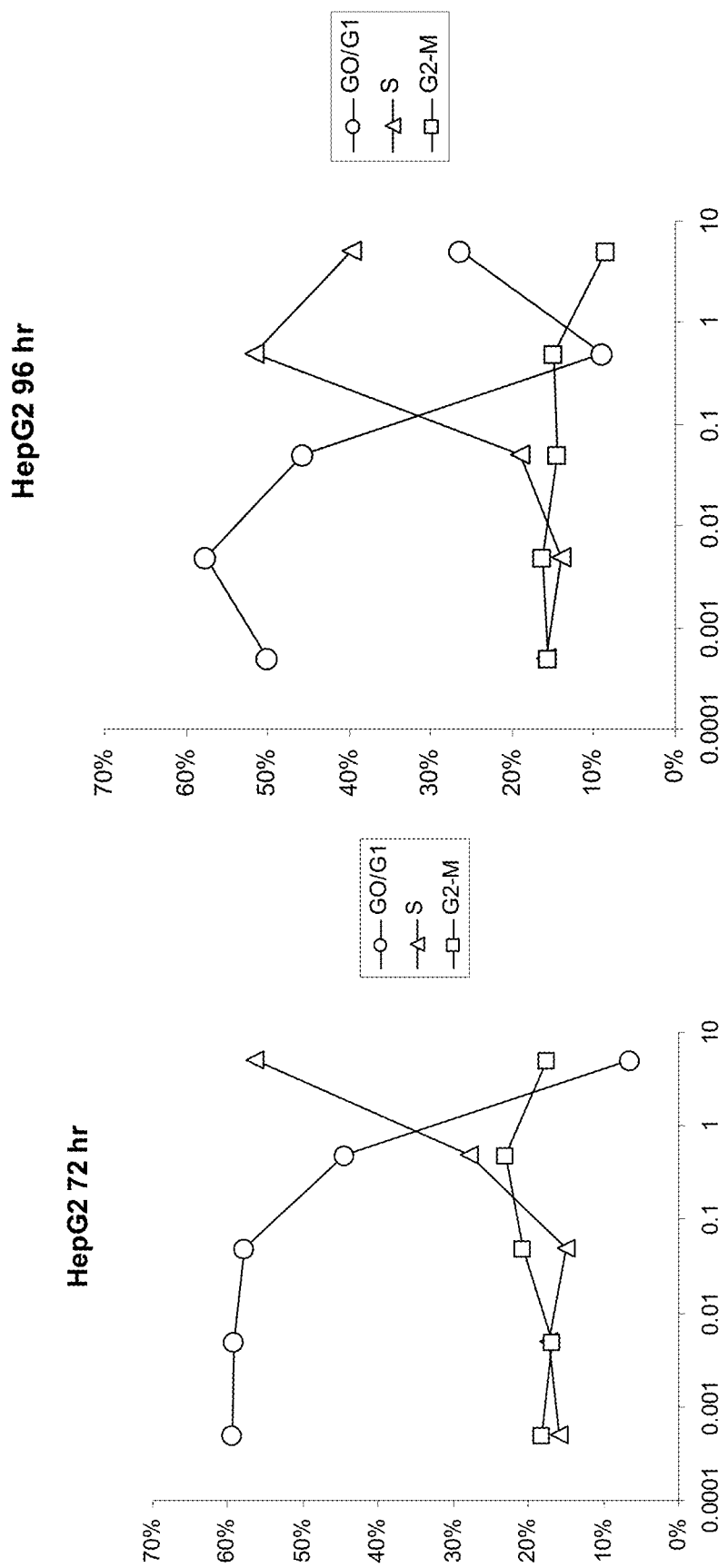

FIG. 3. Cell cycle analysis of HepG2 cells with dsRNA 477/839: FACS analysis following propidium iodide staining indicates that following siRNA treatment cells accumulate in S-phase.

Figure 4:
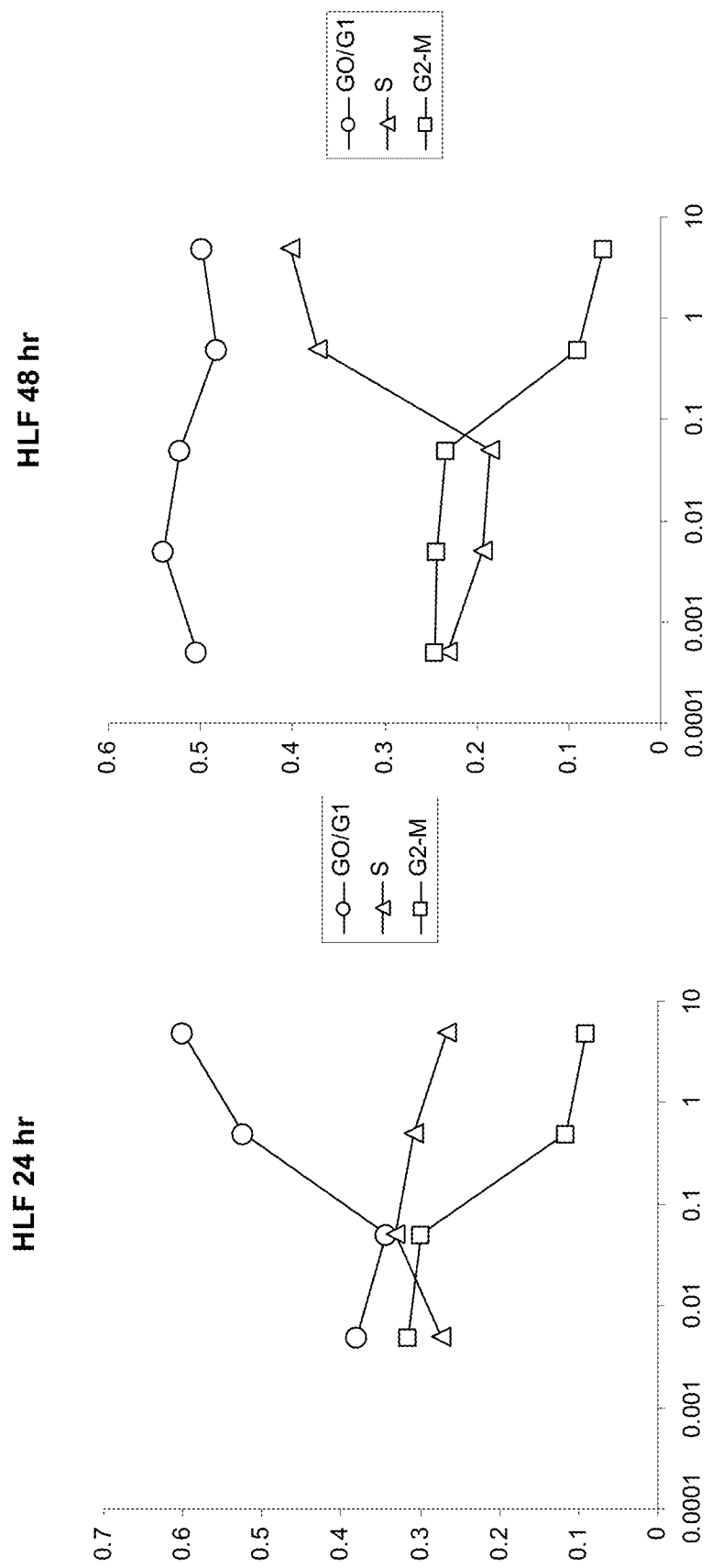

FIG. 4. Cell cycle analysis of HLF cells with dsRNA 477/839: FACS analysis following propidium iodide staining indicates that following siRNA treatment cells accumulate in S-phase.

Figure 5:
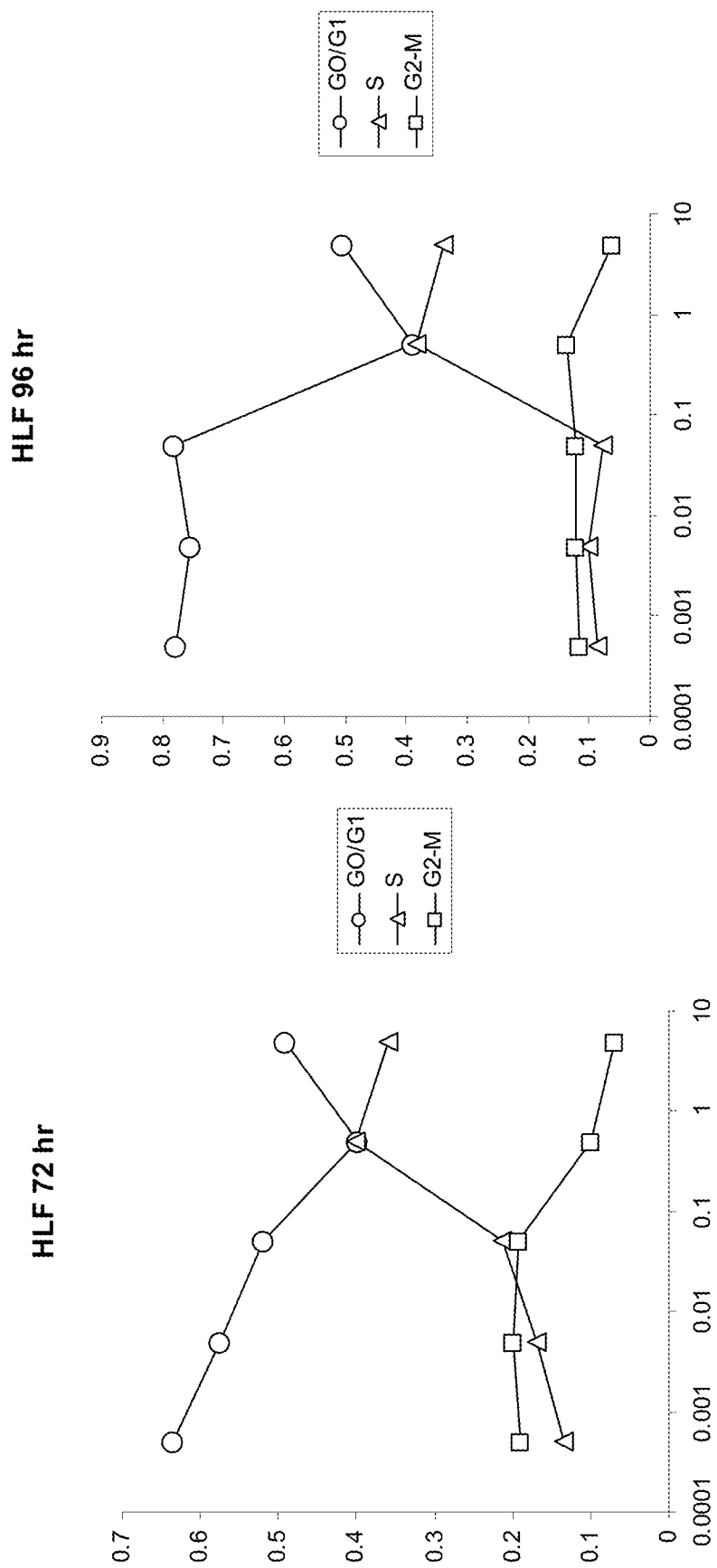

FIG. 5. Cell cycle analysis of HLF cells with dsRNA 477/839: FACS analysis following propidium iodide staining indicates that following siRNA treatment cells accumulate in S-phase.

Figure 6:
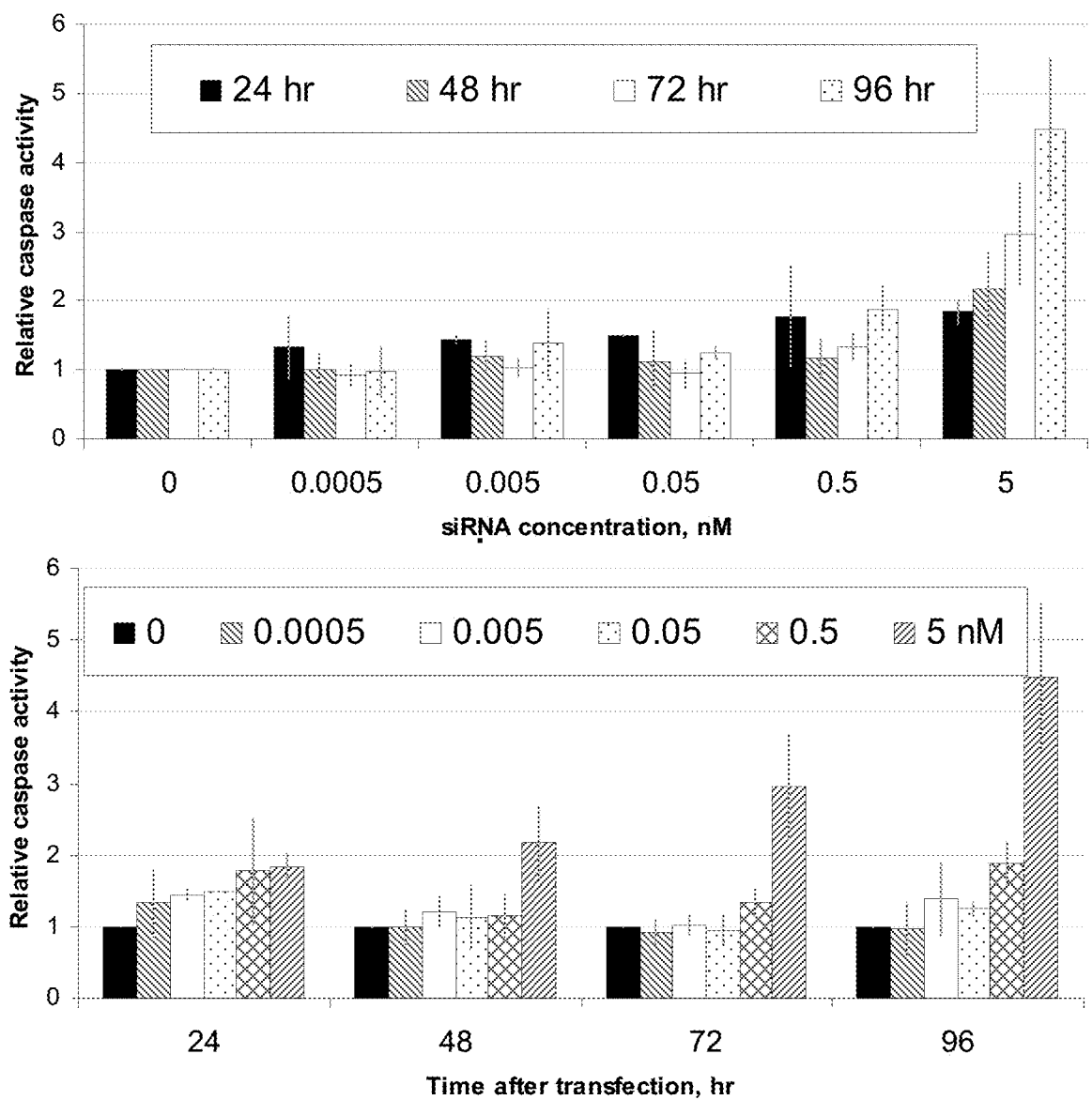

FIG. 6. Apoptosis assay in HepG2 cells. dsRNA 477/839 activates caspase-3/7.

Figure 7:
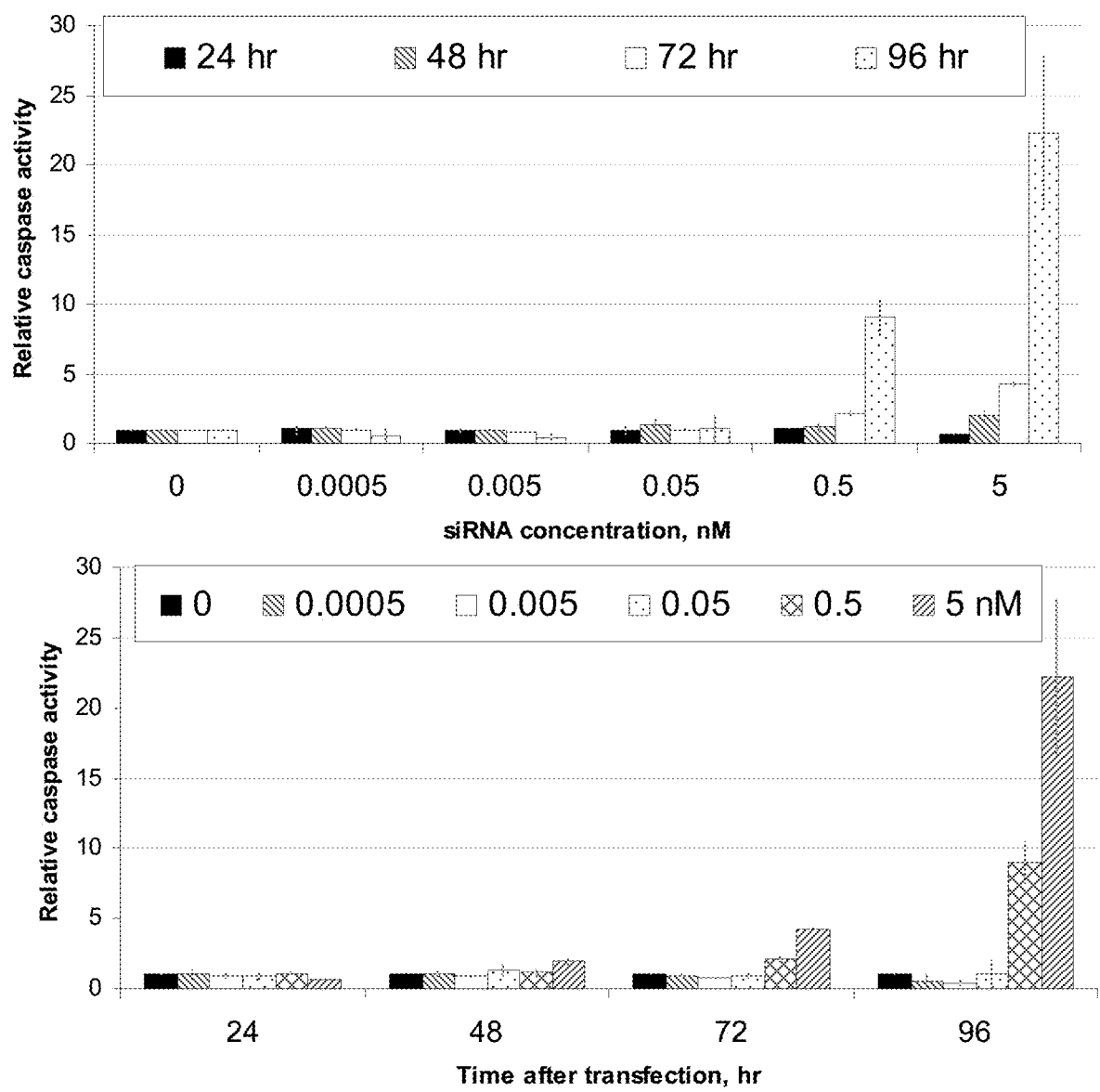

FIG. 7. Apoptosis assay in HLF cells. dsRNA 477/839 activates caspase-3/7.

Figure 8:
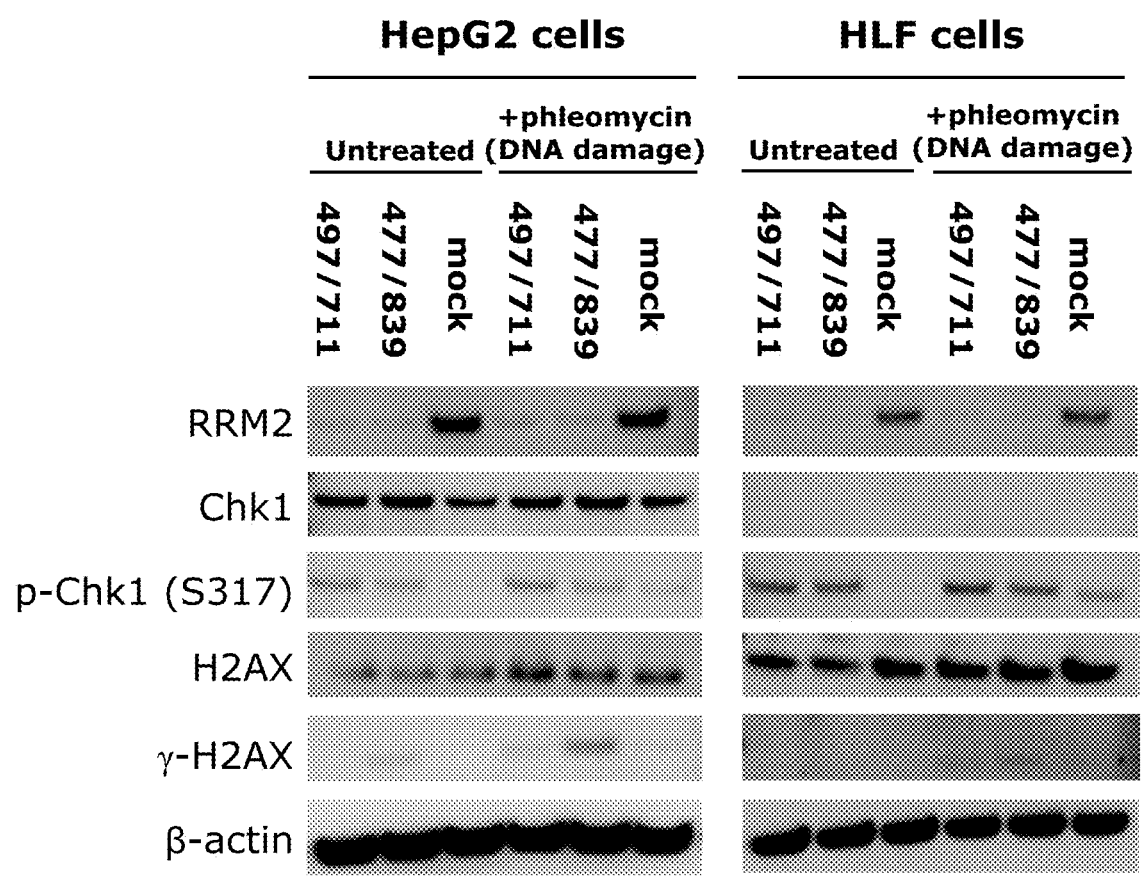

FIG. 8. Effects on components of DNA damage pathway 48 hr post-transfection with RRM2 siRNA (5 nM). RRM2 knockdown activates the pathway (pChk1 and γ-H2AX) even in the absence of phleomycin-induced DNA damage.

EXAMPLES

Identification of dsRNAs for Therapeutic Use dsRNA design was carried out to identify dsRNAs specifically targeting human RRM2 for therapeutic use. First, the known mRNA sequences of human (*Homo sapiens*) RRM2 (NM_001034.3 and NM_001165931.1 listed as SEQ ID NO. 1013 and 1014) were downloaded from NCBI Genbank.

The cynomolgous monkey (*Macaca fascicularis*) RRM2 gene was sequenced (see SEQ ID NO. 1015)

The cynomolgus monkey sequence (SEQ ID NO. 1015) was examined together with the human RRM2 mRNA sequences (SEQ ID NO. 1013 and 1014) by computer analysis to identify homologous sequences of 19 nucleotides that yield RNA interference (RNAi) agents cross-reactive to both sequences.

In identifying RNAi agents, the selection was limited to 19mer sequences having at least 2 mismatches to any other sequence in the human RefSeq database (release 38), which we assumed to represent the comprehensive human transcriptome, by using a proprietary algorithm.

All sequences containing 4 or more consecutive U's (poly-U sequences) or G's (poly-G sequences) were excluded from the synthesis.

The sequences thus identified formed the basis for the synthesis of the RNAi agents in appended Tables 1, 2 and 5. dsRNAs cross-reactive to human as well as cynomolgous monkey were defined as most preferable for therapeutic use.

dsRNA Synthesis

Where the source of a reagent is not specifically given herein, such reagent may be obtained from any supplier of reagents for molecular biology at a quality/purity standard for application in molecular biology.

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

Activity Testing

The activity of the RRM2 dsRNAs for therapeutic use described above was tested in HeLa-S3 cells. Cells in culture were used for quantitation of RRM2 mRNA by branched DNA in total mRNA derived from cells incubated with RRM2-targeting dsRNAs.

HeLa-S3 cells were obtained from American Type Culture Collection (Rockville, Md., cat. No. CCL-2.2) and cultured in Ham's F12 (Biochrom AG, Berlin, Germany, cat. No. FG 0815) supplemented to contain 10% fetal calf serum (FCS) (Biochrom AG, Berlin, Germany, cat. No. S0115), Penicillin 100 U/ml, Streptomycin 100 mg/ml (Biochrom AG, Berlin, Germany, cat. No. A2213) at 37° C. in an atmosphere with 5% $CO_2$ in a humidified incubator (Heraeus HERAcell, Kendro Laboratory Products, Langenselbold, Germany).

Cell seeding and transfection of dsRNA were performed at the same time. For transfection with dsRNA, cells were seeded at a density of 2.0 times.10.sup.4 cells/well in 96-well plates. Transfection with dsRNA was carried out with lipofectamine 2000 (Invitrogen GmbH, Karlsruhe, Germany, cat. No. 11668-019) as described by the manufacturer. In a first single dose experiment dsRNAs were transfected at a concentration of 50 nM. In a second single dose experiment most active dsRNAs were reanalyzed at 500 pM. Most potent dsRNAs and modification variants thereof were tested for improved silencing of RRM2 in single dose at 30 pM. Very effective dsRNAs from single dose screens were further characterized by dose response curves. For this, transfections were performed as described for the single dose screen above, but with the following concentrations of dsRNA (nM): 24, 6, 1.5, 0.375, 0.0938, 0.0234, 0.0059, 0.0015, 0.0004 and 0.0001 nM. After transfection cells were incubated for 24 h at 37° C. and 5% $CO_2$ in a humidified incubator (Heraeus HERAcell, Kendro Laboratory Products, Langenselbold, Germany). bDNA Assay Kit QuantiGene 2.0 (Panomics/Affymetrix, Fremont, USA, Cat-No: 15735) was used for quantification of RRM2 mRNA, while QuantiGene Assay 1.0 (Panomics/Affymetrix, Fremont, USA, Cat-No: QG0004) was used for quantification of GAPDH mRNA. 24 hours after transfection cells were harvested and lysed at 53° C. following procedures recommended by the manufacturer Panomics/Affymetrix for bDNA quantitation of mRNA. Afterwards, 50 µl of the lysates were incubated with probesets specific to human RRM2 and human GAPDH (sequence of probesets see appended tables 7 and 8) and processed according to the manufacturer's protocol for QuantiGene Assay Kit 1 or 2, respectively. Chemoluminescence was measured in a Victor2-Light (Perkin Elmer, Wiesbaden, Germany) as RLUs (relative light units) and values obtained with the human RRM2 probeset were normalized to the respective human GAPDH values for each well. Unrelated control dsRNAs were used as a negative control.

Inhibition data are given in appended tables 2 and 3.

Stability of dsRNAs

Stability of dsRNAs targeting human RRM2 was determined in in vitro assays with either human or mouse serum by measuring the half-life of each single strand.

Measurements were carried out in triplicates for each time point, using 3 µl 50 µM dsRNA sample mixed with 30 µl human serum (Sigma) or mouse serum (Sigma). Mixtures were incubated for either 0 min, 30 min, 1 h, 3 h, 6 h, 24 h, or 48 h at 37° C. As control for unspecific degradation dsRNA was incubated with 30 µl 1×PBS pH 6.8 for 48 h. Reactions were stopped by the addition of 4 µl proteinase K (20 mg/ml), 25 µl of—"Tissue and Cell Lysis Solution" (Epicentre) and 38 µl Millipore water for 30 min at 65° C. Samples were afterwards spin filtered through a 0.2 µm 96 well filter plate at 1400 rpm for 8 min, washed with 55 µl Millipore water twice and spin filtered again.

For separation of single strands and analysis of remaining full length product (FLP), samples were run through an ion exchange Dionex Summit HPLC under denaturing conditions using as eluent A 20 mM Na3PO4 in 10% ACN pH=11 and for eluent B 1 M NaBr in eluent A. The following gradient was applied:

| Time | % A | % B |
|---|---|---|
| −1.0 min | 75 | 25 |
| 1.00 min | 75 | 25 |
| 19.0 min | 38 | 62 |
| 19.5 min | 0 | 100 |
| 21.5 min | 0 | 100 |
| 22.0 min | 75 | 25 |
| 24.0 min | 75 | 25 |

For every injection, the chromatograms were integrated automatically by the Dionex Chromeleon 6.60 HPLC software, and were adjusted manually if necessary. All peak areas were corrected to the internal standard (IS) peak and normalized to the incubation at t=0 min. The area under the peak and resulting remaining FLP was calculated for each single strand and triplicate separately. Half-life (t½) of a strand was defined by the average time point [h] for triplicates at which half of the FLP was degraded. Results are given in appended table 4.

Cytokine Induction

Potential cytokine induction of dsRNAs was determined by measuring the release of INF-α and TNF-α in an in vitro PBMC assay.

Human peripheral blood mononuclear cells (PBMC) were isolated from buffy coat blood of two donors by Ficoll centrifugation at the day of transfection. Cells were transfected in quadruplicates with dsRNA and cultured for 24 h at 37° C. at a final concentration of 130 nM in Opti-MEM, using either Gene Porter 2 (GP2) or DOTAP. dsRNA sequences that were known to induce INF-α and TNF-α in this assay, as well as a CpG oligo, were used as positive controls. Chemical conjugated dsRNA or CpG oligonucleotides that did not need a transfection reagent for cytokine induction, were incubated at a concentration of 500 nM in culture medium. At the end of incubation, the quadruplicate culture supernatant were pooled.

INF-α and TNF-α was then measured in these pooled supernatants by standard sandwich ELISA with two data points per pool. The degree of cytokine induction was expressed relative to positive controls using a score from 0 to 5, with 5 indicating maximum induction. Results are given in appended table 4.

Cell Culture and siRNA Transfections.

HepG2, HLF and A549 cells were obtained from ATCC and maintained in the recommended media, supplemented with 10% fetal bovine serum and 2 mM 1-Glutamine (HepG2: MEME; HLF and A549: DMEM). Cells were transfected using 0.1 µl DharmaFect 1 (Thermo Fisher) per well of a 96-well plate, with each well containing a final volume of 100 µl growth media. Transfections in 6-well plates were carried out in a similar manner, with volumes adjusted for the larger well size. Transfections were performed using a "reverse transfection" protocol, in which cells (HepG2: 5,000 cells; HLF: 2,000 cells; A540: 4,000 cells) were mixed with transfection mix immediately prior to plating.

bDNA Assay.

QuantiGene branched DNA assays (Affymetrix) for mRNA quantitation were run according to the manufacturer's directions using probe sets designed and synthesized by Affymetrix. 40 µl of lysate were used, and signal was normalized to expression of cyclophin B. Results are summarized in table 8 and 9.

Cell Growth Assays.

Cell-Titer Glo assays (Promega) were performed according to the manufacturer's directions. Real-time growth assays were performed on the xCELLigence instrument (Roche) using E-Plate 96 plates. Cell index was measured every hour, and area under the curve calculated at particular time points. Results are summarized in table 8.

Western Blots.

Antibodies for Western blots were obtained from the following sources: Santa Cruz Biotechnology, Inc. (goat polyclonal anti-RRM2, catalog number sc-10844; goat anti-mouse-HRP, catalog number sc-2005); Cell Signaling Technology (rabbit polyclonal anti-Chk1, catalog number 2345; rabbit polyclonal anti-pChk1 (S317), catalog number 2344; goat anti-rabbit-HRP, catalog number 7074; loading control antibody sampler kit (HRP conjugate), catalog number 4670); R&D Systems (mouse monoclonal anti-H2AX, catalog number MAB3406; rabbit polyclonal anti-gamma-H2AX, catalog number AF2288); Promega (donkey anti-goat-HRP, catalog number V8051).

Cells were transfected in 6-well plates and lysed with Pierce M-PER Mammalian Protein Extraction Reagent containing Pierce Halt Protease and Phosphatase Inhibitor Cocktail, according to the manufacturer's recommendations. Protein concentrations were determined using the Pierce Micro BCA Protein Assay Kit. Lysates were run on Novex NuPAGE 4-12% Bis-Tris gels. Protein was transferred to nitrocellulose using the Invitrogen iBlot Dry Blotting System. Western blots were probed using dilutions of antibodies recommended by the manufacturers, and detected using Amersham ECL Plus Western Blotting Detection Reagents. Gel images were collected on a FujiFilm LAS-4000 instrument and quantitated using Multi Gauge v3.1 software. RRM2 protein knock-down dose-response results are shown in FIG. 1. Effects on components of DNA damage pathway (in vivo pharmacodynamic markers) are shown in FIG. 8.

Cell Cycle Assay.

Cells were transfected in 6-well plates and harvested at 24, 48, 72 and 96 hours after transfection. Media was removed and collected in a 50-ml conical tube. Wells were washed with 2 ml PBS and added to the corresponding tubes. Cells were trypsinized, and, once displaced, added to the appropriate tubes. Tubes were centrifuged at 2,000 rpm for 10 min, washed once with 2 ml PBS, and then centrifuged again at 2,000 rpm for 5 min. Supernatants were carefully removed. To fix cells, tubes were tapped to loosen the pellets, and 1.2 ml cold 70% ETOH was added. After vortexing, samples were stored at −20° C. overnight. After thawing cells at room temperature for 20-30 min, 1.2 ml cold PBS was added, and tubes were centrifuged at 2,000 rpm for 10 min. Pellets were washed with 2 ml PBS and centrifuged again at 2,000 rpm. To the pellets was added 0.5 ml propidium iodide/RNase staining buffer (BD Pharmingen, catalog number 550825). Following a 15-min incubation at 37° C., data was collected on FACS LSRII instrument (BD) using DIVA software (10,000 events per sample) and analyzed using FlowJo software. Results are shown in FIGS. 2-5.

Caspase Assay.

Activation of caspase 3/7 was determined using the Apo-ONE Homogeneous Caspase-3/7 assay (Promega), according to the manufacturer's recommendations. Results are shown in FIGS. 6 and 7.

All ranges recited herein encompass all combinations and subcombinations included within that range limit. All patents and publications cited herein are hereby incorporated by reference in their entirety.

TABLE 1

| SEQ ID NO | Sense strand sequence (5'-3') | SEQ ID NO | Antisense strand sequence (5'-3') |
|---|---|---|---|
| 1 | UUGUGGCAGACAGACUUAU | 234 | AUAAGUCUGUCUGCCACAA |
| 2 | CCUGAUGUUCAAACACCUG | 235 | CAGGUGUUUGAACAUCAGG |
| 3 | AGUCCAACAGAGAAUUCUU | 236 | AAGAAUUCUCUGUUGGACU |
| 4 | UAGGCGAGUAUCAGAGGAU | 237 | AUCCUCUGAUACUCGCCUA |
| 5 | GGCGAGUAUCAGAGGAUGG | 238 | CCAUCCUCUGAUACUCGCC |
| 6 | UGUUCAAACACCUGGUACA | 239 | UGUACCAGGUGUUUGAACA |
| 7 | GGGUGACCCUUUAGUGAGC | 240 | GCUCACUAAAGGGUCACCC |
| 8 | GAAGGAAAGACUAACUUCU | 241 | AGAAGUUAGUCUUUCCUUC |
| 9 | UUCUGAAAUGUAUAGUCUU | 242 | AAGACUAUACAUUUCAGAA |
| 10 | CUGUGUAGCUACCUCACAA | 243 | UUGUGAGGUAGCUACACAG |
| 11 | UGCACUCUAAUGAAGCAAU | 244 | AUUGCUUCAUUAGAGUGCA |
| 12 | CCCAUUUGACUUUAUGGAG | 245 | CUCCAUAAAGUCAAAUGGG |
| 13 | AAAUGUAUAGUCUUCUUAU | 246 | AUAAGAAGACUAUACAUUU |
| 14 | UACAUUGAGUUUGUGGCAG | 247 | CUGCCACAAACUCAAUGUA |
| 15 | CAAUACAUUGAGUUUGUGG | 248 | CCACAAACUCAAUGUAUUG |
| 16 | GAACAGGAGUUCCUCACUG | 249 | CAGUGAGGAACUCCUGUUC |
| 17 | AUCCCAUGUUCUGGCUUUC | 250 | GAAAGCCAGAACAUGGGAU |
| 18 | GUAGGUUGUGUGAGUUAAU | 251 | AUUAACUCACACAACCUAC |
| 19 | AUAGUCUUCUUAUUGACAC | 252 | GUGUCAAUAAGAAGACUAU |
| 20 | AUUGCACUCUAAUGAAGCA | 253 | UGCUUCAUUAGAGUGCAAU |
| 21 | UUAUCAAUGCUGUUCGGAU | 254 | AUCCGAACAGCAUUGAUAA |
| 22 | AGAAACGAGGACUGAUGCC | 255 | GGCAUCAGUCCUCGUUUCU |
| 23 | CAUUGAGUUUGUGGCAGAC | 256 | GUCUGCCACAAACUCAAUG |
| 24 | ACAUUCAGCACUGGGAAUC | 257 | GAUUCCCAGUGCUGAAUGU |
| 25 | UGAUGUUCAAACACCUGGU | 258 | ACCAGGUGUUUGAACAUCA |

TABLE 1-continued

| SEQ ID NO | Sense strand sequence (5'-3') | SEQ ID NO | Antisense strand sequence (5'-3') |
|---|---|---|---|
| 26 | GGAUAGAACAGGAGUUCCU | 259 | AGGAACUCCUGUUCUAUCC |
| 27 | AAUAUUUCACUGGAAGGAA | 260 | UUCCUUCCAGUGAAAUAUU |
| 28 | AAUAAACAUUGUUUGUACU | 261 | AGUACAAACAAUGUUUAUU |
| 29 | UCCCAUGUUCUGGCUUUCU | 262 | AGAAAGCCAGAACAUGGGA |
| 30 | UUCGGAUAGAACAGGAGUU | 263 | AACUCCUGUUCUAUCCGAA |
| 31 | AAGUAGGUUGUGUGAGUUA | 264 | UAACUCACACAACCUACUU |
| 32 | UUAUAGUGCUGGUAGUAUC | 265 | GAUACUACCAGCACUAUAA |
| 33 | CUUCUUAUUGACACUUACA | 266 | UGUAAGUGUCAAUAAGAAG |
| 34 | UACAGAAGCCCGCUGUUUC | 267 | GAAACAGCGGGCUUCUGUA |
| 35 | GUGACCCUUUAGUGAGCUU | 268 | AAGCUCACUAAAGGGUCAC |
| 36 | AUAGAACAGGAGUUCCUCA | 269 | UGAGGAACUCCUGUUCUAU |
| 37 | CUGGCACUUUACAAACAAA | 270 | UUUGUUUGUAAAGUGCCAG |
| 38 | UCUAAUGAAGCAAUACAUU | 271 | AAUGUAUUGCUUCAUUAGA |
| 39 | UCUUCUUAUUGACACUUAC | 272 | GUAAGUGUCAAUAAGAAGA |
| 40 | UGUUCGGAUAGAACAGGAG | 273 | CUCCUGUUCUAUCCGAACA |
| 41 | AGUACCAUGAUAUCUGGCA | 274 | UGCCAGAUAUCAUGGUACU |
| 42 | CAGAGAUGAGGGUUUACAC | 275 | GUGUAAACCCUCAUCUCUG |
| 43 | GAAACGAGGACUGAUGCCU | 276 | AGGCAUCAGUCCUCGUUUC |
| 44 | AAGAGAGUAGGCGAGUAUC | 277 | GAUACUCGCCUACUCUCUU |
| 45 | CAUUAGCUGAAUAAUGUGA | 278 | UCACAUUAUUCAGCUAAUG |
| 46 | AGUAGAGAACCCAUUUGAC | 279 | GUCAAAUGGGUUCUCUACU |
| 47 | AGGCGAGUAUCAGAGGAUG | 280 | CAUCCUCUGAUACUCGCCU |
| 48 | UAGACUAAGCAUGUAAUUU | 281 | AAAUUACAUGCUUAGUCUA |
| 49 | AACAUUGUUUGUACUCACA | 282 | UGUGAGUACAAACAAUGUU |
| 50 | GAUGGGAGUGAUGUCAAGU | 283 | ACUUGACAUCACUCCCAUC |
| 51 | CAGACCAUUUCCUAAUCAG | 284 | CUGAUUAGGAAAUGGUCUG |
| 52 | GAUUACAGAAGCCCGCUGU | 285 | ACAGCGGGCUUCUGUAAUC |
| 53 | CAUUGAAACGAUGCCUUGU | 286 | ACAAGGCAUCGUUUCAAUG |
| 54 | ACUUAUGCUGGAACUGGGU | 287 | ACCCAGUUCCAGCAUAAGU |
| 55 | GUCGACAAGGAGAACACGC | 288 | GCGUGUUCUCCUUGUCGAC |
| 56 | AGGAAAGACUAACUUCUUU | 289 | AAAGAAGUUAGUCUUUCCU |
| 57 | CAAGACCGCGAGGAGGAUC | 290 | GAUCCUCCUCGCGGUCUUG |
| 58 | GACAAUGGCAGUCUUGGCU | 291 | AGCCAAGACUGCCAUUGUC |
| 59 | AUGCCUUGUGUCAAGAAGA | 292 | UCUUCUUGACACAAGGCAU |
| 60 | GCCUCACUGCUUCAACGCA | 293 | UGCGUUGAAGCAGUGAGGC |
| 61 | UACCUCACAACCAGUCCUG | 294 | CAGGACUGGUUGUGAGGUA |
| 62 | GAGAAGAGAGUAGGCGAGU | 295 | ACUCGCCUACUCUCUUCUC |
| 63 | AGACUUAUGCUGGAACUGG | 296 | CCAGUUCCAGCAUAAGUCU |

TABLE 1-continued

| SEQ ID NO | Sense strand sequence (5'-3') | SEQ ID NO | Antisense strand sequence (5'-3') |
|---|---|---|---|
| 64 | UUACAGAAGCCCGCUGUUU | 297 | AAACAGCGGGCUUCUGUAA |
| 65 | UUAUGCUGGAACUGGGUUU | 298 | AAACCCAGUUCCAGCAUAA |
| 66 | AUAAACAUUGUUUGUACUC | 299 | GAGUACAAACAAUGUUUAU |
| 67 | UCAAUGCCAUUGAAACGAU | 300 | AUCGUUUCAAUGGCAUUGA |
| 68 | AUAGUGCUGGUAGUAUCAC | 301 | GUGAUACUACCAGCACUAU |
| 69 | CAGCCUCACUGCUUCAACG | 302 | CGUUGAAGCAGUGAGGCUG |
| 70 | UCUUGGCUUUAAAGUGAGG | 303 | CCUCACUUUAAAGCCAAGA |
| 71 | GGCUGUGACUUACCAUAGC | 304 | GCUAUGGUAAGUCACAGCC |
| 72 | GGCUACCUAUGGUGAACGU | 305 | ACGUUCACCAUAGGUAGCC |
| 73 | CGCGAGGAGGAUCUUCCAG | 306 | CUGGAAGAUCCUCCUCGCG |
| 74 | GCCAUUGAAACGAUGCCUU | 307 | AAGGCAUCGUUUCAAUGGC |
| 75 | AGCCUCACUGCUUCAACGC | 308 | GCGUUGAAGCAGUGAGGCU |
| 76 | GGCAGACAGACUUAUGCUG | 309 | CAGCAUAAGUCUGUCUGCC |
| 77 | GUGACUAAAGUAAGUUAAA | 310 | UUUAACUUACUUUAGUCAC |
| 78 | AGUUAUUGUUACCUAAAGU | 311 | ACUUUAGGUAACAAUAACU |
| 79 | GCCUUUAUGUUUGGGAGAA | 312 | UUCUCCCAAACAUAAAGGC |
| 80 | UUCAGAGUAGAGAACCCAU | 313 | AUGGGUUCUCUACUCUGAA |
| 81 | AAACGAGGACUGAUGCCUG | 314 | CAGGCAUCAGUCCUCGUUU |
| 82 | GUAGGCGAGUAUCAGAGGA | 315 | UCCUCUGAUACUCGCCUAC |
| 83 | AAGCCCGCUGUUUCUAUGG | 316 | CCAUAGAAACAGCGGGCUU |
| 84 | UCAGCACUGGGAAUCCCUG | 317 | CAGGGAUUCCCAGUGCUGA |
| 85 | GAAUAAUGUGAGGAUUAAC | 318 | GUUAAUCCUCACAUUAUUC |
| 86 | UGUGGCAGACAGACUUAUG | 319 | CAUAAGUCUGUCUGCCACA |
| 87 | AGAGAUAAAUGUUGAUCUU | 320 | AAGAUCAACAUUUAUCUCU |
| 88 | UACCAUGAUAUCUGGCAGA | 321 | UCUGCCAGAUAUCAUGGUA |
| 89 | CUUCCAAAUUGCCAUGGAA | 322 | UUCCAUGGCAAUUUGGAAG |
| 90 | ACCGCGAGGAGGAUCUUCC | 323 | GGAAGAUCCUCCUCGCGGU |
| 91 | GAAAUGUAUAGUCUUCUUA | 324 | UAAGAAGACUAUACAUUUC |
| 92 | AUGUUCAAACACCUGGUAC | 325 | GUACCAGGUGUUUGAACAU |
| 93 | AGGGAAUUUCUCUUCAAUG | 326 | CAUUGAAGAGAAAUUCCCU |
| 94 | CCCUGUUAAGUGGUGAAAU | 327 | AUUUCACCACUUAACAGGG |
| 95 | GAUGAGGGUUUACACUGUG | 328 | CACAGUGUAAACCCUCAUC |
| 96 | UGUGUGAGUUAAUUCAUUU | 329 | AAAUGAAUUAACUCACACA |
| 97 | UUGCCUGAUGUUCAAACAC | 330 | GUGUUUGAACAUCAGGCAA |
| 98 | AAACUUGUGUAGACUAAGC | 331 | GCUUAGUCUACACAAGUUU |
| 99 | UAUAUCCCAUGUUCUGGCU | 332 | AGCCAGAACAUGGGAUAUA |
| 100 | UUGUGUAGACUAAGCAUGU | 333 | ACAUGCUUAGUCUACACAA |
| 101 | AUGCUGUUCGGAUAGAACA | 334 | UGUUCUAUCCGAACAGCAU |
| 102 | AAUUAUCAAUGCUGUUCGG | 335 | CCGAACAGCAUUGAUAAUU |

TABLE 1-continued

| SEQ ID NO | Sense strand sequence (5'-3') | SEQ ID NO | Antisense strand sequence (5'-3') |
|---|---|---|---|
| 103 | GCCUGAUGUUCAAACACCU | 336 | AGGUGUUUGAACAUCAGGC |
| 104 | CAUAGCAGUGACAAUGGCA | 337 | UGCCAUUGUCACUGCUAUG |
| 105 | UGUGAGUUAAUUCAUUUAU | 338 | AUAAAUGAAUUAACUCACA |
| 106 | AGUGCUGGUAGUAUCACCU | 339 | AGGUGAUACUACCAGCACU |
| 107 | UAUCAAUGCUGUUCGGAUA | 340 | UAUCCGAACAGCAUUGAUA |
| 108 | GACUAAAGUAAGUUAAACU | 341 | AGUUUAACUUACUUUAGUC |
| 109 | AAUGCUGUUCGGAUAGAAC | 342 | GUUCUAUCCGAACAGCAUU |
| 110 | AGAAUAUUUCACUGGAAGG | 343 | CCUUCCAGUGAAAUAUUCU |
| 111 | AUCUGGCAGAUGUAUAAGA | 344 | UCUUAUACAUCUGCCAGAU |
| 112 | UAUAGUGCUGGUAGUAUCA | 345 | UGAUACUACCAGCACUAUA |
| 113 | GGCCAGCAAGACCGCGAGG | 346 | CCUCGCGGUCUUGCUGGCC |
| 114 | CCAUGAUAUCUGGCAGAUG | 347 | CAUCUGCCAGAUAUCAUGG |
| 115 | UUAAACUUGUGUAGACUAA | 348 | UUAGUCUACACAAGUUUAA |
| 116 | UUCAAUGCCAUUGAAACGA | 349 | UCGUUUCAAUGGCAUUGAA |
| 117 | AGAAAGCUGAGACAUUGCA | 350 | UGCAAUGUCUCAGCUUUCU |
| 118 | CUAUGGCUUCCAAAUUGCC | 351 | GGCAAUUUGGAAGCCAUAG |
| 119 | AAGUGACUAAAGUAAGUUA | 352 | UAACUUACUUUAGUCACUU |
| 120 | UGACUAAAGUAAGUUAAAC | 353 | GUUUAACUUACUUUAGUCA |
| 121 | UGCUGUUCGGAUAGAACAG | 354 | CUGUUCUAUCCGAACAGCA |
| 122 | GCGAGUAUCAGAGGAUGGG | 355 | CCCAUCCUCUGAUACUCGC |
| 123 | GGGCCUUGCGCUGGAUUGG | 356 | CCAAUCCAGCGCAAGGCCC |
| 124 | ACCUCACAACCAGUCCUGU | 357 | ACAGGACUGGUUGUGAGGU |
| 125 | ACUAAGUGACUAAAGUAAG | 358 | CUUACUUUAGUCACUUAGU |
| 126 | AUUACAGAAGCCCGCUGUU | 359 | AACAGCGGGCUUCUGUAAU |
| 127 | GAGUAGGCGAGUAUCAGAG | 360 | CUCUGAUACUCGCCUACUC |
| 128 | CAGUGACAAUGGCAGUCUU | 361 | AAGACUGCCAUUGUCACUG |
| 129 | GGCCUUGCGCUGGAUUGGG | 362 | CCCAAUCCAGCGCAAGGCC |
| 130 | UUCUUAUUGACACUUACAU | 363 | AUGUAAGUGUCAAUAAGAA |
| 131 | UUCACUAAGUGACUAAAGU | 364 | ACUUUAGUCACUUAGUGAA |
| 132 | GUGUGAGUUAAUUCAUUUA | 365 | UAAAUGAAUUAACUCACAC |
| 133 | CCCGCUCGCGCCCAUCACG | 366 | CGUGAUGGGCGCGAGCGGG |
| 134 | GUAAGUUAAACUUGUGUAG | 367 | CUACACAAGUUUAACUUAC |
| 135 | CGGAAGUUGGAAUCAGGUU | 368 | AACCUGAUUCCAACUUCCG |
| 136 | AUGUGAGGAUUAACUUCUG | 369 | CAGAAGUUAAUCCUCACAU |
| 137 | UUAAGUGGUGAAAUCAACU | 370 | AGUUGAUUUCACCACUUAA |
| 138 | UGUAGACUAAGCAUGUAAU | 371 | AUUACAUGCUUAGUCUACA |
| 139 | AUAAUGUGAGGAUUAACUU | 372 | AAGUUAAUCCUCACAUUAU |
| 140 | GGCUGGCUGUGACUUACCA | 373 | UGGUAAGUCACAGCCAGCC |

TABLE 1-continued

| SEQ ID NO | Sense strand sequence (5'-3') | SEQ ID NO | Antisense strand sequence (5'-3') |
|---|---|---|---|
| 141 | AAGAGGCUACCUAUGGUGA | 374 | UCACCAUAGGUAGCCUCUU |
| 142 | CAGAUUACAGAAGCCCGCU | 375 | AGCGGGCUUCUGUAAUCUG |
| 143 | UGAGGCCUUGCCUGUGAAG | 376 | CUUCACAGGCAAGGCCUCA |
| 144 | AUAAUUAUCAAUGCUGUUC | 377 | GAACAGCAUUGAUAAUUAU |
| 145 | GUGACUUACCAUAGCAGUG | 466 | CACUGCUAUGGUAAGUCAC |
| 146 | UAGGGCUACUUUGAAUUAA | 378 | UUAAUUCAAAGUAGCCCUA |
| 147 | UGGCAGAUGUAUAAGAAGG | 379 | CCUUCUUAUACAUCUGCCA |
| 148 | AUAGCUUGAUUUAUUUGGU | 380 | ACCAAAUAAAUCAAGCUAU |
| 149 | CAGCAAGACCGCGAGGAGG | 381 | CCUCCUCGCGGUCUUGCUG |
| 150 | GACUGAUGCCUGGCCUCAC | 382 | GUGAGGCCAGGCAUCAGUC |
| 151 | UUACCUUGGAUGCUGACUU | 383 | AAGUCAGCAUCCAAGGUAA |
| 152 | AUUCAGCACUGGGAAUCCC | 384 | GGGAUUCCCAGUGCUGAAU |
| 153 | AGCAAGACCGCGAGGAGGA | 385 | UCCUCCUCGCGGUCUUGCU |
| 154 | AGGGCUACUUUGAAUUAAU | 386 | AUUAAUUCAAAGUAGCCCU |
| 155 | UAAGUUAUUGUUACCUAAA | 387 | UUUAGGUAACAAUAACUUA |
| 156 | UUUAUAGUGCUGGUAGUAU | 388 | AUACUACCAGCACUAUAAA |
| 157 | GCAAGACCGCGAGGAGGAU | 389 | AUCCUCCUCGCGGUCUUGC |
| 158 | UCUAUGGCUUCCAAAUUGC | 390 | GCAAUUUGGAAGCCAUAGA |
| 159 | AAAGACUAACUUCUUUGAG | 391 | CUCAAAGAAGUUAGUCUUU |
| 160 | ACCAUGAUAUCUGGCAGAU | 392 | AUCUGCCAGAUAUCAUGGU |
| 161 | GACCAUUUCCUAAUCAGUU | 393 | AACUGAUUAGGAAAUGGUC |
| 162 | UUACCAUAGCAGUGACAAU | 394 | AUUGUCACUGCUAUGGUAA |
| 163 | AAUGUGAGGAUUAACUUCU | 395 | AGAAGUUAAUCCUCACAUU |
| 164 | UAGUGUCCUGGGAUUCUCU | 396 | AGAGAAUCCCAGGACACUA |
| 165 | UGUUAAGUGGUGAAAUCAA | 397 | UUGAUUUCACCACUUAACA |
| 166 | ACAAAUAUUCUUAAUAGGG | 398 | CCCUAUUAAGAAUAUUUGU |
| 167 | GCGGAAGUUGGAAUCAGGU | 399 | ACCUGAUUCCAACUUCCGC |
| 168 | AACUUGUGUAGACUAAGCA | 400 | UGCUUAGUCUACACAAGUU |
| 169 | AUUCUUAAUAGGGCUACUU | 401 | AAGUAGCCCUAUUAAGAAU |
| 170 | CCUAAAGUUAAUCCAGAUU | 402 | AAUCUGGAUUAACUUUAGG |
| 171 | UAUUGUUACCUAAAGUUAA | 403 | UUAACUUUAGGUAACAAUA |
| 172 | GUGCUGGUAGUAUCACCUU | 404 | AAGGUGAUACUACCAGCAC |
| 173 | CUGUGACUUACCAUAGCAG | 405 | CUGCUAUGGUAAGUCACAG |
| 174 | GAGCUUCUUAAGUUAAAUC | 406 | GAUUUAACUUAAGAAGCUC |
| 175 | CUGUUCGGAUAGAACAGGA | 407 | UCCUGUUCUAUCCGAACAG |
| 176 | GUUAUUGUUACCUAAAGUU | 408 | AACUUUAGGUAACAAUAAC |
| 177 | UAAUGUGAGGAUUAACUUC | 409 | GAAGUUAAUCCUCACAUUA |
| 178 | ACCACUAAUGGGAGCCAAU | 410 | AUUGGCUCCCAUUAGUGGU |
| 179 | UGUGUAGACUAAGCAUGUA | 411 | UACAUGCUUAGUCUACACA |

TABLE 1-continued

| SEQ ID NO | Sense strand sequence (5'-3') | SEQ ID NO | Antisense strand sequence (5'-3') |
|---|---|---|---|
| 180 | UGGGCCUUGCGCUGGAUUG | 412 | CAAUCCAGCGCAAGGCCCA |
| 181 | AGGAGCUUCUUAAGUUAAA | 413 | UUUAACUUAAGAAGCUCCU |
| 182 | GGUGACCCUUUAGUGAGCU | 414 | AGCUCACUAAAGGGUCACC |
| 183 | AGAGUAGGCGAGUAUCAGA | 415 | UCUGAUACUCGCCUACUCU |
| 184 | GCAGUGACAAUGGCAGUCU | 416 | AGACUGCCAUUGUCACUGC |
| 185 | AAACGAUGCCUUGUGUCAA | 417 | UUGACACAAGGCAUCGUUU |
| 186 | GGACUGAUGCCUGGCCUCA | 418 | UGAGGCCAGGCAUCAGUCC |
| 187 | UGAGAGAUAAAUGUUGAUC | 419 | GAUCAACAUUUAUCUCUCA |
| 188 | UGGUUUCUACACCAAAUAC | 420 | GUAUUUGGUGUAGAAACCA |
| 189 | UCUCUGUAAUAUGAUACAU | 421 | AUGUAUCAUAUUACAGAGA |
| 190 | GAGAGAUAAAUGUUGAUCU | 422 | AGAUCAACAUUUAUCUCUC |
| 191 | ACUCUAAUGAAGCAAUACA | 423 | UGUAUUGCUUCAUUAGAGU |
| 192 | UGAAGUGUUACCAACUAGC | 424 | GCUAGUUGGUAACACUUCA |
| 193 | AAUGAAGCAAUACAUUGAG | 425 | CUCAAUGUAUUGCUUCAUU |
| 194 | ACGAUGCCUUGUGUCAAGA | 426 | UCUUGACACAAGGCAUCGU |
| 195 | AGACCGCGAGGAGGAUCUU | 427 | AAGAUCCUCCUCGCGGUCU |
| 196 | UUGUUACCUAAAGUUAAUC | 428 | GAUUAACUUUAGGUAACAA |
| 197 | CAGAAGCCCGCUGUUUCUA | 429 | UAGAAACAGCGGGCUUCUG |
| 198 | UUUGACUUUAUGGAGAAUA | 430 | UAUUCUCCAUAAAGUCAAA |
| 199 | UACCUAAAGUUAAUCCAGA | 431 | UCUGGAUUAACUUUAGGUA |
| 200 | UUCAAACACCUGGUACACA | 432 | UGUGUACCAGGUGUUUGAA |
| 201 | UUGCACUCUAAUGAAGCAA | 433 | UUGCUUCAUUAGAGUGCAA |
| 202 | UGUUACCUAAAGUUAAUCC | 434 | GGAUUAACUUUAGGUAACA |
| 203 | CACUAAGUGACUAAAGUAA | 435 | UUACUUUAGUCACUUAGUG |
| 204 | UGCCAGAUAGAAGACAGGU | 436 | ACCUGUCUUCUAUCUGGCA |
| 205 | AAUGUAUAGUCUUCUUAUU | 437 | AAUAAGAAGACUAUACAUU |
| 206 | GACCACUAAUGGGAGCCAA | 438 | UUGGCUCCCAUUAGUGGUC |
| 207 | GUUACCUAAAGUUAAUCCA | 439 | UGGAUUAACUUUAGGUAAC |
| 208 | UGAUGCCUGGCCUCACAUU | 440 | AAUGUGAGGCCAGGCAUCA |
| 209 | CCAACUUUAAAGUCAGUCC | 441 | GGACUGACUUUAAAGUUGG |
| 210 | UAACUUGUGUAGACUAAG | 442 | CUUAGUCUACACAAGUUUA |
| 211 | AGUAGGUUGUGUGAGUUAA | 443 | UUAACUCACACAACCUACU |
| 212 | GUUAAACUUGUGUAGACUA | 444 | UAGUCUACACAAGUUUAAC |
| 213 | CUGACCACUAAUGGGAGCC | 445 | GGCUCCCAUUAGUGGUCAG |
| 214 | UAUUCUUAAUAGGGCUACU | 446 | AGUAGCCCUAUUAAGAAUA |
| 215 | GUAGUGUCCUGGGAUUCUC | 447 | GAGAAUCCCAGGACACUAC |
| 216 | UAUCUGGCAGAUGUAUAAG | 448 | CUUAUACAUCUGCCAGAUA |
| 217 | AGGCUACCUAUGGUGAACG | 449 | CGUUCACCAUAGGUAGCCU |

TABLE 1-continued

| SEQ ID NO | Sense strand sequence (5'-3') | SEQ ID NO | Antisense strand sequence (5'-3') |
|---|---|---|---|
| 218 | UCAGACCAUUUCCUAAUCA | 450 | UGAUUAGGAAAUGGUCUGA |
| 219 | UUACCUAAAGUUAAUCCAG | 451 | CUGGAUUAACUUUAGGUAA |
| 220 | GGUUUCUACACCAAAUACA | 452 | UGUAUUUGGUGUAGAAACC |
| 221 | GUUGGUGCCAGAUAGAAGA | 453 | UCUUCUAUCUGGCACCAAC |
| 222 | GCUACCUAUGGUGAACGUG | 454 | CACGUUCACCAUAGGUAGC |
| 223 | UCACUAAGUGACUAAAGUA | 455 | UACUUUAGUCACUUAGUGA |
| 224 | UUAUUGUUACCUAAAGUUA | 456 | UAACUUUAGGUAACAAUAA |
| 225 | UAGCUGAAUAAUGUGAGGA | 457 | UCCUCACAUUAUUCAGCUA |
| 226 | UGACCACUAAUGGGAGCCA | 458 | UGGCUCCCAUUAGUGGUCA |
| 227 | GUAGCUACCUCACAACCAG | 459 | CUGGUUGUGAGGUAGCUAC |
| 228 | UCCCGCUCGCGCCCAUCAC | 460 | GUGAUGGGCGCGAGCGGGA |
| 229 | CUUGGCUUUAAAGUGAGGG | 461 | CCCUCACUUUAAAGCCAAG |
| 230 | AGAAGCCCGCUGUUUCUAU | 462 | AUAGAAACAGCGGGCUUCU |
| 231 | ACUAAAGUAAGUUAAACUU | 463 | AAGUUUAACUUACUUUAGU |
| 232 | AGUAAGUUAAACUUGUGUA | 464 | UACACAAGUUUAACUUACU |
| 233 | AAUAAUUAUCAAUGCUGUU | 465 | AACAGCAUUGAUAAUUAUU |

TABLE 2

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 526 agGAAAGAcuAAcuucuuudTsdT | 967 AAAGAAGUuAGUCUUUCCUdTsdT | n.d. | n.d. | n.d. | n.d. | 10 | 2 | 42 | 1 |
| 477 uucuGAAAuGuAuAGucuudTsdT | 963 AAGACuAUAcAUUUcAGAAdTsdT | n.d. | n.d. | n.d. | n.d. | 8 | 1 | 48 | 2 |
| 470 aguccAAcAGAGAAuucuudTsdT | 962 AAGAAUUCUCUGUUUGGACUdTsdT | n.d. | n.d. | n.d. | n.d. | 7 | 0 | 49 | 2 |
| 476 gaAGGAAAGAcuAAcuucudTsdT | 966 AGAAGUuAGUCUUUCCUUCdTsdT | n.d. | n.d. | n.d. | n.d. | 8 | 2 | 50 | 2 |
| 507 ucuucuuAuuGAcAcuuAcdTsdT | 964 GUAAGUGUcAAuAAGAAGAdTsdT | n.d. | n.d. | n.d. | n.d. | 3 | 1 | 53 | 3 |
| 553 guAGGcGAGuAucAGAGGAdTsdT | 968 UCCUCUGAuACUCGCCuACdTsdT | n.d. | n.d. | n.d. | n.d. | 12 | 2 | 54 | 4 |
| 501 cuucuAuuGAcAcuuAcAdTsdT | 965 UGuAAGUGUcAAuAAGAAGdTsdT | n.d. | n.d. | n.d. | n.d. | 9 | 1 | 58 | 7 |
| 497 ucccAuGuucuGGcuuucudTsdT | 961 AGAAAGCcAGAAcAUGGGAdTsdT | n.d. | n.d. | n.d. | n.d. | 5 | 1 | 70 | 7 |
| 508 ucuucuUAuuGAcAcuuAcdTsdT | 972 GUAAGUGUcAAuAaGAAGAdTsdT | n.d. | n.d. | n.d. | n.d. | 14 | 1 | 85 | 8 |
| 470 aguccAAcAGAGAAuucuudTsdT | 970 AAGAAUUCUCUGUuGGACUdTsdT | n.d. | n.d. | n.d. | n.d. | 15 | 1 | 89 | 2 |
| 477 uucuGAAAuGuAuAGucuudTsdT | 971 AAGACuAUAcAUUucAGAAdTsdT | n.d. | n.d. | n.d. | n.d. | 18 | 3 | 89 | 9 |
| 508 ucuucuUAuuGAcAcuuAcdTsdT | 985 GuAAGUGUcAAuAaGAAGAdTsdT | n.d. | n.d. | n.d. | n.d. | 11 | 2 | 91 | 5 |
| 507 ucuucuuAuuGAcAcuuAcdTsdT | 972 GUAAGUGUcAAuAaGAAGAdTsdT | n.d. | n.d. | n.d. | n.d. | 14 | 2 | 91 | 10 |
| 470 aguccAAcAGAGAAuucuudTsdT | 978 AaGAAUUCUCUGUuGGACUdTsdT | n.d. | n.d. | n.d. | n.d. | 24 | 3 | 92 | 7 |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 501 cuucuuAuuGAcAcuuAcAdTsdT | 973 UGuAAGUGUcAAuaAGAAGdTsdT | n.d. | n.d. | n.d. | n.d. | 34 | 4 | 95 | 5 |
| 497 ucccAuGuucuGGcuuucudTsdT | 969 AGAAAGCcAGAAcaUGGGAdTsdT | n.d. | n.d. | n.d. | n.d. | 39 | 5 | 96 | 9 |
| 476 gaAGGAAAGAcuAAcuucucudTsdT | 974 AGAAGUuAGUCUUuCCUUCdTsdT | n.d. | n.d. | n.d. | n.d. | 14 | 1 | 97 | 8 |
| 553 guAGGcGAGuAucAGAGGAdTsdT | 984 UcCUCUGAuACUCgCCuACdTsdT | n.d. | n.d. | n.d. | n.d. | 35 | 3 | 98 | 9 |
| 526 agGAAAGAcuAAcuucuuudTsdT | 983 AaAGAAGUuAGUCuUUCCUdTsdT | n.d. | n.d. | n.d. | n.d. | 26 | 3 | 98 | 8 |
| 553 guAGGcGAGuAucAGAGGAdTsdT | 976 UCCUCUGAuACUCgCCuACdTsdT | n.d. | n.d. | n.d. | n.d. | 23 | 1 | 99 | 11 |
| 526 agGAAAGAcuAAcuucuuudTsdT | 975 AAAGAAGUuAGUCuUUCCUdTsdT | n.d. | n.d. | n.d. | n.d. | 20 | 1 | 102 | 6 |
| 508 ucuucuUAuuGAcAcuuAcdTsdT | 980 GuAAGUGUcAAuAaGAAGAdTsdT | n.d. | n.d. | n.d. | n.d. | 21 | 1 | 102 | 13 |
| 477 uucuGAAAuGuAuAGucuudTsdT | 979 AaGACuAuAcAUUucAGAAdTsdT | n.d. | n.d. | n.d. | n.d. | 25 | 3 | 104 | 16 |
| 497 ucccAuGuucuGGcuuucudTsdT | 977 AgAAAGCcAGAAcaUGGGAdTsdT | n.d. | n.d. | n.d. | n.d. | 43 | 2 | 106 | 8 |
| 501 cuucuuAuuGAcAcuuAcAdTsdT | 981 UguAAGUGUcAAuaAGAAGdTsdT | n.d. | n.d. | n.d. | n.d. | 66 | 14 | 111 | 14 |
| 476 gaAGGAAAGAcuAAcuucudTsdT | 982 AgAAGUuAGUCUUuCCUUCdTsdT | n.d. | n.d. | n.d. | n.d. | 23 | 4 | 111 | 13 |
| 507 ucuucuuAuuGAcAcuuAcdTsdT | 980 GuAAGUGUcAAuAaGAAGAdTsdT | n.d. | n.d. | n.d. | n.d. | 21 | 5 | 115 | 15 |
| 507 ucuucuuAuuGAcAcuuAcdTsdT | 841 pGUAAGUGUcAAuAAGAAGAdTsdT | 7 | 2 | 11 | 2 | 2 | 0 | 45 | 2 |
| 477 uucuGAAAuGuAuAGucuudTsdT | 839 pAAGACuAuAcAUUucAGAAdTsdT | 10 | 1 | 12 | 2 | 8 | 1 | 43 | 4 |
| 501 cuucuuAuuGAcAcuuAcAdTsdT | 842 pUGuAAGUGUcAAuAAGAAGdTsdT | 12 | 1 | 14 | 0 | 8 | 2 | 52 | 6 |
| 469 AguccAAcAGAGAAuucuudTsdT | 742 pAAGAAUUCUCUGUUGGACUdTsdT | 11 | 1 | 14 | 0 | 8 | 0 | 38 | 4 |
| 475 GaAGGAAAGAcuAAcuucudTsdT | 884 pAGAAGUuAGUCUUUCCUUCdTsdT | 10 | 1 | 14 | 0 | 7 | 1 | 48 | 5 |
| 522 cauuGAAAcGAuGccuuGudTsdT | 845 pACAAGGcAUCGUUUcAAUGdTsdT | 11 | 2 | 14 | 2 | n.d. | n.d. | n.d. | n.d. |
| 525 AgGAAAGAcuAAcuucuuudTsdT | 885 pAAAGAAGUuAGUCUUUCCUdTsdT | 12 | 2 | 15 | 1 | 8 | 1 | 44 | 6 |
| 497 ucccAuGuucuGGcuuucudTsdT | 711 pAGAAAGCcAGAAcAUGGGAdTsdT | 12 | 1 | 15 | 2 | 6 | 1 | 71 | 5 |
| 471 uaGGcGAGuAucAGAGGAudTsdT | 892 pAUCCUCUGAuACUCGCCuAdTsdT | 14 | 1 | 16 | 1 | n.d. | n.d. | n.d. | n.d. |
| 552 GuAGGcGAGuAucAGAGGAdTsdT | 891 pUCCUCUGAuACUCGCCuACdTsdT | 14 | 2 | 16 | 1 | 10 | 0 | 51 | 5 |
| 494 GgAuAGAAcAGGAGuuccudTsdT | 866 pAGGAACUCCUGUUCuAUCCdTsdT | 17 | 1 | 16 | 1 | n.d. | n.d. | n.d. | n.d. |
| 473 uguucAAAcAccuGGuAcAdTsdT | 863 pUGuACcAGGUGUUUGAAcAdTsdT | 17 | 1 | 16 | 0 | n.d. | n.d. | n.d. | n.d. |
| 560 cuuccAAAuuGccAuGGAAdTsdT | 838 pUUCcAUGGcAAUUUGGAAGdTsdT | 16 | 2 | 16 | 1 | n.d. | n.d. | n.d. | n.d. |
| 544 GccAuuGAAAcGAuGccuudTsdT | 718 pAAGGcAUCGUUUcAAUGGCdTsdT | 13 | 2 | 17 | 1 | n.d. | n.d. | n.d. | n.d. |
| 493 ugAuGuucAAAcAccuGGudTsdT | 861 pACcAGGUGUUUGAAcAUcAdTsdT | 21 | 1 | 17 | 1 | n.d. | n.d. | n.d. | n.d. |
| 481 AaAuGuAuAGcuucucuuAdTsdT | 714 pAUAAGAAGACuAuAcAUUUdTsdT | 14 | 1 | 17 | 1 | n.d. | n.d. | n.d. | n.d. |
| 488 AuuGcAcucuAAuGAAGcAdTsdT | 735 pUGCUUcAUuAGAGUGcAAUdTsdT | 13 | 1 | 18 | 2 | n.d. | n.d. | n.d. | n.d. |
| 532 GaGAAAGAGAGuAGGcGAGudTsdT | 887 pACUCGCCuACUCUCUUUCUdTsdT | 18 | 2 | 18 | 1 | n.d. | n.d. | n.d. | n.d. |
| 535 uuAuGcuGGAAcuGGGuuudTsdT | 881 pAAACCcAGUUCcAGcAuAAdTsdT | 19 | 2 | 18 | 1 | n.d. | n.d. | n.d. | n.d. |
| 467 uuGuGGcAGAcAGAcuuAudTsdT | 737 pAUAAGUCUGUCUGCcAcAAdTsdT | 22 | 0 | 19 | 1 | n.d. | n.d. | n.d. | n.d. |
| 489 uuAucAAuGcuGuucGGAudTsdT | 728 pAUCCGAAcAGcAUUGAuAAdTsdT | 15 | 1 | 19 | 1 | n.d. | n.d. | n.d. | n.d. |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 480 cccAuuuGAcuuuAuGGAGdTsdT | 739 pCUCcAuAAAGUcAAAUGGGdTsdT | 13 | 1 | 19 | 1 | n.d. | n.d. | n.d. | n.d. |
| 533 AgAcuuAuGcuGGAAcuGGdTsdT | 879 pCCAGUUCcAGcAuAAGUCUdTsdT | 14 | 2 | 19 | 2 | n.d. | n.d. | n.d. | n.d. |
| 582 AucuGGcAGAuGuAuAAGAdTsdT | 825 pUCUuAuAcAUCUGCcAGAUdTsdT | 19 | 3 | 19 | 1 | n.d. | n.d. | n.d. | n.d. |
| 495 AauAuuucAcuGGAAGGAAdTsdT | 741 pUUCCUUCcAGUGAAAuAUUdTsdT | 16 | 1 | 19 | 2 | n.d. | n.d. | n.d. | n.d. |
| 534 uuAcAGAAGcccGcuGuuudTsdT | 831 pAAAcAGCGGGCUUCUGuAAdTsdT | 23 | 2 | 20 | 3 | n.d. | n.d. | n.d. | n.d. |
| 487 AuAGucuucuuAuuGAcAcdTsdT | 715 pGUGUcAAuAAGAAGACuAUdTsdT | 19 | 1 | 20 | 3 | n.d. | n.d. | n.d. | n.d. |
| 521 GauuAcAGAAGcccGcuGudTsdT | 712 pACAGCGGGCUUCUGuAAUCdTsdT | 19 | 2 | 20 | 1 | n.d. | n.d. | n.d. | n.d. |
| 663 ugAAGuGuuAccAAcuAGcdTsdT | 743 pGCuAGUUGGuAAcACUUcAdTsdT | 29 | 5 | 20 | 1 | n.d. | n.d. | n.d. | n.d. |
| 578 uaucAAuGcuGuucGGAuAdTsdT | 865 puAUCCGAAcAGcAUUGAuAdTsdT | 19 | 3 | 20 | 2 | n.d. | n.d. | n.d. | n.d. |
| 482 uacAuuGAGuuuGuGGcAGdTsdT | 875 pCUGCcAcAAACUcAAUGuAdTsdT | 15 | 1 | 20 | 2 | n.d. | n.d. | n.d. | n.d. |
| 528 GacAAuGGcAGucuuGGcudTsdT | 755 pAGCcAAGACUGCcAUUGUCdTsdT | 20 | 2 | 21 | 3 | n.d. | n.d. | n.d. | n.d. |
| 479 ugcAcucuAAuGAAGcAAudTsdT | 871 pAUUGCUUcAUuAGAGUGcAdTsdT | 15 | 1 | 21 | 1 | n.d. | n.d. | n.d. | n.d. |
| 559 uaccAuGAuAucuGGcAGAdTsdT | 821 pUCUGCcAGAuAUcAUGGuAdTsdT | 23 | 2 | 21 | 2 | n.d. | n.d. | n.d. | n.d. |
| 481 AaAuGuAuAGucuucuuAudTsdT | 939 pAuAAGAAGACuAuAcAUUUdTsdT | 18 | 2 | 21 | 1 | n.d. | n.d. | n.d. | n.d. |
| 484 GaAcAGGAGuuccucAcuGdTsdT | 868 pcAGUGAGGAACUCCUGUUCdTsdT | 28 | 1 | 21 | 1 | n.d. | n.d. | n.d. | n.d. |
| 498 uucGGAuAGAAcAGGAGuudTsdT | 734 pAACUCCUGUUCuAUCCGAAdTsdT | 18 | 1 | 21 | 1 | n.d. | n.d. | n.d. | n.d. |
| 512 GaAAcGAGGAcuGAuGccudTsdT | 852 pAGGcAUcAGUCCUCGUUUCdTsdT | 17 | 2 | 21 | 2 | n.d. | n.d. | n.d. | n.d. |
| 491 cauuGAGuuuGuGGcAGAcdTsdT | 876 pGUCUGCcAcAAACUcAAUGdTsdT | 17 | 1 | 21 | 2 | n.d. | n.d. | n.d. | n.d. |
| 485 AucccAuGuucuGGcuuucdTsdT | 710 pGAAAGCcAGAAcAUGGGAUdTsdT | 12 | 1 | 22 | 2 | n.d. | n.d. | n.d. | n.d. |
| 516 AgGcGAGuAucAGAGGAuGdTsdT | 893 pcAUCCUCUGAuACUCGCCUdTsdT | 21 | 2 | 22 | 2 | n.d. | n.d. | n.d. | n.d. |
| 518 AacAuuGuuuGuAcucAcAdTsdT | 913 pUGUGAGuAcAAAcAAUGUUdTsdT | 27 | 2 | 22 | 2 | n.d. | n.d. | n.d. | n.d. |
| 502 uacAGAAGcccGcuGuuucdTsdT | 832 pGAAAcAGCGGGCUUCUGuAdTsdT | 23 | 1 | 22 | 1 | n.d. | n.d. | n.d. | n.d. |
| 504 AuAGAAcAGGAGuuccucAdTsdT | 867 pUGAGGAACUCCUGUUCuAUdTsdT | 23 | 1 | 22 | 2 | n.d. | n.d. | n.d. | n.d. |
| 561 AccGcGAGGAGGAucuuccdTsdT | 818 pGGAAGAUCCUCCUCGCGGUdTsdT | 21 | 2 | 22 | 5 | n.d. | n.d. | n.d. | n.d. |
| 529 AuGccuuGuGucAAGAAGAdTsdT | 846 pUCUUCUUGAcAcAAGGcAUdTsdT | 19 | 2 | 22 | 0 | n.d. | n.d. | n.d. | n.d. |
| 568 uuGccuGAuGuucAAAcAcdTsdT | 858 pGUGUUUGAAcAUcAGGcAAdTsdT | 31 | 3 | 22 | 1 | n.d. | n.d. | n.d. | n.d. |
| 597 AuuAcAGAAGcccGcuGuudTsdT | 830 pAAcAGCGGGCUUCUGuAAUdTsdT | 23 | 3 | 23 | 2 | n.d. | n.d. | n.d. | n.d. |
| 510 AguAccAuGAuAucuGGcAdTsdT | 820 pUGCcAGAuAUcAUGGuACUdTsdT | 26 | 2 | 23 | 2 | n.d. | n.d. | n.d. | n.d. |
| 633 uuAccAuAGcAGuGAcAAudTsdT | 754 pAUUGUcACUGCuAUGGuAAdTsdT | 20 | 4 | 23 | 1 | n.d. | n.d. | n.d. | n.d. |
| 564 AgGGAAuuucucuucAAuGdTsdT | 716 pcAUUGAAGAGAAAUUCCCUdTsdT | 22 | 2 | 23 | 1 | n.d. | n.d. | n.d. | n.d. |
| 515 AguAGAGAAcccAuuuGAcdTsdT | 738 pGUcAAAuGGGuUCUcUACdTsdT | 20 | 2 | 23 | 3 | n.d. | n.d. | n.d. | n.d. |
| 523 AcuuAuGcuGGAAcuGGGudTsdT | 880 pACCcAGUUCcAGcAuAAGUdTsdT | 20 | 2 | 23 | 2 | n.d. | n.d. | n.d. | n.d. |
| 490 AgAAAcGAGGAcuGAuGccdTsdT | 851 pGGcAUcAGUCCUCGUUUCdTsdT | 20 | 1 | 23 | 2 | n.d. | n.d. | n.d. | n.d. |
| 545 AgccucAcuGcuucAAcGcdTsdT | 758 pGCGUUGAAGcAGUGAGGCUdTsdT | 23 | 2 | 23 | 1 | n.d. | n.d. | n.d. | n.d. |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 599 caGuGAcAAuGGcAGucuudTsdT | 904 pAAGACUGCcAUUGUcACUGdTsdT | 26 | 3 | 23 | 2 | n.d. | n.d. | n.d. | n.d. |
| 539 caGccucAcuGcuucAAcGdTsdT | 908 pCGUUGAAGcAGUGAGGCUGdTsdT | 25 | 2 | 23 | 2 | n.d. | n.d. | n.d. | n.d. |
| 521 GauuAcAGAAGcccGcuGudTsdT | 938 pAcAGCGGGCUUCUGuAAUCdTsdT | 22 | 1 | 23 | 1 | n.d. | n.d. | n.d. | n.d. |
| 573 AauuAcAAuGcuGuucGGdTsdT | 727 pCCGAAcAGcAUUGAuAAUUdTsdT | 20 | 3 | 24 | 2 | n.d. | n.d. | n.d. | n.d. |
| 505 cuGGcAcuuuAcAAAcAAAdTsdT | 910 pUUUGUUUGuAAAGUGCcAGdTsdT | 32 | 1 | 24 | 2 | n.d. | n.d. | n.d. | n.d. |
| 585 ccAuGAuAucuGGcAGAuGdTsdT | 823 pcAUCUGCcAGAuAUcAUGGdTsdT | 23 | 3 | 25 | 1 | n.d. | n.d. | n.d. | n.d. |
| 531 uaccucAcAAccAGuccuGdTsdT | 745 pcAGGACUGGUUGUGAGGuAdTsdT | 25 | 2 | 25 | 3 | n.d. | n.d. | n.d. | n.d. |
| 574 GccuGAuGuucAAAcAccudTsdT | 859 pAGGUGUUUGAAcAUcAGGCdTsdT | 21 | 3 | 25 | 1 | n.d. | n.d. | n.d. | n.d. |
| 492 AcAuucAGcAcuGGGAAucdTsdT | 708 pGAUUCCcAGUGCUGAAUGUdTsdT | 17 | 1 | 25 | 2 | n.d. | n.d. | n.d. | n.d. |
| 513 AaGAGAGuAGGcGAGuAucdTsdT | 888 pGAuACUCGCcuACUCUCUUdTsdT | 21 | 2 | 25 | 4 | n.d. | n.d. | n.d. | n.d. |
| 474 GgGuGAcccuuuAGuGAGcdTsdT | 756 pGCUcACuAAAGGGUcACCCdTsdT | 24 | 1 | 25 | 2 | n.d. | n.d. | n.d. | n.d. |
| 598 GaGuAGGcGAGuAucAGAGdTsdT | 890 pCUCUGAuACUCGCCuACUCdTsdT | 23 | 3 | 25 | 1 | n.d. | n.d. | n.d. | n.d. |
| 496 AauAAAcAuuGuuuGuAcudTsdT | 911 pAGuAcAAAcAAUGUUuAUUdTsdT | 25 | 1 | 25 | 2 | n.d. | n.d. | n.d. | n.d. |
| 506 ucuAAuGAAGcAAuAcAuudTsdT | 872 pAAUGuAUUGCUUcAUuAGAdTsdT | 22 | 1 | 26 | 1 | n.d. | n.d. | n.d. | n.d. |
| 500 uuuAuAGuGcuGGuAGuAucdTsdT | 746 pGAuACuAccAGcACuAuAAdTsdT | 28 | 1 | 26 | 1 | n.d. | n.d. | n.d. | n.d. |
| 583 uauAGuGcuGGuAGuAucAdTsdT | 747 pUGAuACuAccAGcACuAuAdTsdT | 26 | 3 | 26 | 1 | n.d. | n.d. | n.d. | n.d. |
| 563 AuGuucAAAcAccuGGuAcdTsdT | 862 pGUACcAGGuGUUUGAAcAUdTsdT | 20 | 2 | 26 | 2 | n.d. | n.d. | n.d. | n.d. |
| 468 ccuGAuGuucAAAcAccuGdTsdT | 860 pcAGGUGUUUGAAcAUcAGGdTsdT | 18 | 0 | 27 | 2 | n.d. | n.d. | n.d. | n.d. |
| 587 uucAAuGccAuuGAAAcGAdTsdT | 844 pUCGUUUcAAUGGcAUUGAAdTsdT | 27 | 3 | 27 | 2 | n.d. | n.d. | n.d. | n.d. |
| 550 uucAGAGuAGAGAAcccAudTsdT | 882 pAUGGGUUCUCuACUCUGAAdTsdT | 25 | 2 | 27 | 2 | n.d. | n.d. | n.d. | n.d. |
| 575 cauAGcAGuGAcAAuGGcAdTsdT | 902 pUGCcAUUGUcACUGCuAUGdTsdT | 33 | 3 | 28 | 1 | n.d. | n.d. | n.d. | n.d. |
| 624 AgcAAGAccGcGAGGAGGAdTsdT | 814 pUCCUCCUCGCGGUCUUGCUdTsdT | 29 | 4 | 28 | 4 | n.d. | n.d. | n.d. | n.d. |
| 627 uuuAuAGuGcuGGuAGuAudTsdT | 900 pAUACuAccAGcACuAuAAAdTsdT | 30 | 4 | 28 | 3 | n.d. | n.d. | n.d. | n.d. |
| 613 caGAuuAcAGAAGcccGcudTsdT | 829 pAGCGGGCUUCUGuAAUCUGdTsdT | 27 | 3 | 29 | 2 | n.d. | n.d. | n.d. | n.d. |
| 507 ucuucuuAuuGAcAcuuAcdTsdT | 949 pGuAAGUGUcAAuAAGAAGAdTsdT | 18 | 2 | 29 | 2 | n.d. | n.d. | n.d. | n.d. |
| 509 uguucGGAuAGAAcAGGAGdTsdT | 733 pCUCCUGUUCuAUCCGAAcAdTsdT | 18 | 2 | 30 | 4 | n.d. | n.d. | n.d. | n.d. |
| 530 GccucAcuGcuucAAcGcAdTsdT | 909 pUGCGUUGAAGcAGUGAGGCdTsdT | 28 | 2 | 30 | 5 | n.d. | n.d. | n.d. | n.d. |
| 483 caAuAcAuuGAGuuuGuGGdTsdT | 874 pCCAcAAACUcAAUGuAUUGdTsdT | 19 | 1 | 30 | 1 | n.d. | n.d. | n.d. | n.d. |
| 519 GauGGGAGuGAuGucAAGudTsdT | 896 pACUUGAcAUcACUCCcAUCdTsdT | 26 | 2 | 30 | 2 | n.d. | n.d. | n.d. | n.d. |
| 537 ucAAuGccAuuGAAAcGAudTsdT | 717 pAUCGUUUcAAUGGcAUUGAdTsdT | 31 | 2 | 30 | 2 | n.d. | n.d. | n.d. | n.d. |
| 511 caGAGAuGAGGGuuuAcAcdTsdT | 856 pGUGuAAACCCUcAUCUCUGdTsdT | 23 | 2 | 30 | 3 | n.d. | n.d. | n.d. | n.d. |
| 620 caGcAAGAccGcGAGGAGGdTsdT | 707 pCCUCCUCGCGGUCUUGCUGdTsdT | 30 | 4 | 31 | 4 | n.d. | n.d. | n.d. | n.d. |
| 595 AccucAcAAccAGuccuGudTsdT | 899 pACAGGACUGGUUGUGAGGUdTsdT | 31 | 3 | 31 | 1 | n.d. | n.d. | n.d. | n.d. |
| 668 caGAAGcccGcuGuuucuAdTsdT | 833 puAGAAAcAGCGGGCUUCUGdTsdT | 32 | 6 | 32 | 3 | n.d. | n.d. | n.d. | n.d. |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 577 AguGcuGGuAGuAucAccudTsdT | 749 pAGGUGAuACuACcAGcACUdTsdT | 28 | 3 | 32 | 2 | n.d. | n.d. | n.d. | n.d. |
| 654 AgAGuAGGcGAGuAucAGAdTsdT | 889 pUCUGAuACUCGCcUACUCUdTsdT | 48 | 5 | 33 | 1 | n.d. | n.d. | n.d. | n.d. |
| 546 GgcAGAcAGAcuuAuGcuGdTsdT | 878 pcAGcAuAAGUCUGUCUGCCdTsdT | 21 | 2 | 33 | 3 | n.d. | n.d. | n.d. | n.d. |
| 622 uuAccuuGGAuGcuGAcuudTsdT | 897 pAAGUcAGcAUCcAAGGuAAdTsdT | 50 | 4 | 33 | 2 | n.d. | n.d. | n.d. | n.d. |
| 541 GgcuGuGAcuuAccAuAGcdTsdT | 751 pGCuAUGGuAAGUcAcAGCCdTsdT | 21 | 2 | 33 | 2 | n.d. | n.d. | n.d. | n.d. |
| 566 GauGAGGGuuuAcAcuGuGdTsdT | 857 pcAcAGUGuAAACCCUcAUCdTsdT | 33 | 2 | 34 | 2 | n.d. | n.d. | n.d. | n.d. |
| 503 GuGAcccuuuAGuGAGcuudTsdT | 907 pAAGCUcACuAAAGGGUcACdTsdT | 25 | 1 | 34 | 2 | n.d. | n.d. | n.d. | n.d. |
| 527 caAGAccGcGAGGAGGAucdTsdT | 816 pGAUCCUCCUCGCGGUCUUGdTsdT | 29 | 2 | 35 | 8 | n.d. | n.d. | n.d. | n.d. |
| 589 cuAuGGcuuccAAAuuGccdTsdT | 837 pGGcAAUUUGGAAGCcAuAGdTsdT | 23 | 3 | 36 | 3 | n.d. | n.d. | n.d. | n.d. |
| 643 GuGcuGGuAGuAucAccuudTsdT | 750 pAAGGUGAuACuACcAGcACdTsdT | 37 | 4 | 37 | 2 | n.d. | n.d. | n.d. | n.d. |
| 600 GgccuuGcGcuGGAuuGGGdTsdT | 849 pCCcAAUCcAGCGcAAGGCCdTsdT | 27 | 3 | 38 | 2 | n.d. | n.d. | n.d. | n.d. |
| 572 AuGcuGuucGGAuAGAAcAdTsdT | 730 pUGUUCuAUCCGAAcAGcAUdTsdT | 32 | 3 | 38 | 1 | n.d. | n.d. | n.d. | n.d. |
| 517 uaGAcuAAGcAuGuAAuuudTsdT | 784 pAAAUuAcAUGCUuAGUCuAdTsdT | 32 | 2 | 39 | 3 | n.d. | n.d. | n.d. | n.d. |
| 611 GgcuGGcuGuGAcuuAccAdTsdT | 901 pUGGuAAGUcAcAGCcAGCCdTsdT | 38 | 3 | 40 | 2 | n.d. | n.d. | n.d. | n.d. |
| 540 ucuuGGcuuuAAAGuGAGGdTsdT | 905 pCCUcACUUuAAAGCcAAGAdTsdT | 23 | 2 | 40 | 2 | n.d. | n.d. | n.d. | n.d. |
| 536 AuAAAcAuuGuuuGuAcucdTsdT | 912 pGAGuAcAAAcAAUGUUuAUdTsdT | 50 | 2 | 40 | 4 | n.d. | n.d. | n.d. | n.d. |
| 524 GucGAcAAGGAGAAcAcGcdTsdT | 705 pGCGUGUUCUCCUUGUCGACdTsdT | 32 | 2 | 41 | 3 | n.d. | n.d. | n.d. | n.d. |
| 551 AaAcGAGGAcuGAuGccuGdTsdT | 724 pcAGGcAUcAGUCCUCGUUUdTsdT | 26 | 2 | 42 | 4 | n.d. | n.d. | n.d. | n.d. |
| 601 uucuuAuuGAcAcuuAcAudTsdT | 843 pAUGuAAGUGUcAAuAAGAAdTsdT | 31 | 3 | 43 | 3 | n.d. | n.d. | n.d. | n.d. |
| 586 uuAAAcuuGuGuAGAcuAAdTsdT | 777 pUUAGUcUAcAcAAGUUuAAdTsdT | 37 | 3 | 43 | 4 | n.d. | n.d. | n.d. | n.d. |
| 616 GuGAcuuAccAuAGcAGuGdTsdT | 753 pcACUGCuAUGGuAAGUcACdTsdT | 24 | 4 | 43 | 4 | n.d. | n.d. | n.d. | n.d. |
| 472 GgcGAGuAucAGAGGAuGGdTsdT | 894 pCCAUCCUCUGAuACUCGCCdTsdT | 26 | 1 | 44 | 2 | n.d. | n.d. | n.d. | n.d. |
| 570 uauAucccAuGuucuGGcudTsdT | 828 pAGCcAGAAcAUGGGAuAuAdTsdT | 28 | 3 | 44 | 8 | n.d. | n.d. | n.d. | n.d. |
| 655 GcAGuGAcAAuGGcAGucudTsdT | 903 pAGACUGCcAUUGUcACUGCdTsdT | 34 | 5 | 44 | 2 | n.d. | n.d. | n.d. | n.d. |
| 671 uucAAAcAccuGGuAcAcAdTsdT | 864 pUGUGuAccAGGUGUUUGAAdTsdT | 59 | 6 | 44 | 4 | n.d. | n.d. | n.d. | n.d. |
| 580 AauGcuGuucGGAuAGAAcdTsdT | 729 pGUUCuAUCCGAAcAGcAUUdTsdT | 31 | 3 | 44 | 1 | n.d. | n.d. | n.d. | n.d. |
| 618 ugGcAGAuGuAuAAGAAGGdTsdT | 826 pCCUUCUuAuAcAUCUGCcAdTsdT | 36 | 4 | 44 | 7 | n.d. | n.d. | n.d. | n.d. |
| 478 cuGuGuAGcuAccucAcAAdTsdT | 744 pUUGUGAGGuAGCuAcAcAGdTsdT | 24 | 1 | 46 | 3 | n.d. | n.d. | n.d. | n.d. |
| 533 AgAcuuAuGcuGGAAcuGGdTsdT | 954 pCcAGUUCcAGcAuAAGUCUdTsdT | 26 | 1 | 46 | 3 | n.d. | n.d. | n.d. | n.d. |
| 605 GuAAGuuAAAcuuGuGuAGdTsdT | 775 pCUAcAcAAGUUuAACUuACdTsdT | 44 | 3 | 46 | 3 | n.d. | n.d. | n.d. | n.d. |
| 571 uuGuGuAGAcuAAGcAuGudTsdT | 781 pACAUGCUuAGUCuAcAcAAdTsdT | 47 | 3 | 47 | 2 | n.d. | n.d. | n.d. | n.d. |
| 557 uguGGcAGAcAGAcuuAuGdTsdT | 877 pcAuAAGUCUGUCUGCcAcAdTsdT | 31 | 2 | 47 | 7 | n.d. | n.d. | n.d. | n.d. |
| 467 uuGuGGcAGAcAGAcuuAudTsdT | 940 pAuAAGUCUGUCUGCcAcAAdTsdT | 86 | 15 | 47 | 5 | n.d. | n.d. | n.d. | n.d. |
| 579 GacuAAAGuAAGuuAAAcudTsdT | 772 pAGUUuAACUuACUUuAGUCdTsdT | 32 | 3 | 47 | 2 | n.d. | n.d. | n.d. | n.d. |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 543 cgcGAGGAGGAucuuccAGdTsdT | 819 pCUGGAAGAUCCUCCUCGCGdTsdT | 52 | 2 | 48 | 7 | n.d. | n.d. | n.d. | n.d. |
| 547 GuGAcuAAAGuAAGuuAAAdTsdT | 770 pUUuAACUuACUUuAGUcACdTsdT | 39 | 2 | 48 | 2 | n.d. | n.d. | n.d. | n.d. |
| 602 uucAcuAAGuGAcuAAAGudTsdT | 765 pACUUuAGUcACUuAGUGAAdTsdT | 39 | 3 | 49 | 4 | n.d. | n.d. | n.d. | n.d. |
| 628 GcAAGAccGcGAGGAGGAudTsdT | 815 pAUCCUCCUCGCGGUCUUGCdTsdT | 36 | 4 | 49 | 3 | n.d. | n.d. | n.d. | n.d. |
| 571 uuGuGuAGAcuAAGcAuGudTsdT | 945 pAcAUGCUuAGUCuAcAcAAdTsdT | 59 | 3 | 50 | 4 | n.d. | n.d. | n.d. | n.d. |
| 562 GaAAuGuAuAGucuuccuuAdTsdT | 713 puAAGAAGACuAuAcAUUUCdTsdT | 49 | 2 | 51 | 6 | n.d. | n.d. | n.d. | n.d. |
| 593 GcGAGuAucAGAGGAuGGGdTsdT | 895 pCCcAUCCUCUGAuACUCGCdTsdT | 27 | 3 | 52 | 5 | n.d. | n.d. | n.d. | n.d. |
| 538 AuAGGcuGGuAGAucAcdTsdT | 748 pGUGAuACUAccAGcACuAUdTsdT | 57 | 2 | 52 | 3 | n.d. | n.d. | n.d. | n.d. |
| 666 AgAccGcGAGGAGGAucuudTsdT | 817 pAAGAUCCUCCUCGCGGUCUdTsdT | 52 | 6 | 52 | 15 | n.d. | n.d. | n.d. | n.d. |
| 567 uguGuGAGuuAAuucAuuudTsdT | 922 pAAAUGAAUuAACUcAcAcAdTsdT | 48 | 2 | 53 | 4 | n.d. | n.d. | n.d. | n.d. |
| 629 ucuAuGGcuuccAAAuuGcdTsdT | 836 pGCAAUUUGGAAGCcAuAGAdTsdT | 63 | 4 | 53 | 3 | n.d. | n.d. | n.d. | n.d. |
| 590 AaGuAcuAAAGuAAGuuAdTsdT | 769 puAACUuACUUuAGUcACUUdTsdT | 62 | 3 | 53 | 7 | n.d. | n.d. | n.d. | n.d. |
| 681 uaAAcuuGuGuAGAcuAAGdTsdT | 778 pCUuAGUCuAcAcAAGUUuAdTsdT | 52 | 7 | 53 | 3 | n.d. | n.d. | n.d. | n.d. |
| 703 AguAAGuuAAAcuuGuGuAGdTsdT | 774 puAcAcAAGUUuAACUuACUdTsdT | 50 | 13 | 54 | 2 | n.d. | n.d. | n.d. | n.d. |
| 603 GuGuGAGuuAAuucAuuuAdTsdT | 791 puAAAUGAAUuAACUcAcACdTsdT | 46 | 3 | 54 | 8 | n.d. | n.d. | n.d. | n.d. |
| 642 uauuGuuAccAAAGuuAAdTsdT | 803 pUUAACUuAGGuAAcAAuAdTsdT | 44 | 4 | 55 | 6 | n.d. | n.d. | n.d. | n.d. |
| 674 cacuAAGuGAcuAAAGuAAdTsdT | 942 pUuACUUuAGUcACUuAGUGdTsdT | 51 | 3 | 55 | 2 | n.d. | n.d. | n.d. | n.d. |
| 569 AaAcuuGuGuAGAcuAAGcdTsdT | 779 pGCUuAGUCuAcAcAAGUUUdTsdT | 60 | 3 | 56 | 3 | n.d. | n.d. | n.d. | n.d. |
| 636 uguuAAGuGGuGAAAucAAdTsdT | 918 pUUGAUUUcACcACUuAAcAdTsdT | 38 | 4 | 56 | 3 | n.d. | n.d. | n.d. | n.d. |
| 659 ugGuuucuAcAccAAAuAcdTsdT | 941 pGuAUUUGGUGuAGAAAccAdTsdT | 51 | 4 | 56 | 8 | n.d. | n.d. | n.d. | n.d. |
| 588 AgAAAGcuGAGAcAuuGcAdTsdT | 925 pUGcAAUGUCUcAGCUUUCUdTsdT | 43 | 3 | 57 | 1 | n.d. | n.d. | n.d. | n.d. |
| 596 AcuAAGuGAcuAAAGuAAGdTsdT | 768 pCUuACUUuAGUcACUuAGUdTsdT | 52 | 3 | 57 | 5 | n.d. | n.d. | n.d. | n.d. |
| 609 uguAGAcuAAGcAuGuAAdTsdT | 783 pAUuAcAUGCUuAGUCuAcAdTsdT | 60 | 3 | 58 | 5 | n.d. | n.d. | n.d. | n.d. |
| 650 uguGuAGAcuAAGcAuGuAdTsdT | 782 puAcAUGCUuAGUCuAcAcAdTsdT | 54 | 5 | 58 | 4 | n.d. | n.d. | n.d. | n.d. |
| 591 ugAcuAAAGuAAGuuAAAcdTsdT | 771 pGUUuAACUuACUUuAGUcAdTsdT | 54 | 3 | 58 | 1 | n.d. | n.d. | n.d. | n.d. |
| 639 AacuuGuGuAGAcuAAGcAdTsdT | 780 pUGCUuAGUCuAcAcAAGUUdTsdT | 57 | 4 | 58 | 2 | n.d. | n.d. | n.d. | n.d. |
| 683 GuuAAAcuuGuGuAGAcuAdTsdT | 776 puAGUCuAcAcAAGUUuAACdTsdT | 55 | 7 | 58 | 3 | n.d. | n.d. | n.d. | n.d. |
| 586 uuAAAcuuGuGuAGAcuAAdTsdT | 944 pUuAGUCuAcAcAAGUUuAAdTsdT | 62 | 6 | 59 | 2 | n.d. | n.d. | n.d. | n.d. |
| 653 GguGAcccuuuAGuGAGcudTsdT | 757 pAGCUcACUAAAGGGUcACCdTsdT | 60 | 5 | 60 | 7 | n.d. | n.d. | n.d. | n.d. |
| 542 GgcuAccuAuGGuGAAcGudTsdT | 722 pACGUUcACcAuAGGuAGCCdTsdT | 30 | 2 | 60 | 6 | n.d. | n.d. | n.d. | n.d. |
| 631 AccAuGAuAucuGGcAGAudTsdT | 822 pAUCUGCcAGAuAUcAUGGUdTsdT | 65 | 4 | 60 | 4 | n.d. | n.d. | n.d. | n.d. |
| 605 GuAAGuuAAAcuuGuGuAGdTsdT | 943 pCuAcAcAAGUUuAACUuACdTsdT | 51 | 3 | 60 | 6 | n.d. | n.d. | n.d. | n.d. |
| 676 AauGuAuAGucuucucuuAuudTsdT | 840 pAAuAAGAAGACuAuAcAUUdTsdT | 62 | 6 | 60 | 8 | n.d. | n.d. | n.d. | n.d. |
| 499 AaGuAGGuuGuGuGAGuuAdTsdT | 790 puAACUcAcAcAACCuACUUdTsdT | 56 | 1 | 60 | 2 | n.d. | n.d. | n.d. | n.d. |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 669 uuuGAcuuuAuGGAGAAuAdTsdT | 883 puAUUCUCCAuAAAGUcAAAdTsdT | 61 | 6 | 60 | 2 | n.d. | n.d. | n.d. | n.d. |
| 677 GaccAcuAAuGGGAGccAAdTsdT | 914 pUUGGCUCCcAUuAGUGGUCdTsdT | 56 | 6 | 60 | 6 | n.d. | n.d. | n.d. | n.d. |
| 627 uuuAuAGuGcuGGuAGuAudTsdT | 957 pAuACuACcAGcACuAuAAAdTsdT | 74 | 9 | 61 | 1 | n.d. | n.d. | n.d. | n.d. |
| 656 AaAcGAuGccuuGuGucAAdTsdT | 719 pUUGAcAcAAGGcAUCGUUUdTsdT | 40 | 5 | 62 | 8 | n.d. | n.d. | n.d. | n.d. |
| 647 GuuAuuGuuAccuAAAGuudTsdT | 801 pAACUUuAGGuAAcAAuAACdTsdT | 63 | 5 | 62 | 14 | n.d. | n.d. | n.d. | n.d. |
| 644 cuGuGAcuuAccAuAGcAGdTsdT | 752 pCUGCuAUGGuAAGUcACAGdTsdT | 30 | 4 | 62 | 6 | n.d. | n.d. | n.d. | n.d. |
| 652 AgGAGcuucuuAAGuuAAAdTsdT | 788 pUUuAACUuAAGAAGCUCCUdTsdT | 61 | 5 | 62 | 4 | n.d. | n.d. | n.d. | n.d. |
| 672 uuGcAcucuAAuGAAGcAAdTsdT | 870 pUUGCUUcAUuAGAGUGcAAdTsdT | 88 | 6 | 63 | 7 | n.d. | n.d. | n.d. | n.d. |
| 682 AguAGGuuGuGuGAGuuAAdTsdT | 920 pUUAACUcAcAcAACCuACUdTsdT | 60 | 7 | 63 | 5 | n.d. | n.d. | n.d. | n.d. |
| 594 GgGccuuGcGcuGGAuuGGdTsdT | 848 pCCAAUCcAGCGcAAGGCCCdTsdT | 32 | 3 | 63 | 5 | n.d. | n.d. | n.d. | n.d. |
| 701 AgAAGcccGcuGuuucuAudTsdT | 834 pAUAGAAAcAGCGGGCUUCUdTsdT | 79 | 11 | 63 | 5 | n.d. | n.d. | n.d. | n.d. |
| 697 ugAccAcuAAuGGGAGccAdTsdT | 763 pUGGCUCCcAUuAGUGGUcAdTsdT | 68 | 9 | 64 | 8 | n.d. | n.d. | n.d. | n.d. |
| 664 AauGAAGcAAuAcAuuGAGdTsdT | 873 pCUcAAUGuAUUGCUUcAUUdTsdT | 63 | 5 | 64 | 4 | n.d. | n.d. | n.d. | n.d. |
| 662 AcucuAAuGAAGcAAuAcAdTsdT | 736 pUGuAUUGCUUcAUuAGAGUdTsdT | 71 | 5 | 64 | 6 | n.d. | n.d. | n.d. | n.d. |
| 659 ugGuuucuAcAccAAAuAcdTsdT | 760 pGUAUUUGGUGuAGAAACCdTsdT | 54 | 5 | 64 | 3 | n.d. | n.d. | n.d. | n.d. |
| 615 AuAAuuAucAAuGcuGuucdTsdT | 726 pGAAcAGcAUUGAuAAUuAdTsdT | 45 | 4 | 65 | 4 | n.d. | n.d. | n.d. | n.d. |
| 558 AgAGAuAAAuGuuGAucuudTsdT | 798 pAAGAUcAAcAUUuAUCUCUdTsdT | 67 | 2 | 65 | 7 | n.d. | n.d. | n.d. | n.d. |
| 651 ugGGccuuGcGcuGGAuuGdTsdT | 847 pcAAUCcAGCGcAAGGCCcAdTsdT | 67 | 5 | 65 | 3 | n.d. | n.d. | n.d. | n.d. |
| 698 GuAGcuAccucAcAAccAGdTsdT | 898 pCUGGUUGUGAGGuAGCuACdTsdT | 61 | 9 | 65 | 2 | n.d. | n.d. | n.d. | n.d. |
| 680 ccAAcuuuAAAGucAGuccdTsdT | 915 pGGACUGACUUuAAAGUUGGdTsdT | 59 | 6 | 65 | 2 | n.d. | n.d. | n.d. | n.d. |
| 645 GaGcuucuuAAGuuAAAucdTsdT | 917 pGAUUuAACUuAAGAAGCUCdTsdT | 59 | 5 | 65 | 2 | n.d. | n.d. | n.d. | n.d. |
| 642 uauuGuuAccuAAAGuuAAdTsdT | 947 pUuAACUUuAGGuAAcAAuAdTsdT | 69 | 4 | 65 | 3 | n.d. | n.d. | n.d. | n.d. |
| 486 GuAGGuuGuGuGAGuuAAudTsdT | 921 pAUuAACUcAcAcAACCuACdTsdT | 61 | 1 | 65 | 4 | n.d. | n.d. | n.d. | n.d. |
| 692 GuuGGuGccAGAuAGAAGAdTsdT | 785 pUCUUCuAUCUGGcACcAACdTsdT | 65 | 8 | 65 | 4 | n.d. | n.d. | n.d. | n.d. |
| 691 GguuucuAcAccAAAuAcAdTsdT | 761 pUGuAUUUGGUGuAGAAACCdTsdT | 63 | 7 | 66 | 6 | n.d. | n.d. | n.d. | n.d. |
| 674 cacuAAGuGAcuAAAGuAAdTsdT | 767 pUUACUUuAGUcACUuAGUGdTsdT | 61 | 6 | 66 | 7 | n.d. | n.d. | n.d. | n.d. |
| 623 AuucAGcAcuGGGAAucccdTsdT | 709 pGGGAUUCCcAGUGCUGAAUdTsdT | 68 | 4 | 66 | 9 | n.d. | n.d. | n.d. | n.d. |
| 581 AgAAuAuuucAcuGGAAGGdTsdT | 740 pCCUUCcAGUGAAAuAUUCUdTsdT | 43 | 3 | 67 | 4 | n.d. | n.d. | n.d. | n.d. |
| 673 uguuAccuAAAGuuAAuccdTsdT | 805 pGGAUuAACUUuAGGuAAcAdTsdT | 70 | 6 | 67 | 9 | n.d. | n.d. | n.d. | n.d. |
| 607 AuGuGAGGAuuAAcuucuGdTsdT | 810 pcAGAAGUuAAUCCUcAcAUdTsdT | 69 | 3 | 67 | 6 | n.d. | n.d. | n.d. | n.d. |
| 686 GuAGuGccuGGGAuucucdTsdT | 787 pGAGAAUCCcAGGAcACuACdTsdT | 72 | 7 | 68 | 4 | n.d. | n.d. | n.d. | n.d. |
| 576 uguGAGuuAuucAuuuAudTsdT | 923 pAUAAAUGAAUuAACUcACAdTsdT | 64 | 3 | 68 | 5 | n.d. | n.d. | n.d. | n.d. |
| 619 AuAGcuuGAuuuAuuuGGudTsdT | 759 pACcAAAuAAAUcAAGCuAUdTsdT | 59 | 4 | 68 | 5 | n.d. | n.d. | n.d. | n.d. |
| 608 uuAAGuGGuGAAAucAAcudTsdT | 919 pAGUUGAUUUcACcACUuAAdTsdT | 62 | 3 | 68 | 9 | n.d. | n.d. | n.d. | n.d. |

TABLE 2-continued

| SEQ ID sense strand sequence NO (5'-3') | SEQ ID antisense strand sequence NO (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|
| | | mRNA [%] | s.d. [%] | mRNA [%] | s.d. [%] | mRNA [%] | s.d. [%] | mRNA [%] | s.d. [%] |
| 682 AguAGGuuGuGuGAGuuAAdTsdT | 958 pUuAACUcAcAcAACCuuACUdTsdT | 75 | 5 | 69 | 5 | n.d. | n.d. | n.d. | n.d. |
| 549 GccuuuAuGuuuGGGAGAAdTsdT | 924 pUUCUCCcAAAcAuAAAGGCdTsdT | 48 | 2 | 69 | 4 | n.d. | n.d. | n.d. | n.d. |
| 520 caGAccAuuuccuAAucAGdTsdT | 937 pCUGAUuAGGAAAUGGUCUGdTsdT | 70 | 2 | 69 | 3 | n.d. | n.d. | n.d. | n.d. |
| 556 GaAuAAuGuGAGGAuuAAcdTsdT | 933 pGUuAAUCCuCAcAUuAUUCdTsdT | 64 | 2 | 70 | 7 | n.d. | n.d. | n.d. | n.d. |
| 679 ugAuGccuGGGccucAcAuudTsdT | 855 pAAUGUGAGGCcAGGcAUcAdTsdT | 72 | 6 | 70 | 8 | n.d. | n.d. | n.d. | n.d. |
| 660 ucucuGuAAuAuGAuAcAAudTsdT | 927 pAUGuAUcAuAUUuAcAGAGdTsdT | 62 | 5 | 70 | 3 | n.d. | n.d. | n.d. | n.d. |
| 694 ucAcuAAGuGAcuAAAGuAdTsdT | 766 puACUUuAGUcACUuAGUGAdTsdT | 68 | 8 | 70 | 5 | n.d. | n.d. | n.d. | n.d. |
| 675 ugccAGAuAGAAGAcAGGudTsdT | 786 pACCUGUCUUCuAUCUGGcAdTsdT | 64 | 6 | 70 | 3 | n.d. | n.d. | n.d. | n.d. |
| 658 ugAGAGAuAAAuGuuGAucdTsdT | 797 pGAUcAAcAUUuAUCUCUcAdTsdT | 70 | 5 | 71 | 9 | n.d. | n.d. | n.d. | n.d. |
| 684 cuGAccAcuAAuGGGAGccdTsdT | 762 pGGCuCCCcAUuAGUGGUcAGdTsdT | 68 | 7 | 72 | 9 | n.d. | n.d. | n.d. | n.d. |
| 625 AgGGcuAcuuuGAAuuAAdTsdT | 796 pAUuAAUUcAAAGuAGCCCUdTsdT | 70 | 4 | 72 | 9 | n.d. | n.d. | n.d. | n.d. |
| 649 AccAcuAAuGGGAGccAAudTsdT | 764 pAUUGGCuCCCcAUuAGUGGUdTsdT | 61 | 5 | 72 | 4 | n.d. | n.d. | n.d. | n.d. |
| 617 uaGGGcuAcuuuGAAuuAAdTsdT | 946 pUuAAUUcAAAGuAGCCCuAdTsdT | 73 | 3 | 72 | 6 | n.d. | n.d. | n.d. | n.d. |
| 606 cgGAAGuuGGAAucAGGuudTsdT | 931 pAACCUGAUUcCAACUUCCGdTsdT | 57 | 3 | 73 | 2 | n.d. | n.d. | n.d. | n.d. |
| 661 GaGAGAuAAAuGuuGAucudTsdT | 926 pAGAUcAAcAUUuAUCUCUCdTsdT | 60 | 5 | 73 | 6 | n.d. | n.d. | n.d. | n.d. |
| 584 GgccAGcAAGAccGcGAGGdTsdT | 706 pCCUCGCGGUCUUGCUGGCCdTsdT | 49 | 3 | 74 | 5 | n.d. | n.d. | n.d. | n.d. |
| 695 uuAuuGuuAccuAAAGuuAdTsdT | 802 puAACUUuAGGuAAcAAuAAdTsdT | 74 | 9 | 74 | 13 | n.d. | n.d. | n.d. | n.d. |
| 576 uguGAGuuAAuucAuuuAudTsdT | 959 pAuAAAUGAAUuAACUcAcAdTsdT | 67 | 4 | 74 | 5 | n.d. | n.d. | n.d. | n.d. |
| 617 uaGGGcuAcuuuGAAuuAAdTsdT | 795 pUUAAUUcAAAGuAGCCCuAdTsdT | 51 | 4 | 74 | 13 | n.d. | n.d. | n.d. | n.d. |
| 635 uaGuGuccuGGGAuucucudTsdT | 916 pAGAGAAUCCcAGGAcACuAdTsdT | 72 | 4 | 74 | 6 | n.d. | n.d. | n.d. | n.d. |
| 687 uaucuGGcAGAuGuAuAAGdTsdT | 824 pCUuAuAcAUCUGCcAGAuAdTsdT | 86 | 7 | 74 | 5 | n.d. | n.d. | n.d. | n.d. |
| 632 GaccAuuuccuAAucAGuudTsdT | 811 pAACUGAUuAGGAAAUGGUCdTsdT | 61 | 4 | 75 | 10 | n.d. | n.d. | n.d. | n.d. |
| 626 uaAGuuAuuGuuAccAAAdTsdT | 799 pUUuAGGuAAcAAuAACUuAdTsdT | 84 | 4 | 75 | 9 | n.d. | n.d. | n.d. | n.d. |
| 667 uuGuuAccuAAAGuuAAucdTsdT | 804 pGAUuAACUUuAGGuAAcAAdTsdT | 76 | 6 | 76 | 9 | n.d. | n.d. | n.d. | n.d. |
| 630 AaAGAcuAAcuucuuuGAGdTsdT | 886 pCUcAAAGAAGuuAGUCUUUdTsdT | 49 | 4 | 76 | 3 | n.d. | n.d. | n.d. | n.d. |
| 621 GacuGAuGccuGGccucAcdTsdT | 854 pGUGAGGCcAGGcAUcAGUCdTsdT | 67 | 4 | 76 | 4 | n.d. | n.d. | n.d. | n.d. |
| 670 uaccuAAAGuuAAuccAGAdTsdT | 807 pUCUGGAUuAACUUuAGGuAdTsdT | 80 | 6 | 76 | 10 | n.d. | n.d. | n.d. | n.d. |
| 634 AauGuGAGGAuuAAcuucudTsdT | 809 pAGAAGUuAAUCCuCAcAUUdTsdT | 69 | 4 | 77 | 2 | n.d. | n.d. | n.d. | n.d. |
| 612 AaGAGGcuAccuAuGGuGAdTsdT | 850 pUCACcAuAGGuAGCCCUCUUdTsdT | 65 | 3 | 78 | 2 | n.d. | n.d. | n.d. | n.d. |
| 678 GuuAccuAAAGuuAAuccAdTsdT | 928 pUGGAUuAACUUuAGGuAAcdTsdT | 73 | 6 | 79 | 5 | n.d. | n.d. | n.d. | n.d. |
| 648 uaAuGuGAGGAuuAAcuucdTsdT | 935 pGAAGUuAAUCCuCAcAUuAdTsdT | 75 | 5 | 80 | 2 | n.d. | n.d. | n.d. | n.d. |
| 689 ucAGAccAuuuccuAAucdTsdT | 936 pUGAUuAGGAAAUGGUCUGAdTsdT | 75 | 7 | 81 | 6 | n.d. | n.d. | n.d. | n.d. |
| 641 ccuAAAGuuAAuccAGAuudTsdT | 929 pAAUCUGGAUuAACUUuAGGdTsdT | 72 | 4 | 81 | 4 | n.d. | n.d. | n.d. | n.d. |
| 555 ucAGcAcuGGGAAucccuGdTsdT | 827 pcAGGGAUUCCcAGUGCUGAdTsdT | 81 | 2 | 82 | 12 | n.d. | n.d. | n.d. | n.d. |

TABLE 2-continued

| SEQ ID NO | sense strand sequence (5'-3') | SEQ ID NO | antisense strand sequence (5'-3') | Activity testing with 50 nM siRNA in HeLaS3 cells, transfection 1 | | Activity testing with 500 pM siRNA in HeLaS3 cells | | Activity testing with 50 nM siRNA in HeLaS3 cells, transfection 2 | | Activity testing with 30 pM siRNA in HeLaS3 cells | |
|---|---|---|---|---|---|---|---|---|---|---|---|
| | | | | mRNA [%] | s.d. [%] | mRNA [%] | s.d. [%] | mRNA [%] | s.d. [%] | mRNA [%] | s.d. [%] |
| 565 | cccuGuuAAGuGGuGAAAAudTsdT | 789 | pAUUUcACcACUuAAcAGGGdTsdT | 76 | 2 | 83 | 4 | n.d. | n.d. | n.d. | n.d. |
| 554 | AaGcccGcuGuuucuAuGGdTsdT | 835 | pCCAuAGAAAcAGCGGGCUUdTsdT | 72 | 2 | 84 | 5 | n.d. | n.d. | n.d. | n.d. |
| 696 | uaGcuGAAuAAuGuGAGGAdTsdT | 808 | pUCCUcAcAUuAUUcAGCuAdTsdT | 84 | 9 | 84 | 11 | n.d. | n.d. | n.d. | n.d. |
| 483 | caAuAcAuuGAGuuuGuGGdTsdT | 953 | pCCAcAAACUcAAUGuAUUGdTsdT | 31 | 2 | 84 | 6 | n.d. | n.d. | n.d. | n.d. |
| 638 | GcGGAAGuuGGAAucAGGudTsdT | 930 | pACCUGAUUCcAACUUCCGCdTsdT | 72 | 4 | 84 | 7 | n.d. | n.d. | n.d. | n.d. |
| 514 | cauuAGcuGAAuAAuGuGAdTsdT | 932 | pUCAcAUuAUUcAGCuAAUGdTsdT | 72 | 2 | 85 | 6 | n.d. | n.d. | n.d. | n.d. |
| 702 | AcuAAAGuAAGuuAAAcuudTsdT | 773 | pAAGUUuAACUuACUUuAGUdTsdT | 87 | 12 | 86 | 6 | n.d. | n.d. | n.d. | n.d. |
| 595 | AccucAcAAccAGuccuGudTsdT | 956 | pAcAGGACUGGUUGUGAGGUdTsdT | 35 | 1 | 86 | 5 | n.d. | n.d. | n.d. | n.d. |
| 472 | GgcGAGuAucAGAGGAuGGdTsdT | 955 | pCCAUCCUCUGAuAUCUGCCdTsdT | 23 | 1 | 87 | 5 | n.d. | n.d. | n.d. | n.d. |
| 690 | uuAccuAAAGuuAAuccAGdTsdT | 806 | pCUGGAUuAACUUuAGGuAAdTsdT | 89 | 7 | 88 | 12 | n.d. | n.d. | n.d. | n.d. |
| 592 | ugcuGuucGGAuAGAAcAGdTsdT | 731 | pCUGUUCuAUCCGAAcAGcAdTsdT | 76 | 3 | 89 | 3 | n.d. | n.d. | n.d. | n.d. |
| 693 | GcuAccuAuGGuGAAcGuGdTsdT | 723 | pcACGUUcACcAuAGGuAGCdTsdT | 77 | 8 | 89 | 7 | n.d. | n.d. | n.d. | n.d. |
| 665 | AcGAuGccuuGuGucAAGAdTsdT | 720 | pUCUUGAcAcAAGGcAUCGUdTsdT | 76 | 6 | 90 | 4 | n.d. | n.d. | n.d. | n.d. |
| 688 | AgGcuAccuAuGGuGAAcGdTsdT | 721 | pCGUUcACcAuAGGuAGCCdTsdT | 90 | 7 | 90 | 8 | n.d. | n.d. | n.d. | n.d. |
| 685 | uauucuuAAuAGGGcuAcudTsdT | 793 | pAGuAGCCCuAUuAAGAAuAdTsdT | 93 | 7 | 90 | 17 | n.d. | n.d. | n.d. | n.d. |
| 701 | AgAAGcccGcuGuuucuAudTsdT | 948 | pAuAGAAAcAGCGGGCUUCUdTsdT | 79 | 3 | 90 | 4 | n.d. | n.d. | n.d. | n.d. |
| 646 | cuGuucGGAuAGAAcAGGAdTsdT | 732 | pUCCUGUUCuAUCCGAAcAGdTsdT | 67 | 5 | 91 | 9 | n.d. | n.d. | n.d. | n.d. |
| 640 | AuucuuAAuAGGGcuAcuudTsdT | 794 | pAAGuAGCCCuAUuAAGAAUdTsdT | 114 | 4 | 92 | 15 | n.d. | n.d. | n.d. | n.d. |
| 548 | AguuAuuGuuAccuAAAGudTsdT | 800 | pACUUuAGGuAAcAAuAACUdTsdT | 67 | 2 | 92 | 10 | n.d. | n.d. | n.d. | n.d. |
| 610 | AuAAuGuGAGGAuuAAcuudTsdT | 934 | pAAGUuAAUCCUcAcAUuAUdTsdT | 90 | 3 | 93 | 6 | n.d. | n.d. | n.d. | n.d. |
| 637 | AcAAAuAuucuuAAuAGGGdTsdT | 792 | pCCCuAUuAAGAAuAUUUGdTsdT | 79 | 4 | 94 | 18 | n.d. | n.d. | n.d. | n.d. |
| 514 | cauuAGcuGAAuAAuGuGAdTsdT | 960 | pUcAcAUuAUUcAGCuAAUGdTsdT | 85 | 4 | 94 | 2 | n.d. | n.d. | n.d. | n.d. |
| 614 | ugAGGccuuGccuGuGAAGdTsdT | 869 | pCUUcAcAGGcAAGGCCUcAdTsdT | 100 | 3 | 95 | 6 | n.d. | n.d. | n.d. | n.d. |
| 563 | AuGuucAAAcAccuGGuAcdTsdT | 952 | pGuACcAGGUGUUUGAAcAUdTsdT | 96 | 9 | 95 | 14 | n.d. | n.d. | n.d. | n.d. |
| 699 | ucccGcucGcGcccAucAcdTsdT | 812 | pGUGAUGGGCGCGAGCGGGAdTsdT | 94 | 10 | 95 | 8 | n.d. | n.d. | n.d. | n.d. |
| 604 | cccGcucGcGcccAucAcGdTsdT | 813 | pCGUGAUGGGCGCGAGCGGGdTsdT | 90 | 3 | 96 | 4 | n.d. | n.d. | n.d. | n.d. |
| 657 | GgAcuGAuGccuGGccucAdTsdT | 853 | pUGAGGCcAGGcAUcAGUCCdTsdT | 87 | 5 | 97 | 8 | n.d. | n.d. | n.d. | n.d. |
| 612 | AaGAGGcuAccuAuGGuGAdTsdT | 951 | pUcACcAuAGGuAGCCUCUUdTsdT | 79 | 9 | 97 | 7 | n.d. | n.d. | n.d. | n.d. |
| 522 | cauuGAAAcGAuGccuuGudTsdT | 950 | pAcAAGGcAUCGUUUcAAUGdTsdT | 93 | 11 | 100 | 6 | n.d. | n.d. | n.d. | n.d. |
| 700 | cuuGGcuuuAAAGuGAGGGdTsdT | 906 | pCCCUcACUUuAAAGCcAAGdTsdT | 90 | 10 | 100 | 7 | n.d. | n.d. | n.d. | n.d. |
| 704 | AauAAuuAucAAuGcuGuudTsdT | 725 | pAAcAGcAUUGAuAAUuAUUdTsdT | 134 | 14 | 101 | 2 | n.d. | n.d. | n.d. | n.d. |

TABLE 3

| SEQ ID NO pair | Activity testing for dose response in HeLaS3 cells, means of two transfections | | | | Activity testing for dose response in HeLaS3 cells, transfection 3 | | | | Activity testing for dose response in HeLaS3 cells, transfection 4 | | | |
|---|---|---|---|---|---|---|---|---|---|---|---|---|
| | mean IC50 [nM] | mean IC80 [nM] | mean IC20 [nM] | mean max. inh [%] | mean IC50 [nM] | mean IC80 [nM] | mean IC20 [nM] | mean max. inh [%] | mean IC50 [nM] | mean IC80 [nM] | mean IC20 [nM] | mean max. inh [%] |
| 469/742 | 0.004 | 0.059 | 0.001 | 91 | 0.013 | 0.124 | 0.002 | 95 | 0.014 | 0.158 | 0.002 | 91 |
| 525/885 | 0.004 | 0.074 | 0.001 | 90 | 0.01 | 0.10 | 0.00 | 92 | n.d. | n.d. | n.d. | n.d. |
| 477/839 | 0.006 | 0.066 | 0.001 | 91 | 0.016 | 0.143 | 0.003 | 93 | 0.013 | 0.198 | 0.002 | 90 |
| 552/891 | 0.006 | 0.107 | 0.001 | 88 | 0.02 | 0.14 | 0.00 | 90 | n.d. | n.d. | n.d. | n.d. |
| 475/884 | 0.006 | 0.073 | 0.001 | 91 | 0.02 | 0.16 | 0.00 | 93 | n.d. | n.d. | n.d. | n.d. |
| 501/842 | 0.007 | 0.091 | 0.001 | 90 | 0.02 | 0.18 | 0.00 | 91 | n.d. | n.d. | n.d. | n.d. |
| 473/863 | 0.009 | 0.330 | 0.002 | 84 | n.d. | n.d. | n.d. | n.d. | n.d. | n.d. | n.d. | n.d. |
| 507/841 | 0.010 | 0.081 | 0.002 | 97 | 0.03 | 0.21 | 0.01 | 97 | n.d. | n.d. | n.d. | n.d. |
| 494/866 | 0.011 | 0.810 | 0.003 | 84 | n.d. | n.d. | n.d. | n.d. | n.d. | n.d. | n.d. | n.d. |
| 544/718 | 0.014 | 0.145 | 0.003 | 92 | n.d. | n.d. | n.d. | n.d. | n.d. | n.d. | n.d. | n.d. |
| 497/711 | 0.015 | 0.116 | 0.003 | 89 | n.d. | n.d. | n.d. | n.d. | n.d. | n.d. | n.d. | n.d. |
| 560/838 | 0.021 | 0.265 | 0.004 | 86 | n.d. | n.d. | n.d. | n.d. | n.d. | n.d. | n.d. | n.d. |
| 522/845 | 0.029 | 0.295 | 0.006 | 90 | n.d. | n.d. | n.d. | n.d. | n.d. | n.d. | n.d. | n.d. |
| 471/892 | 0.029 | 0.361 | 0.005 | 88 | n.d. | n.d. | n.d. | n.d. | n.d. | n.d. | n.d. | n.d. |
| 488/735 | 0.030 | 0.262 | 0.006 | 89 | n.d. | n.d. | n.d. | n.d. | n.d. | n.d. | n.d. | n.d. |
| 507/949 | 0.204 | 2.588 | 0.053 | 82 | n.d. | n.d. | n.d. | n.d. | n.d. | n.d. | n.d. | n.d. |
| 526/967 | n.d. | n.d. | n.d. | n.d. | 0.015 | 0.120 | 0.0016 | 92 | n.d. | n.d. | n.d. | n.d. |
| 470/962 | n.d. | n.d. | n.d. | n.d. | 0.022 | 0.219 | 0.004 | 94 | 0.020 | 0.314 | 0.002 | 90 |
| 553/968 | n.d. | n.d. | n.d. | n.d. | 0.024 | 0.152 | 0.0041 | 89 | n.d. | n.d. | n.d. | n.d. |
| 477/963 | n.d. | n.d. | n.d. | n.d. | 0.024 | 0.189 | 0.005 | 93 | 0.016 | 0.251 | 0.002 | 90 |
| 501/965 | n.d. | n.d. | n.d. | n.d. | 0.036 | 0.281 | 0.0053 | 91 | n.d. | n.d. | n.d. | n.d. |
| 476/966 | n.d. | n.d. | n.d. | n.d. | 0.038 | 0.313 | 0.0062 | 93 | n.d. | n.d. | n.d. | n.d. |
| 507/964 | n.d. | n.d. | n.d. | n.d. | 0.045 | 0.310 | 0.0077 | 97 | n.d. | n.d. | n.d. | n.d. |
| 477/971 | n.d. | n.d. | n.d. | n.d. | 0.154 | 2.062 | 0.034 | 85 | n.d. | n.d. | n.d. | n.d. |
| 470/970 | n.d. | n.d. | n.d. | n.d. | 0.184 | 2.134 | 0.040 | 87 | n.d. | n.d. | n.d. | n.d. |
| 470/978 | n.d. | n.d. | n.d. | n.d. | 0.479 | #N/A | 0.073 | 72 | n.d. | n.d. | n.d. | n.d. |
| 477/979 | n.d. | n.d. | n.d. | n.d. | 0.906 | #N/A | 0.142 | 78 | n.d. | n.d. | n.d. | n.d. |

TABLE 4

| SEQ ID NO pair | Stability Cyno Serum | | Stability Human Serum | | Stability Mouse Serum | | Human PBMC assay | |
|---|---|---|---|---|---|---|---|---|
| | sense t½ [hr] | antisense t½ [hr] | sense t½ [hr] | antisense t½ [hr] | sense t½ [hr] | antisense t½ [hr] | IFN-a | TNF-a |
| 475/884 | 15.8 | 2.2 | >48 | 0.9 | 15.5 | 9.2 | 0 | 0 |
| 507/841 | 16.2 | 0.7 | >48 | 1.7 | 12.1 | 0.6 | 0 | 0 |
| 525/885 | 41.1 | 4.2 | >48 | 2.0 | 13.1 | 7.7 | 0 | 0 |
| 469/742 | 36.4 | 4.7 | >48 | 2.5 | 14.2 | 7.5 | 0 | 0 |
| 552/891 | 13.6 | 9.8 | >48 | 7.1 | 10.3 | 11.6 | 0 | 0 |
| 501/842 | 17.4 | 2.2 | >48 | 11.4 | 13.5 | 3.2 | 0 | 0 |
| 477/839 | 40.8 | 16.8 | >48 | >48 | 27.4 | 10.7 | 0 | 0 |
| 497/711 | >48 | 11.8 | >48 | >48 | >48 | 14.2 | 0 | 0 |

TABLE 5

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 1 | UUGUGGCAGACAGACUUAU | 234 | AUAAGUCUGUCUGCCACAA | 467 | uuGuGGcAGAcAGAcuuAudTsdT | 737 | pAUAAGUCUGUCUGCCAcAAdTsdT |
| 1 | UUGUGGCAGACAGACUUAU | 234 | AUAAGUCUGUCUGCCACAA | 467 | uuGuGGcAGAcAGAcuuAudTsdT | 940 | pAuAAGUCUGUCUGCCAcAAdTsdT |
| 2 | CCUGAUGUUCAAACACCUG | 235 | CAGGUGUUUGAACAUCAGG | 468 | ccuGAuGuucAAAcAccuGdTsdT | 860 | pcAGGUGUUUGAAcAUcAGGdTsdT |
| 3 | AGUCCAACAGAGAAUUCUU | 236 | AAGAAUUCUCUGUUGGACU | 469 | AguccAAcAGAGAAuucuudTsdT | 742 | pAAGAAUUCUCUGUUGGACUdTsdT |
| 3 | AGUCCAACAGAGAAUUCUU | 236 | AAGAAUUCUCUGUUGGACU | 470 | aguccAAcAGAGAAuucuudTsdT | 962 | AAGAAUUCUCUGUUGGACUdTsdT |
| 3 | AGUCCAACAGAGAAUUCUU | 236 | AAGAAUUCUCUGUUGGACU | 470 | aguccAAcAGAGAAuucuudTsdT | 970 | AAGAAUUCUCUGUuGGACUdTsdT |
| 3 | AGUCCAACAGAGAAUUCUU | 236 | AAGAAUUCUCUGUUGGACU | 470 | aguccAAcAGAGAAuucuudTsdT | 978 | AaGAAUUCUCUGUuGGACUdTsdT |
| 4 | UAGGCGAGUAUCAGAGGAU | 237 | AUCCUCUGAUACUCGCCUA | 471 | uaGGcGAGuAucAGAGGAudTsdT | 892 | pAUCCUCUGAuACUCGCCuAdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 5 | GGCGAGUAUCAGAGGAUGG | 238 | CCAUCCUCUGAUAUCUCGCC | 472 | GgcGAGuAucAGAGGAuGGdTsdT | 894 | pCCAUCCUCUGAuAUCUCGCCdTsdT |
| 5 | GGCGAGUAUCAGAGGAUGG | 238 | CCAUCCUCUGAUAUCUCGCC | 472 | GgcGAGuAucAGAGGAuGGdTsdT | 955 | pCcAUCCUCUGAuAUCUCGCCdTsdT |
| 6 | UGUUCAAACACCUGGUACA | 239 | UGUACCAGGUGUUUGAACA | 473 | uguucAAAcAccuGGuAcAdTsdT | 863 | pUGuAccAGGUGUUUGAAcAdTsdT |
| 7 | GGGUGACCCUUUAGUGAGC | 240 | GCUCACUAAAGGGUCACCC | 474 | GgGuGAcccuuuAGuGAGCdTsdT | 756 | pGCUcACuAAAGGGUcACCCdTsdT |
| 8 | GAAGGAAAGACUAACUUCU | 241 | AGAAGUUAGUCUUUCCUUC | 475 | GaAGGAAAGAcuAAcuucudTsdT | 884 | pAGAAGUuAGUCUUUCCUUCdTsdT |
| 8 | GAAGGAAAGACUAACUUCU | 241 | AGAAGUUAGUCUUUCCUUC | 476 | gaAGGAAAGAcuAAcuucudTsdT | 966 | AGAAGUuAGUCUUUCCUUCdTsdT |
| 8 | GAAGGAAAGACUAACUUCU | 241 | AGAAGUUAGUCUUUCCUUC | 476 | gaAGGAAAGAcuAAcuucudTsdT | 974 | AGAAGUuAGUCUUuCCUUCdTsdT |
| 8 | GAAGGAAAGACUAACUUCU | 241 | AGAAGUUAGUCUUUCCUUC | 476 | gaAGGAAAGAcuAAcuucudTsdT | 982 | AgAAGUuAGUCUUuCCUUCdTsdT |
| 9 | UUCUGAAAUGUAUAGUCUU | 242 | AAGACUAUACAUUUCAGAA | 477 | uucuGAAAuGuAuAGucuudTsdT | 839 | pAAGACuAuAcAUUUcAGAAdTsdT |
| 9 | UUCUGAAAUGUAUAGUCUU | 242 | AAGACUAUACAUUUCAGAA | 477 | uucuGAAAuGuAuAGucuudTsdT | 963 | AAGACuAuAcAUUUcAGAAdTsdT |
| 9 | UUCUGAAAUGUAUAGUCUU | 242 | AAGACUAUACAUUUCAGAA | 477 | uucuGAAAuGuAuAGucuudTsdT | 971 | AAGACuAuAcAUUuCAGAAdTsdT |
| 9 | UUCUGAAAUGUAUAGUCUU | 242 | AAGACUAUACAUUUCAGAA | 477 | uucuGAAAuGuAuAGucuudTsdT | 979 | AaGACuAuAcAUUucAGAAdTsdT |
| 10 | CUGUGUAGCUACCUCACAA | 243 | UUGUGAGGUAGCUACACAG | 478 | cuGuGuAGcuAccucAcAAdTsdT | 744 | pUUGUGAGGuAGCuAcAcAGdTsdT |
| 11 | UGCACUCUAAUGAAGCAAU | 244 | AUUGCUUCAUUAGAGUGCA | 479 | ugcAcucuAAuGAAGcAAudTsdT | 871 | pAUUGCUUcAUuAGAGUGcAdTsdT |
| 12 | CCCAUUUGACUUUAUGGAG | 245 | CUCCAUAAAGUCAAAUGGG | 480 | cccAuuuGAcuuuAuGGAGdTsdT | 739 | pCUCcAuAAAGUcAAAUGGGdTsdT |
| 13 | AAAUGUAUAGUCUUCUUAU | 246 | AUAAGAAGACUAUACAUUU | 481 | AaAuGuAuAGucuucuuAudTsdT | 714 | pAUAAGAAGACuAuAcAUUUdTsdT |
| 13 | AAAUGUAUAGUCUUCUUAU | 246 | AUAAGAAGACUAUACAUUU | 481 | AaAuGuAuAGucuucuuAudTsdT | 939 | pAuAAGAAGACuAuAcAUUUdTsdT |
| 14 | UACAUUGAGUUUGUGGCAG | 247 | CUGCCACAAACUCAAUGUA | 482 | uacAuuGAGuuuGuGGcAGdTsdT | 875 | pCUGCcAcAAACUcAAUGuAdTsdT |
| 15 | CAAUACAUUGAGUUUGUGG | 248 | CCACAAACUCAAUGUAUUG | 483 | caAuAcAuuGAGuuuGuGGdTsdT | 874 | pCCAcAAACUcAAUGuAUUGdTsdT |
| 15 | CAAUACAUUGAGUUUGUGG | 248 | CCACAAACUCAAUGUAUUG | 483 | caAuAcAuuGAGuuuGuGGdTsdT | 953 | pCcAcAAACUcAAUGuAUUGdTsdT |
| 16 | GAACAGGAGUUCCUCACUG | 249 | CAGUGAGGAACUCCUGUUC | 484 | GaAcAGGAGuuccucAcuGdTsdT | 868 | pcAGUGAGGAACUCCUGUUCdTsdT |
| 17 | AUCCCAUGUUCUGGCUUUC | 250 | GAAAGCCAGAACAUGGGAU | 485 | AucccAuGuucuGGcuuucdTsdT | 710 | pGAAAGCcAGAAcAUGGGAUdTsdT |
| 18 | GUAGGUUGUGUGAGUUAAU | 251 | AUUAACUCACACAACCUAC | 486 | GuAGGuuGuGuGAGuuAAudTsdT | 921 | pAUuAACUcAcAcAACCuACdTsdT |
| 19 | AUAGUCUUCUUAUUGCACU | 252 | GUGUCAAUAAGAAGACUAU | 487 | AuAGucuucuuAuuGcAcudTsdT | 715 | pGUGUcAAuAAGAAGACuAUdTsdT |
| 20 | AUUGCACUCUAAUGAAGCA | 253 | UGCUUCAUUAGAGUGCAAU | 488 | AuuGcAcucuAAuGAAGcAdTsdT | 735 | pUGCUUcAUuAGAGUGcAAUdTsdT |
| 21 | UUAUCAAUGCUGUUCGGAU | 254 | AUCCGAACAGCAUUGAUAA | 489 | uuAucAAuGcuGuucGGAudTsdT | 728 | pAUCCGAAcAGcAUUGAuAAdTsdT |
| 22 | AGAAACGAGGACUGAUGCC | 255 | GGCAUCAGUCCUCGUUUCU | 490 | AgAAAcGAGGAcuGAuGccdTsdT | 851 | pGGcAUcAGUCCUCGUUUCUdTsdT |
| 23 | CAUUGAGUUUGUGGCAGAC | 256 | GUCUGCCACAAACUCAAUG | 491 | cauuGAGuuuGuGGcAGAcdTsdT | 876 | pGUCUGCcAcAAACUcAAUGdTsdT |
| 24 | ACAUUCAGCACUGGGAAUC | 257 | GAUUCCCAGUGCUGAAUGU | 492 | AcAuucAGcAcuGGGAAucdTsdT | 708 | pGAUUCCcAGUGCUGAAUGUdTsdT |
| 25 | UGAUGUUCAAACACCUGGU | 258 | ACCAGGUGUUUGAACAUCA | 493 | ugAuGuucAAAcAccuGGudTsdT | 861 | pACcAGGUGUUUGAAcAUcAdTsdT |
| 26 | GGAUAGAACAGGAGUUCCU | 259 | AGGAACUCCUGUUCUAUCC | 494 | GgAuAGAAcAGGAGuuccudTsdT | 866 | pAGGAACUCCUGUUCuAUCCdTsdT |
| 27 | AAUAUUUCACUGGAAGGAA | 260 | UUCCUUCCAGUGAAAUAUU | 495 | AauAuuucAcuGGAAGGAAdTsdT | 741 | pUUCCUUCcAGUGAAAuAUUdTsdT |
| 28 | AAUAAACAUUGUUUGUACU | 261 | AGUACAAACAAUGUUUAUU | 496 | AauAAAcAuuGuuuGuAcudTsdT | 911 | pAGuAcAAAcAAUGUUuAUUdTsdT |
| 29 | UCCCAUGUUCUGGCUUUCU | 262 | AGAAAGCCAGAACAUGGGA | 497 | ucccAuGuucuGGcuuucudTsdT | 711 | pAGAAAGCcAGAAcAUGGGAdTsdT |
| 29 | UCCCAUGUUCUGGCUUUCU | 262 | AGAAAGCCAGAACAUGGGA | 497 | ucccAuGuucuGGcuuucudTsdT | 961 | AGAAAGCcAGAAcAUGGGAdTsdT |
| 29 | UCCCAUGUUCUGGCUUUCU | 262 | AGAAAGCCAGAACAUGGGA | 497 | ucccAuGuucuGGcuuucudTsdT | 969 | AGAAAGCcAGAAcaUGGGAdTsdT |
| 29 | UCCCAUGUUCUGGCUUUCU | 262 | AGAAAGCCAGAACAUGGGA | 497 | ucccAuGuucuGGcuuucudTsdT | 977 | AgAAAGCcAGAAcaUGGGAdTsdT |
| 30 | UUCGGAUAGAACAGGAGUU | 263 | AACUCCUGUUCUAUCCGAA | 498 | uucGGAuAGAAcAGGAGuudTsdT | 734 | pAACUCCUGUUCuAUCCGAAdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 31 | AAGUAGGUUGUGUGAGUUA | 264 | UAACUCACACAACCUACUU | 499 | AaGuAGGuuGuGuGAGuuAdTsdT | 790 | puAACUcAcAcAACCuACUUdTsdT |
| 32 | UUAUAGUGCUGGUAGUAUC | 265 | GAUACUACCAGCACUAUAA | 500 | uuAuAGuGcuGGuAGuAucdTsdT | 746 | pGAuACuACcAGcACuAuAAdTsdT |
| 33 | CUUCUUAUUGACACUUACA | 266 | UGUAAGUGUCAAUAAGAAG | 501 | cuucuuAuuGAcAcuuAcAdTsdT | 842 | pUGuAAGUGUcAAuAAGAAGdTsdT |
| 33 | CUUCUUAUUGACACUUACA | 266 | UGUAAGUGUCAAUAAGAAG | 501 | cuucuuAuuGAcAcuuAcAdTsdT | 965 | UGuAAGUGUcAAuAAGAAGdTsdT |
| 33 | CUUCUUAUUGACACUUACA | 266 | UGUAAGUGUCAAUAAGAAG | 501 | cuucuuAuuGAcAcuuAcAdTsdT | 973 | UGuAAGUGUcAAuaAGAAGdTsdT |
| 33 | CUUCUUAUUGACACUUACA | 266 | UGUAAGUGUCAAUAAGAAG | 501 | cuucuuAuuGAcAcuuAcAdTsdT | 981 | UguAAGUGUcAAuaAGAAGdTsdT |
| 34 | UACAGAAGCCCGCUGUUUC | 267 | GAAACAGCGGGCUUCUGUA | 502 | uacAGAAGcccGcuGuuucdTsdT | 832 | pGAAAcAGCGGGCUUCUGuAdTsdT |
| 35 | GUGACCCUUUAGUGAGCUU | 268 | AAGCUCACUAAAGGGUCAC | 503 | GuGAcccuuuAGuGAGcuudTsdT | 907 | pAAGCUcACuAAAGGGUcACdTsdT |
| 36 | AUAGAACAGGAGUUCCUCA | 269 | UGAGGAACUCCUGUUCUAU | 504 | AuAGAAcAGGAGuuccucAdTsdT | 867 | pUGAGGAACUCCUGUUCuAUdTsdT |
| 37 | CUGGCACUUUACAAACAAA | 270 | UUUGUUUGUAAAGUGCCAG | 505 | cuGGcAcuuuAcAAAcAAAdTsdT | 910 | pUUUGUUUGuAAAGUGCcAGdTsdT |
| 38 | UCUAAUGAAGCAAUACAUU | 271 | AAUGUAUUGCUUCAUUAGA | 506 | ucuAAuGAAGcAAuAcAuudTsdT | 872 | pAAUGuAUUGCUUcAUuAGAdTsdT |
| 39 | UCUUCUUAUUGACACUUAC | 272 | GUAAGUGUCAAUAAGAAGA | 507 | ucuucuuAuuGAcAcuuAcdTsdT | 841 | pGUAAGUGUcAAuAAGAAGdTsdT |
| 39 | UCUUCUUAUUGACACUUAC | 272 | GUAAGUGUCAAUAAGAAGA | 507 | ucuucuuAuuGAcAcuuAcdTsdT | 949 | GuAAGUGUcAAuAAGAAGAdTsdT |
| 39 | UCUUCUUAUUGACACUUAC | 272 | GUAAGUGUCAAUAAGAAGA | 507 | ucuucuuAuuGAcAcuuAcdTsdT | 964 | GUAAGUGUcAAuAAGAAGAdTsdT |
| 39 | UCUUCUUAUUGACACUUAC | 272 | GUAAGUGUCAAUAAGAAGA | 507 | ucuucuuAuuGAcAcuuAcdTsdT | 972 | GUAAGUGUcAAuAaGAAGAdTsdT |
| 39 | UCUUCUUAUUGACACUUAC | 272 | GUAAGUGUCAAUAAGAAGA | 508 | ucuucuUAuuGAcAcuuAcdTsdT | 972 | GUAAGUGUcAAuAaGAAGAdTsdT |
| 39 | UCUUCUUAUUGACACUUAC | 272 | GUAAGUGUCAAUAAGAAGA | 507 | ucuucuuAuuGAcAcuuAcdTsdT | 980 | GuAAGUGUcAAuAaGAAGAdTsdT |
| 39 | UCUUCUUAUUGACACUUAC | 272 | GUAAGUGUCAAUAAGAAGA | 508 | ucuucuUAuuGAcAcuuAcdTsdT | 980 | GuAAGUGUcAAuAaGAAGAdTsdT |
| 39 | UCUUCUUAUUGACACUUAC | 272 | GUAAGUGUCAAUAAGAAGA | 508 | ucuucuUAuuGAcAcuuAcdTsdT | 985 | GuAAGUGUcAAuAaGAAGAdTsdT |
| 40 | UGUUCGGAUAGAACAGGAG | 273 | CUCCUGUUCUAUCCGAACA | 509 | uguucGGAuAGAAcAGGAGdTsdT | 733 | pCUCCUGUUCuAUCCGAAcAdTsdT |
| 41 | AGUACCAUGAUAUCUGGCA | 274 | UGCCAGAUAUCAUGGUACU | 510 | AguAccAuGAuAucuGGcAdTsdT | 820 | pUGCcAGAuAUcAUGGuACUdTsdT |
| 42 | CAGAGAUGAGGGUUUACAC | 275 | GUGUAAACCCUCAUCUCUG | 511 | caGAGAuGAGGGuuuAcAcdTsdT | 856 | pGUGuAAACCCUcAUCUCUGdTsdT |
| 43 | GAAACGAGGACUGAUGCCU | 276 | AGGCAUCAGUCCUCGUUUC | 512 | GaAAcGAGGAcuGAuGccudTsdT | 852 | pAGGcAUcAGUCCUCGUUUCdTsdT |
| 44 | AAGAGAGUAGGCGAGUAUC | 277 | GAUACUCGCCUACUCUCUU | 513 | AaGAGAGuAGGcGAGuAucdTsdT | 888 | pGAuACUCGCCuACUCUCUUdTsdT |
| 45 | CAUUAGCUGAAUAAUGUGA | 278 | UCACAUUAUUCAGCUAAUG | 514 | cauuAGcuGAAuAAuGuGAdTsdT | 932 | pUCAcAUuAUUcAGCuAAUGdTsdT |
| 45 | CAUUAGCUGAAUAAUGUGA | 278 | UCACAUUAUUCAGCUAAUG | 514 | cauuAGcuGAAuAAuGuGAdTsdT | 960 | pUcAcAUuAUUcAGCuAAUGdTsdT |
| 46 | AGUAGAGAACCCAUUUGAC | 279 | GUCAAAUGGGUUCUCUACU | 515 | AguAGAGAAcccAuuuGAcdTsdT | 738 | pGUcAAAUGGGUUCUCuACUdTsdT |
| 47 | AGGCGAGUAUCAGAGGAUG | 280 | CAUCCUCUGAUACUCGCCU | 516 | AgGcGAGuAucAGAGGAuGdTsdT | 893 | pcAUCCUCUGAuACUCGCCUdTsdT |
| 48 | UAGACUAAGCAUGUAAUUU | 281 | AAAUUACAUGCUUAGUCUA | 517 | uaGAcuAAGcAuGuAAuuudTsdT | 784 | pAAAUuAcAUGCUuAGUCuAdTsdT |
| 49 | AACAUUGUUUGUACUCACA | 282 | UGUGAGUACAAACAAUGUU | 518 | AacAuuGuuuGuAcucAcAdTsdT | 913 | pUGUGAGuAcAAAcAAUGUUdTsdT |
| 50 | GAUGGGAGUGAUGUCAAGU | 283 | ACUUGACAUCACUCCCAUC | 519 | GauGGGAGuGAuGucAAGudTsdT | 896 | pACUUGAcAUcACUCCcAUCdTsdT |
| 51 | CAGACCAUUUCCUAAUCAG | 284 | CUGAUUAGGAAAUGGUCUG | 520 | caGAccAuuuccuAAucAGdTsdT | 937 | pCUGAUuAGGAAAUGGUCUGdTsdT |
| 52 | GAUUACAGAAGCCCGCUGU | 285 | ACAGCGGGCUUCUGUAAUC | 521 | GauuAcAGAAGcccGcuGudTsdT | 712 | pACAGCGGGCUUCUGuAAUCdTsdT |
| 52 | GAUUACAGAAGCCCGCUGU | 285 | ACAGCGGGCUUCUGUAAUC | 521 | GauuAcAGAAGcccGcuGudTsdT | 938 | pAcAGCGGGCUUCUGuAAUCdTsdT |
| 53 | CAUUGAAACGAUGCCUUGU | 286 | ACAAGGCAUCGUUUCAAUG | 522 | cauuGAAAcGAuGccuuGudTsdT | 845 | pACAAGGcAUCGUUUcAAUGdTsdT |
| 53 | CAUUGAAACGAUGCCUUGU | 286 | ACAAGGCAUCGUUUCAAUG | 522 | cauuGAAAcGAuGccuuGudTsdT | 950 | pAcAAGGcAUCGUUUcAAUGdTsdT |
| 54 | ACUUAUGCUGGAACUGGGU | 287 | ACCCAGUUCCAGCAUAAGU | 523 | AcuuAuGcuGGAAcuGGGudTsdT | 880 | pACCcAGUUCcAGcAuAAGUdTsdT |
| 55 | GUCGACAAGGAGAACACGC | 288 | GCGUGUUCUCCUUGUCGAC | 524 | GucGAcAAGGAGAAcAcGcdTsdT | 705 | pGCGUGUUCUCCUUGUCGACdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 56 | AGGAAAGACUAACUUCUUU | 289 | AAAGAAGUUAGUCUUUCCU | 525 | AgGAAAGAcuAAcuucuuudTsdT | 885 | pAAAGAAGUuAGUCUUUCCUdTsdT |
| 56 | AGGAAAGACUAACUUCUUU | 289 | AAAGAAGUUAGUCUUUCCU | 526 | agGAAAGAcuAAcuucuuudTsdT | 967 | AAAGAAGUuAGUCUUUCCUdTsdT |
| 56 | AGGAAAGACUAACUUCUUU | 289 | AAAGAAGUUAGUCUUUCCU | 526 | agGAAAGAcuAAcuucuuudTsdT | 975 | AAAGAAGUuAGUCUuUCCUdTsdT |
| 56 | AGGAAAGACUAACUUCUUU | 289 | AAAGAAGUUAGUCUUUCCU | 526 | agGAAAGAcuAAcuucuuudTsdT | 983 | AaAGAAGUuAGUCUUUCCUdTsdT |
| 57 | CAAGACCGCGAGGAGGAUC | 290 | GAUCCUCCUCGCGGUCUUG | 527 | caAGAccGcGAGGAGGAucdTsdT | 816 | pGAUCCUCCUCGCGGUCUUGdTsdT |
| 58 | GACAAUGGCAGUCUUGGCU | 291 | AGCCAAGACUGCCAUUGUC | 528 | GacAAuGGcAGucuuGGcudTsdT | 755 | pAGCcAAGACUGCcAUUGUCdTsdT |
| 59 | AUGCCUUGUGUCAAGAAGA | 292 | UCUUCUUGACACAAGGCAU | 529 | AuGccuuGuGucAAGAAGAdTsdT | 846 | pUCUUCUUGAcAcAAGGcAUdTsdT |
| 60 | GCCUCACUGCUUCAACGCA | 293 | UGCGUUGAAGCAGUGAGGC | 530 | GccucAcuGcuucAAcGcAdTsdT | 909 | pUGCGUUGAAGcAGUGAGGCdTsdT |
| 61 | UACCUCACAACCAGUCCUG | 294 | CAGGACUGGUUGUGAGGUA | 531 | uaccucAcAAccAGuccuGdTsdT | 745 | pcAGGACUGGUUGUGAGGuAdTsdT |
| 62 | GAGAAGAGAGUAGGCGAGU | 295 | ACUCGCCUACUCUCUUCUC | 532 | GaGAAGAGAGuAGGcGAGudTsdT | 887 | pACUCGCCuACUCUCUUCUCdTsdT |
| 63 | AGACUUAUGCUGGAACUGG | 296 | CCAGUUCCAGCAUAAGUCU | 533 | AgAcuuAuGcuGGAAcuGGdTsdT | 879 | pCCAGUUCcAGcAuAAGUCUdTsdT |
| 63 | AGACUUAUGCUGGAACUGG | 296 | CCAGUUCCAGCAUAAGUCU | 533 | AgAcuuAuGcuGGAAcuGGdTsdT | 954 | pCcAGUUCcAGcAuAAGUCUdTsdT |
| 64 | UUACAGAAGCCCGCUGUUU | 297 | AAACAGCGGGCUUCUGUAA | 534 | uuAcAGAAGcccGcuGuuudTsdT | 831 | pAAAcAGCGGGCUUCUGuAAdTsdT |
| 65 | UUAUGCUGGAACUGGGUUU | 298 | AAACCCAGUUCCAGCAUAA | 535 | uuAuGcuGGAAcuGGGuuudTsdT | 881 | pAAACCcAGUUCcAGcAuAAdTsdT |
| 66 | AUAAACAUUGUUUGUACUC | 299 | GAGUACAAACAAUGUUUAU | 536 | AuAAAcAuuGuuuGuAcucdTsdT | 912 | pGAGuAcAAAcAAUGUUuAUdTsdT |
| 67 | UCAAUGCCAUUGAAACGAU | 300 | AUCGUUUCAAUGGCAUUGA | 537 | ucAAuGccAuuGAAAcGAudTsdT | 717 | pAUCGUUUcAAUGGcAUUGAdTsdT |
| 68 | AUAGUGCUGGUAGUAUCAC | 301 | GUGAUACUACCAGCACUAU | 538 | AuAGuGcuGGuAGuAucAcdTsdT | 748 | pGUGAuACuACcAGcACuAUdTsdT |
| 69 | CAGCCUCACUGCUUCAACG | 302 | CGUUGAAGCAGUGAGGCUG | 539 | caGccucAcuGcuucAAcGdTsdT | 908 | pCGUUGAAGcAGUGAGGCUGdTsdT |
| 70 | UCUUGGCUUUAAAGUGAGG | 303 | CCUCACUUUAAAGCCAAGA | 540 | ucuuGGcuuuAAAGuGAGGdTsdT | 905 | pCCUcACUUuAAAGCcAAGAdTsdT |
| 71 | GGCUGUGACUUACCAUAGC | 304 | GCUAUGGUAAGUCACAGCC | 541 | GgcuGuGAcuuAccAuAGcdTsdT | 751 | pGCuAUGGuAAGUcACAGCCdTsdT |
| 72 | GGCUACCUAUGGUGAACGU | 305 | ACGUUCACCAUAGGUAGCC | 542 | GgcuAccuAuGGuGAAcGudTsdT | 722 | pACGUUcACcAuAGGuAGCCdTsdT |
| 73 | CGCGAGGAGGAUCUUCCAG | 306 | CUGGAAGAUCCUCCUCGCG | 543 | cgcGAGGAGGAucuuccAGdTsdT | 819 | pCUGGAAGAUCCUCCUCGCGdTsdT |
| 74 | GCCAUUGAAACGAUGCCUU | 307 | AAGGCAUCGUUUCAAUGGC | 544 | GccAuuGAAAcGAuGccuudTsdT | 718 | pAAGGcAUCGUUUcAAUGGCdTsdT |
| 75 | AGCCUCACUGCUUCAACGC | 308 | GCGUUGAAGCAGUGAGGCU | 545 | AgccucAcuGcuucAAcGcdTsdT | 758 | pGCGUUGAAGcAGUGAGGCUdTsdT |
| 76 | GGCAGACAGACUUAUGCUG | 309 | CAGCAUAAGUCUGUCUGCC | 546 | GgcAGAcAGAcuuAuGcuGdTsdT | 878 | pcAGcAuAAGUCUGUCUGCCdTsdT |
| 77 | GUGACUAAAGUAAGUUAAA | 310 | UUUAACUUACUUUAGUCAC | 547 | GuGAcuAAAGuAAGuuAAAdTsdT | 770 | pUUuAACUuACUUuAGUcACdTsdT |
| 78 | AGUUAUUGUUACCUAAAGU | 311 | ACUUUAGGUAACAAUAACU | 548 | AguuAuuGuuAccuAAAGudTsdT | 800 | pACUUuAGGuAAcAAuAACUdTsdT |
| 79 | GCCUUUAUGUUUGGGAGAA | 312 | UUCUCCCAAACAUAAAGGC | 549 | GccuuuAuGuuuGGGAGAAdTsdT | 924 | pUUCUCCcAAAcAuAAAGGCdTsdT |
| 80 | UUCAGAGUAGAGAACCCAU | 313 | AUGGGUUCUCUACUCUGAA | 550 | uucAGAGuAGAGAAcccAudTsdT | 882 | pAUGGGUUCUCuACUCUGAAdTsdT |
| 81 | AAACGAGGACUGAUGCCUG | 314 | CAGGCAUCAGUCCUCGUUU | 551 | AaAcGAGGAcuGAuGccuGdTsdT | 724 | pcAGGcAUcAGUCCUCGUUUdTsdT |
| 82 | GUAGGCGAGUAUCAGAGGA | 315 | UCCUCUGAUACUCGCCUAC | 552 | GuAGGcGAGuAucAGAGGAdTsdT | 891 | pUCCUCUGAuACUCGCCuACdTsdT |
| 82 | GUAGGCGAGUAUCAGAGGA | 315 | UCCUCUGAUACUCGCCUAC | 553 | guAGGcGAGuAucAGAGGAdTsdT | 968 | UCCUCUGAuACUCGCCuACdTsdT |
| 82 | GUAGGCGAGUAUCAGAGGA | 315 | UCCUCUGAUACUCGCCUAC | 553 | guAGGcGAGuAucAGAGGAdTsdT | 976 | UCCUCUGAuACUCGcCuACdTsdT |
| 82 | GUAGGCGAGUAUCAGAGGA | 315 | UCCUCUGAUACUCGCCUAC | 553 | guAGGcGAGuAucAGAGGAdTsdT | 984 | UcCUCUGAuACUCGcCuACdTsdT |
| 83 | AAGCCCGCUGUUUCUAUGG | 316 | CCAUAGAAACAGCGGGCUU | 554 | AaGcccGcuGuuucuAuGGdTsdT | 835 | pCCAuAGAAAcAGCGGGCUUdTsdT |
| 84 | UCAGCACUGGGAAUCCCUG | 317 | CAGGGAUUCCCAGUGCUGA | 555 | ucAGcAcuGGGAAucccuGdTsdT | 827 | pcAGGGAUUCCcAGUGCUGAdTsdT |
| 85 | GAAUAAUGUGAGGAUUAAC | 318 | GUUAAUCCUCACAUUAUUC | 556 | GaAuAAuGuGAGGAuuAAcdTsdT | 933 | pGUuAAUCCUcAcAUuAUUCdTsdT |
| 86 | UGUGGCAGACAGACUUAUG | 319 | CAUAAGUCUGUCUGCCACA | 557 | uguGGcAGAcAGAcuuAuGdTsdT | 877 | pcAuAAGUCUGUCUGCcAcAdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 87 | AGAGAUAAAUGUUGAUCUU | 320 | AAGAUCAACAUUUAUCUCU | 558 | AgAGAuAAAuGuuGAucuudTsdT | 798 | pAAGAUcAAcAUUuAUCUCUdTsdT |
| 88 | UACCAUGAUAUCUGGCAGA | 321 | UCUGCCAGAUAUCAUGGUA | 559 | uaccAuGAuAucuGGcAGAdTsdT | 821 | pUCUGCcAGAuAUCAUGGuAdTsdT |
| 89 | CUUCCAAAUUGCCAUGGAA | 322 | UUCCAUGGCAAUUUGGAAG | 560 | cuuccAAAuuGccAuGGAAdTsdT | 838 | pUUCcAUGGcAAUUUGGAAGdTsdT |
| 90 | ACCGCGAGGAGGAUCUUCC | 323 | GGAAGAUCCUCCUCGCGGU | 561 | AccGcGAGGAGGAucuccdTsdT | 818 | pGGAAGAUCCUCCUCGCGGUdTsdT |
| 91 | GAAAUGUAUAGUCUUCUUA | 324 | UAAGAAGACUAUACAUUUC | 562 | GaAAuGuAuAGucuucuuAdTsdT | 713 | puAAGAAGACuAuAcAUUUCdTsdT |
| 92 | AUGUUCAAACACCUGGUAC | 325 | GUACCAGGUGUUUGAACAU | 563 | AuGuucAAAcAccuGGuAcdTsdT | 862 | pGUACcAGGGUGUUUGAACAUdTsdT |
| 92 | AUGUUCAAACACCUGGUAC | 325 | GUACCAGGUGUUUGAACAU | 563 | AuGuucAAAcAccuGGuAcdTsdT | 952 | pGuACcAGGUGUUUGAAcAUdTsdT |
| 93 | AGGGAAUUUCUCUUCAAUG | 326 | CAUUGAAGAGAAAUUCCCU | 564 | AgGGAAuuucucuucAAuGdTsdT | 716 | pcAUUGAAGAGAAAUUCCCUdTsdT |
| 94 | CCCUGUUAAGUGGUGAAAU | 327 | AUUUCACCACUUAACAGGG | 565 | cccuGuuAAGuGGuGAAAudTsdT | 789 | pAUUUcACcACUuAAcAGGGdTsdT |
| 95 | GAUGAGGGUUUACACUGUG | 328 | CACAGUGUAAACCCUCAUC | 566 | GauGAGGGuuuAcAcuGuGdTsdT | 857 | pcAcAGUGuAAACCCUcAUCdTsdT |
| 96 | UGUGUGAGUUAAUUCAUUU | 329 | AAAUGAAUUAACUCACACA | 567 | uguGuGAGuuAAuucAuuudTsdT | 922 | pAAAUGAAUuAACUcAcAcAdTsdT |
| 97 | UUGCCUGAUGUUCAAACAC | 330 | GUGUUUGAACAUCAGGCAA | 568 | uuGccuGAuGuucAAAcAcdTsdT | 858 | pGUGUUUGAAcAUcAGGcAAdTsdT |
| 98 | AAACUUGUGUAGACUAAGC | 331 | GCUUAGUCUACACAAGUUU | 569 | AaAcuuGuGuAGAcuAAGcdTsdT | 779 | pGCUuAGUCuAcAcAAGUUUdTsdT |
| 99 | UAUAUCCCAUGUUCUGGCU | 332 | AGCCAGAACAUGGGAUAUA | 570 | uauAucccAuGuucuGGcudTsdT | 828 | pAGCcAGAAcAUGGGAuAuAdTsdT |
| 100 | UUGUGUAGACUAAGCAUGU | 333 | ACAUGCUUAGUCUACACAA | 571 | uuGuGuAGAcuAAGcAuGudTsdT | 781 | pACAUGCUuAGUCuAcAcAAdTsdT |
| 100 | UUGUGUAGACUAAGCAUGU | 333 | ACAUGCUUAGUCUACACAA | 571 | uuGuGuAGAcuAAGcAuGudTsdT | 945 | pAcAUGCUuAGUCuAcAcAAdTsdT |
| 101 | AUGCUGUUCGGAUAGAACA | 334 | UGUUCUAUCCGAACAGCAU | 572 | AuGcuGuucGGAuAGAAcAdTsdT | 730 | pUGUUCuAUCCGAAcAGcAUdTsdT |
| 102 | AAUUAUCAAUGCUGUUCGG | 335 | CCGAACAGCAUUGAUAAUU | 573 | AauuAucAAuGcuGuucGGdTsdT | 727 | pCCGAAcAGcAUUGAuAAUUdTsdT |
| 103 | GCCUGAUGUUCAAACACCU | 336 | AGGUGUUUGAACAUCAGGC | 574 | GccuGAuGuucAAAcAccudTsdT | 859 | pAGGUGUUUGAAcAUcAGGCdTsdT |
| 104 | CAUAGCAGUGACAAUGGCA | 337 | UGCCAUUGUCACUGCUAUG | 575 | cauAgcAGuGAcAAuGGcAdTsdT | 902 | pUGCcAUUGUcACUGCuAUGdTsdT |
| 105 | UGUGAGUUAAUUCAUUUAU | 338 | AUAAAUGAAUUAACUCACA | 576 | uguGAGuuAAuucAuuuAudTsdT | 923 | pAUAAAUGAAUuAACUcAcAdTsdT |
| 105 | UGUGAGUUAAUUCAUUUAU | 338 | AUAAAUGAAUUAACUCACA | 576 | uguGAGuuAAuucAuuuAudTsdT | 959 | pAuAAAUGAAUuAACUcAcAdTsdT |
| 106 | AGUGCUGGUAGUAUCACCU | 339 | AGGUGAUACUACCAGCACU | 577 | AguGcuGGuAGuAucAccudTsdT | 749 | pAGGUGAuACuACcAGcACUdTsdT |
| 107 | UAUCAAUGCUGUUCGGAUA | 340 | UAUCCGAACAGCAUUGAUA | 578 | uaucAAuGcuGuucGGAuAdTsdT | 865 | puAUCCGAAcAGcAUUGAuAdTsdT |
| 108 | GACUAAAGUAAGUUAAACU | 341 | AGUUUAACUUACUUUAGUC | 579 | GacuAAAGuAAGuuAAAcudTsdT | 772 | pAGUUuAACUuACUUuAGUCdTsdT |
| 109 | AAUGCUGUUCGGAUAGAAC | 342 | GUUCUAUCCGAACAGCAUU | 580 | AauGcuGuucGGAuAGAAcdTsdT | 729 | pGUUCuAUCCGAAcAGcAUUdTsdT |
| 110 | AGAAUAUUUCACUGGAAGG | 343 | CCUUCCAGUGAAAUAUUCU | 581 | AgAAuAuuucAcuGGAAGGdTsdT | 740 | pCCUUCcAGUGAAAuAUUCUdTsdT |
| 111 | AUCUGGCAGAUGUAUAAGA | 344 | UCUUAUACAUCUGCCAGAU | 582 | AucuGGcAGAuGuAuAAGAdTsdT | 825 | pUCUuAuAcAUCUGCcAGAUdTsdT |
| 112 | UAUAGUGCUGGUAGUAUCA | 345 | UGAUACUACCAGCACUAUA | 583 | uauAGuGcuGGuAGuAucAdTsdT | 747 | pUGAuAcuACcAGcACuAuAdTsdT |
| 113 | GGCCAGCAAGACCGCGAGG | 346 | CCUCGCGGUCUUGCUGGCC | 584 | GgccAGcAAGAccGcGAGGdTsdT | 706 | pCCUCGCGGUCUUGCUGGCCdTsdT |
| 114 | CCAUGAUAUCUGGCAGAUG | 347 | CAUCUGCCAGAUAUCAUGG | 585 | ccAuGAuAucuGGcAGAuGdTsdT | 823 | pcAUCUGCcAGAuAUCAUGGdTsdT |
| 115 | UUAAACUUGUGUAGACUAA | 348 | UUAGUCUACACAAGUUUAA | 586 | uuAAAcuuGuGuAGAcuAAdTsdT | 777 | pUUAGUCuAcAcAAGUUuAAdTsdT |
| 115 | UUAAACUUGUGUAGACUAA | 348 | UUAGUCUACACAAGUUUAA | 586 | uuAAAcuuGuGuAGAcuAAdTsdT | 944 | pUuAGUCuAcAcAAGUUuAAdTsdT |
| 116 | UUCAAUGCCAUUGAAACGA | 349 | UCGUUUCAAUGGCAUUGAA | 587 | uucAAuGccAuuGAAAcGAdTsdT | 844 | pUCGUUUcAAUGGcAUUGAAdTsdT |
| 117 | AGAAAGCUGAGACAUUGCA | 350 | UGCAAUGUCUCAGCUUUCU | 588 | AgAAAGcuGAGAcAuuGcAdTsdT | 925 | pUGcAAUGUCUcAGCUUUCUdTsdT |
| 118 | CUAUGGCUUCCAAAUUGCC | 351 | GGCAAUUUGGAAGCCAUAG | 589 | cuAuGGcuuccAAAuuGccdTsdT | 837 | pGGcAAUUUGGAAGCcAuAGdTsdT |
| 119 | AAGUGACUAAAGUAAGUUA | 352 | UAACUUACUUUAGUCACUU | 590 | AaGuGAcuAAAGuAAGuuAdTsdT | 769 | puAACUuACUUuAGUcACUUdTsdT |
| 120 | UGACUAAAGUAAGUUAAAC | 353 | GUUUAACUUACUUUAGUCA | 591 | ugAcuAAAGuAAGuuAAAcdTsdT | 771 | pGUUuAACUuACUUuAGUcAdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 121 | UGCUGUUCGGAUAGAACAG | 354 | CUGUUCUAUCCGAACAGCA | 592 | ugcuGuucGGAuAGAAcAGdTsdT | 731 | pCUGUUCuAUCCGAAcAGcAdTsdT |
| 122 | GCGAGUAUCAGAGGAUGGG | 355 | CCCAUCCUCUGAUACUCGC | 593 | GcGAGuAucAGAGGAuGGGdTsdT | 895 | pCCcAUCCUCUGAuACUCGCdTsdT |
| 123 | GGGCCUUGCGCUGGAUUGG | 356 | CCAAUCCAGCGCAAGGCCC | 594 | GgGccuuGcGcuGGAuuGGdTsdT | 848 | pCCAAUCcAGCGcAAGGCCCdTsdT |
| 124 | ACCUCACAACCAGUCCUGU | 357 | ACAGGACUGGUUGUGAGGU | 595 | AccucAcAAccAGuccuGudTsdT | 899 | pACAGGACUGGUUGUGAGGUdTsdT |
| 124 | ACCUCACAACCAGUCCUGU | 357 | ACAGGACUGGUUGUGAGGU | 595 | AccucAcAAccAGuccuGudTsdT | 956 | pAcAGGACUGGUUGUGAGGUdTsdT |
| 125 | ACUAAGUGACUAAAGUAAG | 358 | CUUACUUUAGUCACUUAGU | 596 | AcuAAGuGAcuAAAGuAAGdTsdT | 768 | pCUuACUUuAGUcACUuAGUdTsdT |
| 126 | AUUACAGAAGCCCGCUGUU | 359 | AACAGCGGGCUUCUGUAAU | 597 | AuuAcAGAAGcccGcuGuudTsdT | 830 | pAAcAGCGGGCUUCUGuAAUdTsdT |
| 127 | GAGUAGGCGAGUAUCAGAG | 360 | CUCUGAUACUCGCCUACUC | 598 | GaGuAGGcGAGuAucAGAGdTsdT | 890 | pCUCUGAuACUCGCCuACUCdTsdT |
| 128 | CAGUGACAAUGGCAGUCUU | 361 | AAGACUGCCAUUGUCACUG | 599 | caGuGAcAAuGGcAGucuudTsdT | 904 | pAAGACUGCcAUUGUcACUGdTsdT |
| 129 | GGCCUUGCGCUGGAUUGGG | 362 | CCCAAUCCAGCGCAAGGCC | 600 | GgccuuGcGcuGGAuuGGGdTsdT | 849 | pCCcAAUCcAGCGcAAGGCCdTsdT |
| 130 | UUCUUAUUGACACUUACAU | 363 | AUGUAAGUGUCAAUAAGAA | 601 | uucuuAuuGAcAcuuAcAudTsdT | 843 | pAUGuAAGUGUcAAuAAGAAdTsdT |
| 131 | UUCACUAAGUGACUAAAGU | 364 | ACUUUAGUCACUUAGUGAA | 602 | uucAcuAAGuGAcuAAAGudTsdT | 765 | pACUUuAGUcACUuAGUGAAdTsdT |
| 132 | GUGUGAGUUAAUUCAUUUA | 365 | UAAAUGAAUUAACUCACAC | 603 | GuGuGAGuuAAuucAuuuAdTsdT | 791 | puAAAUGAAUuAACUcAcACdTsdT |
| 133 | CCCGCUCGCGCCCAUCACG | 366 | CGUGAUGGGCGCGAGCGGG | 604 | cccGcucGcGcccAucAcGdTsdT | 813 | pCGUGAUGGGCGCGAGCGGGdTsdT |
| 134 | GUAAGUUAAACUUGUGUAG | 367 | CUACACAAGUUUAACUUAC | 605 | GuAAGuuAAAcuuGuGuAGdTsdT | 775 | pCUAcAcAAGUUuAACUuACdTsdT |
| 134 | GUAAGUUAAACUUGUGUAG | 367 | CUACACAAGUUUAACUUAC | 605 | GuAAGuuAAAcuuGuGuAGdTsdT | 943 | pCUAcAcAAGUUuAACUuACdTsdT |
| 135 | CGGAAGUUGGAAUCAGGUU | 368 | AACCUGAUUCCAACUUCCG | 606 | cgGAAGuuGGAAucAGGuudTsdT | 931 | pAACCUGAUUCcAACUUCCGdTsdT |
| 136 | AUGUGAGGAUUAACUUCUG | 369 | CAGAAGUUAAUCCUCACAU | 607 | AuGuGAGGAuuAAcuucuGdTsdT | 810 | pcAGAAGUuAAUCCUcAcAUdTsdT |
| 137 | UUAAGUGGUGAAAUCAACU | 370 | AGUUGAUUUCACCACUUAA | 608 | uuAAGuGGuGAAAucAAcudTsdT | 919 | pAGUUGAUUUcACcACUuAAdTsdT |
| 138 | UGUAGACUAAGCAUGUAAU | 371 | AUUACAUGCUUAGUCUACA | 609 | uguAGAcuAAGcAuGuAAudTsdT | 783 | pAUuAcAUGCUuAGUCuAcAdTsdT |
| 139 | AUAAUGUGAGGAUUAACUU | 372 | AAGUUAAUCCUCACAUUAU | 610 | AuAAuGuGAGGAuuAAcuudTsdT | 934 | pAAGUuAAUCCUcAcAUuAUdTsdT |
| 140 | GGCUGGCUGUGACUUACCA | 373 | UGGUAAGUCACAGCCAGCC | 611 | GgcuGGcuGuGAcuuAccAdTsdT | 901 | pUGGuAAGUcAcAGCcAGCCdTsdT |
| 141 | AAGAGGCUACCUAUGGUGA | 374 | UCACCAUAGGUAGCCUCUU | 612 | AaGAGGcuAccuAuGGuGAdTsdT | 850 | pUCACcAuAGGuAGCCUCUUdTsdT |
| 141 | AAGAGGCUACCUAUGGUGA | 374 | UCACCAUAGGUAGCCUCUU | 612 | AaGAGGcuAccuAuGGuGAdTsdT | 951 | pUcACcAuAGGuAGCCUCUUdTsdT |
| 142 | CAGAUUACAGAAGCCCGCU | 375 | AGCGGGCUUCUGUAAUCUG | 613 | caGAuuAcAGAAGcccGcudTsdT | 829 | pAGCGGGCUUCUGuAAUCUGdTsdT |
| 143 | UGAGGCCUUGCCUGUGAAG | 376 | CUUCACAGGCAAGGCCUCA | 614 | ugAGGccuuGccuGuGAAGdTsdT | 869 | pCUUcAcAGGcAAGGCCUcAdTsdT |
| 144 | AUAAUUAUCAAUGCUGUUC | 377 | GAACAGCAUUGAUAAUUAU | 615 | AuAAuuAucAAuGcuGuucdTsdT | 726 | pGAAcAGCAUUGAuAAUuAUdTsdT |
| 145 | GUGACUUACCAUAGCAGUG | 466 | CACUGCUAUGGUAAGUCAC | 616 | GuGAcuuAccAuAGcAGuGdTsdT | 753 | pcACUGCuAUGGuAAGUcACdTsdT |
| 146 | UAGGGCUACUUUGAAUUAA | 378 | UUAAUUCAAAGUAGCCCUA | 617 | uaGGGcuAcuuuGAAuuAAdTsdT | 795 | pUUAAUUcAAAGuAGCCCuAdTsdT |
| 146 | UAGGGCUACUUUGAAUUAA | 378 | UUAAUUCAAAGUAGCCCUA | 617 | uaGGGcuAcuuuGAAuuAAdTsdT | 946 | pUuAAUUcAAAGuAGCCCuAdTsdT |
| 147 | UGGCAGAUGUAUAAGAAGG | 379 | CCUUCUUAUACAUCUGCCA | 618 | ugGcAGAuGuAuAAGAAGGdTsdT | 826 | pCCUUCUuAuAcAUCUGCcAdTsdT |
| 148 | AUAGCUUGAUUUAUUUGGU | 380 | ACCAAAUAAAUCAAGCUAU | 619 | AuAGcuuGAuuuAuuuGGudTsdT | 759 | pAccAAAuAAAUcAAGCuAUdTsdT |
| 149 | CAGCAAGACCGCGAGGAGG | 381 | CCUCCUCGCGGUCUUGCUG | 620 | caGcAAGAccGcGAGGAGGdTsdT | 707 | pCCUCCUCGCGGUCUUGCUGdTsdT |
| 150 | GACUGAUGCCUGGCCUCAC | 382 | GUGAGGCCAGGCAUCAGUC | 621 | GacuGAuGccuGGccucAcdTsdT | 854 | pGUGAGGCcAGGcAUcAGUCdTsdT |
| 151 | UUACCUUGGAUGCUGACUU | 383 | AAGUCAGCAUCCAAGGUAA | 622 | uuAccuuGGAuGcuGAcuudTsdT | 897 | pAAGUcAGCAUCcAAGGuAAdTsdT |
| 152 | AUUCAGCACUGGGAAUCCC | 384 | GGGAUUCCCAGUGCUGAAU | 623 | AuucAGcAcuGGGAAucccdTsdT | 709 | pGGGAUUCCcAGUGCUGAAUdTsdT |
| 153 | AGCAAGACCGCGAGGAGGA | 385 | UCCUCCUCGCGGUCUUGCU | 624 | AgcAAGAccGcGAGGAGGAdTsdT | 814 | pUCCUCCUCGCGGUCUUGCUdTsdT |
| 154 | AGGGCUACUUUGAAUUAAU | 386 | AUUAAUUCAAAGUAGCCCU | 625 | AgGGcuAcuuuGAAuuAAudTsdT | 796 | pAUuAAUUcAAAGuAGCCCUdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 155 | UAAGUUAUUGUUACCUAAA | 387 | UUUAGGUAACAAUAACUUA | 626 | uaAGuuAuuGuuAccuAAAdTsdT | 799 | pUUuAGGuAAcAAuAACUuAdTsdT |
| 156 | UUUAUAGUGCUGGUAGUAU | 388 | AUACUACCAGCACUAUAAA | 627 | uuuAuAGuGcuGGuAGuAudTsdT | 900 | pAUACuACcAGcACuAuAAAdTsdT |
| 156 | UUUAUAGUGCUGGUAGUAU | 388 | AUACUACCAGCACUAUAAA | 627 | uuuAuAGuGcuGGuAGuAudTsdT | 957 | pAuACuACcAGcACuAuAAAdTsdT |
| 157 | GCAAGACCGCGAGGAGGAU | 389 | AUCCUCCUCGCGGUCUUGC | 628 | GcAAGAccGcGAGGAGGAudTsdT | 815 | pAUCCUCCUCGCGGUCUUGCdTsdT |
| 158 | UCUAUGGCUUCCAAAUUGC | 390 | GCAAUUUGGAAGCCAUAGA | 629 | ucuAuGGcuuccAAAuuGcdTsdT | 836 | pGCAAUUUGGAAGCcAuAGAdTsdT |
| 159 | AAAGACUAACUUCUUUGAG | 391 | CUCAAAGAAGUUAGUCUUU | 630 | AaAGAcuAAcuucuuuGAGdTsdT | 886 | pCUcAAAGAAGUuAGUCUUUdTsdT |
| 160 | ACCAUGAUAUCUGGCAGAU | 392 | AUCUGCCAGAUAUCAUGGU | 631 | AccAuGAuAucuGGcAGAudTsdT | 822 | pAUCUGCcAGAuAUcAUGGUdTsdT |
| 161 | GACCAUUUCCUAAUCAGUU | 393 | AACUGAUUAGGAAAUGGUC | 632 | GaccAuuuccuAAucAGuudTsdT | 811 | pAACUGAUuAGGAAAUGGUCdTsdT |
| 162 | UUACCAUAGCAGUGACAAU | 394 | AUUGUCACUGCUAUGGUAA | 633 | uuAccAuAGcAGuGAcAAudTsdT | 754 | pAUUGUcACUGCuAUGGuAAdTsdT |
| 163 | AAUGUGAGGAUUAACUUCU | 395 | AGAAGUUAAUCCUCACAUU | 634 | AauGuGAGGAuuAAcuucudTsdT | 809 | pAGAAGUuAAUCCUcAcAUUdTsdT |
| 164 | UAGUGUCCUGGGAUUCUCU | 396 | AGAGAAUCCCAGGACACUA | 635 | uaGuGuccuGGGAuucucudTsdT | 916 | pAGAGAAUCCcAGGAcACuAdTsdT |
| 165 | UGUUAAGUGGUGAAAUCAA | 397 | UUGAUUUCACCACUUAACA | 636 | uguuAAGuGGuGAAAucAAdTsdT | 918 | pUUGAUUUcAccACUuAAcAdTsdT |
| 166 | ACAAAUAUUCUUAAUAGGG | 398 | CCCUAUUAAGAAUAUUUGU | 637 | AcAAAuAuucuuAAuAGGGdTsdT | 792 | pCCCuAUuAAGAAuAUUUGUdTsdT |
| 167 | GCGGAAGUUGGAAUCAGGU | 399 | ACCUGAUUCCAACUUCCGC | 638 | GcGGAAGuuGGAAucAGGudTsdT | 930 | pACCUGAUUCcAACUUCCGCdTsdT |
| 168 | AACUUGUGUAGACUAAGCA | 400 | UGCUUAGUCUACACAAGUU | 639 | AacuuGuGuAGAcuAAGcAdTsdT | 780 | pUGCUuAGUCuAcAcAAGUUdTsdT |
| 169 | AUUCUUAAUAGGGCUACUU | 401 | AAGUAGCCCUAUUAAGAAU | 640 | AuucuuAAuAGGGcuAcuudTsdT | 794 | pAAGuAGCCCuAUuAAGAAUdTsdT |
| 170 | CCUAAAGUUAAUCCAGAUU | 402 | AAUCUGGAUUAACUUUAGG | 641 | ccuAAAGuuAAuccAGAuudTsdT | 929 | pAAUCUGGAUuAACUUuAGGdTsdT |
| 171 | UAUUGUUACCUAAAGUUAA | 403 | UUAACUUUAGGUAACAAUA | 642 | uauuGuuAccuAAAGuuAAdTsdT | 803 | pUUAACUUuAGGuAAcAAuAdTsdT |
| 171 | UAUUGUUACCUAAAGUUAA | 403 | UUAACUUUAGGUAACAAUA | 642 | uauuGuuAccuAAAGuuAAdTsdT | 947 | pUuAACUUuAGGuAAcAAuAdTsdT |
| 172 | GUGCUGGUAGUAUCACCUU | 404 | AAGGUGAUACUACCAGCAC | 643 | GuGcuGGuAGuAucAccuudTsdT | 750 | pAAGGUGAuACuACcAGcACdTsdT |
| 173 | CUGUGACUUACCAUAGCAG | 405 | CUGCUAUGGUAAGUCACAG | 644 | cuGuGAcuuAccAuAGcAGdTsdT | 752 | pCUGCuAUGGuAAGUcAcAGdTsdT |
| 174 | GAGCUUCUUAAGUUAAAUC | 406 | GAUUUAACUUAAGAAGCUC | 645 | GaGcuucuuAAGuuAAAucdTsdT | 917 | pGAUUuAACUuAAGAAGCUCdTsdT |
| 175 | CUGUUCGGAUAGAACAGGA | 407 | UCCUGUUCUAUCCGAACAG | 646 | cuGuucGGAuAGAAcAGGAdTsdT | 732 | pUCCUGUUCuAUCCGAAcAGdTsdT |
| 176 | GUUAUUGUUACCUAAAGUU | 408 | AACUUUAGGUAACAAUAAC | 647 | GuuAuuGuuAccuAAAGuudTsdT | 801 | pAACUUuAGGuAAcAAuAACdTsdT |
| 177 | UAAUGUGAGGAUUAACUUC | 409 | GAAGUUAAUCCUCACAUUA | 648 | uaAuGuGAGGAuuAAcuucdTsdT | 935 | pGAAGUuAAUCCUcAcAUuAdTsdT |
| 178 | ACCACUAAUGGGAGCCAAU | 410 | AUUGGCUCCCAUUAGUGGU | 649 | AccAcuAAuGGGAGccAAudTsdT | 764 | pAUUGGCUCCcAUuAGUGGUdTsdT |
| 179 | UGUGUAGACUAAGCAUGUA | 411 | UACAUGCUUAGUCUACACA | 650 | uguGuAGAcuAAGcAuGuAdTsdT | 782 | puAcAUGCUuAGUCuAcAcAdTsdT |
| 180 | UGGGCCUUGCGCUGGAUUG | 412 | CAAUCCAGCGCAAGGCCCA | 651 | ugGGccuuGcGcuGGAuuGdTsdT | 847 | pcAAUCcAGCGcAAGGCCcAdTsdT |
| 181 | AGGAGCUUCUUAAGUUAAA | 413 | UUUAACUUAAGAAGCUCCU | 652 | AgGAGcuucuuAAGuuAAAdTsdT | 788 | pUUuAACUuAAGAAGCUCCUdTsdT |
| 182 | GGUGACCCUUUAGUGAGCU | 414 | AGCUCACUAAAGGGUCACC | 653 | GguGAcccuuuAGuGAGcudTsdT | 757 | pAGCUcACuAAAGGGUcACCdTsdT |
| 183 | AGAGUAGGCGAGUAUCAGA | 415 | UCUGAUACUCGCCUACUCU | 654 | AgAGuAGGcGAGuAucAGAdTsdT | 889 | pUCUGAuACUCGCCuACUCUdTsdT |
| 184 | GCAGUGACAAUGGCAGUCU | 416 | AGACUGCCAUUGUCACUGC | 655 | GcAGuGAcAAuGGcAGucudTsdT | 903 | pAGACUGCcAUUGUcACUGCdTsdT |
| 185 | AAACGAUGCCUUGUGUCAA | 417 | UUGACACAAGGCAUCGUUU | 656 | AaAcGAuGccuuGuGucAAdTsdT | 719 | pUUGAcAcAAGGcAUCGUUUdTsdT |
| 186 | GGACUGAUGCCUGGCCUCA | 418 | UGAGGCCAGGCAUCAGUCC | 657 | GgAcuGAuGccuGGccucAdTsdT | 853 | pUGAGGCcAGGcAUcAGUCCdTsdT |
| 187 | UGAGAGAUAAAUGUUGAUC | 419 | GAUCAACAUUUAUCUCUCA | 658 | ugAGAGAuAAAuGuuGAucdTsdT | 797 | pGAUcAAcAUUuAUCUCUcAdTsdT |
| 188 | UGGUUUCUACACCAAAUAC | 420 | GUAUUUGGUGUAGAAACCA | 659 | ugGuuucuAcAccAAAuAcdTsdT | 760 | pGUAUUUGGUGuAGAAACcAdTsdT |
| 188 | UGGUUUCUACACCAAAUAC | 420 | GUAUUUGGUGUAGAAACCA | 659 | ugGuuucuAcAccAAAuAcdTsdT | 941 | pGuAUUUGGUGuAGAAACcAdTsdT |
| 189 | UCUCUGUAAUAUGAUACAU | 421 | AUGUAUCAUAUUACAGAGA | 660 | ucucuGuAAuAuGAuAcAudTsdT | 927 | pAUGuAUcAuAUuAcAGAGAdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 190 | GAGAGAUAAAUGUUGAUCU | 422 | AGAUCAACAUUUAUCUCUC | 661 | GaGAGAuAAAuGuuGAucudTsdT | 926 | pAGAUcAAcAUUuAUCUCUCdTsdT |
| 191 | ACUCUAAUGAAGCAAUACA | 423 | UGUAUUGCUUCAUUAGAGU | 662 | AcucuAAuGAAGcAAuAcAdTsdT | 736 | pUGuAUUGCUUcAUuAGAGUdTsdT |
| 192 | UGAAGUGUUACCAACUAGC | 424 | GCUAGUUGGUAACACUUCA | 663 | ugAAGuGuuAccAAcuAGcdTsdT | 743 | pGCuAGUUGGuAAcACUUcAdTsdT |
| 193 | AAUGAAGCAAUACAUUGAG | 425 | CUCAAUGUAUUGCUUCAUU | 664 | AauGAAGcAAuAcAuuGAGdTsdT | 873 | pCUcAAUGuAUUGCUUcAUUdTsdT |
| 194 | ACGAUGCCUUGUGUCAAGA | 426 | UCUUGACACAAGGCAUCGU | 665 | AcGAuGccuuGuGucAAGAdTsdT | 720 | pUCUUGAcAcAAGGcAUCGUdTsdT |
| 195 | AGACCGCGAGGAGGAUCUU | 427 | AAGAUCCUCCUCGCGGUCU | 666 | AgAccGcGAGGAGGAucuudTsdT | 817 | pAAGAUCCUCCUCGCGGUCUdTsdT |
| 196 | UUGUUACCUAAAGUUAAUC | 428 | GAUUAACUUUAGGUAACAA | 667 | uuGuuAccuAAAGuuAAucdTsdT | 804 | pGAUuAACUUuAGGuAAcAAdTsdT |
| 197 | CAGAAGCCCGCUGUUUCUA | 429 | UAGAAACAGCGGGCUUCUG | 668 | caGAAGcccGcuGuuucuAdTsdT | 833 | puAGAAAcAGCGGGCUUCUGdTsdT |
| 198 | UUUGACUUUAUGGAGAAUA | 430 | UAUUCUCCAUAAAGUCAAA | 669 | uuuGAcuuuAuGGAGAAuAdTsdT | 883 | puAUUCUCcAuAAAGUcAAAdTsdT |
| 199 | UACCUAAAGUUAAUCCAGA | 431 | UCUGGAUUAACUUUAGGUA | 670 | uaccuAAAGuuAAuccAGAdTsdT | 807 | pUCUGGAUuAACUUuAGGuAdTsdT |
| 200 | UUCAAACACCUGGUACACA | 432 | UGUGUACCAGGUGUUUGAA | 671 | uucAAAcAccuGGuAcAcAdTsdT | 864 | pUGUGuAccAGGUGUUUGAAdTsdT |
| 201 | UUGCACUCUAAUGAAGCAA | 433 | UUGCUUCAUUAGAGUGCAA | 672 | uuGcAcucuAAuGAAGcAAdTsdT | 870 | pUUGCUUcAUuAGAGUGcAAdTsdT |
| 202 | UGUUACCUAAAGUUAAUCC | 434 | GGAUUAACUUUAGGUAACA | 673 | uguuAccuAAAGuuAAuccdTsdT | 805 | pGGAUuAACUUuAGGuAAcAdTsdT |
| 203 | CACUAAGUGACUAAAGUAA | 435 | UUACUUUAGUCACUUAGUG | 674 | cacuAAGuGAcuAAAGuAAdTsdT | 767 | pUUACUUuAGUcACUuAGUGdTsdT |
| 203 | CACUAAGUGACUAAAGUAA | 435 | UUACUUUAGUCACUUAGUG | 674 | cacuAAGuGAcuAAAGuAAdTsdT | 942 | pUuACUUuAGUcACUuAGUGdTsdT |
| 204 | UGCCAGAUAGAAGACAGGU | 436 | ACCUGUCUUCUAUCUGGCA | 675 | ugccAGAuAGAAGAcAGGudTsdT | 786 | pACCUGUCUUCuAUCUGGcAdTsdT |
| 205 | AAUGUAUAGUCUUCUUAUU | 437 | AAUAAGAAGACUAUACAUU | 676 | AauGuAuAGucuucuuAuudTsdT | 840 | pAAuAAGAAGACuAuAcAUUdTsdT |
| 206 | GACCACUAAUGGGAGCCAA | 438 | UUGGCUCCCAUUAGUGGUC | 677 | GaccAcuAAuGGGAGccAAdTsdT | 914 | pUUGGCUCCcAUuAGUGGUCdTsdT |
| 207 | GUUACCUAAAGUUAAUCCA | 439 | UGGAUUAACUUUAGGUAAC | 678 | GuuAccuAAAGuuAAuccAdTsdT | 928 | pUGGAUuAACUUuAGGuAACdTsdT |
| 208 | UGAUGCCUGGCCUCACAUU | 440 | AAUGUGAGGCCAGGCAUCA | 679 | ugAuGccuGGccucAcAuudTsdT | 855 | pAAUGUGAGGCcAGGcAUcAdTsdT |
| 209 | CCAACUUUAAAGUCAGCC | 441 | GGACUGACUUUAAAGUUGG | 680 | ccAAcuuuAAAGucAGuccdTsdT | 915 | pGGACUGACUUuAAAGUUGGdTsdT |
| 210 | UAAACUUGUGUAGACUAAG | 442 | CUUAGUCUACACAAGUUUA | 681 | uaAAcuuGuGuAGAcuAAGdTsdT | 778 | pCUuAGUCuAcAcAAGUUuAdTsdT |
| 211 | AGUAGGUUGUGUGAGUUAA | 443 | UUAACUCACACAACCUACU | 682 | AguAGGuuGuGuGAGuuAAdTsdT | 920 | pUUAACUcAcAcAACCuACUdTsdT |
| 211 | AGUAGGUUGUGUGAGUUAA | 443 | UUAACUCACACAACCUACU | 682 | AguAGGuuGuGuGAGuuAAdTsdT | 958 | pUuAACUcAcAcAACCuACUdTsdT |
| 212 | GUUAAACUUGUGUAGACUA | 444 | UAGUCUACACAAGUUUAAC | 683 | GuuAAAcuuGuGuAGAcuAdTsdT | 776 | puAGUCuAcAcAAGUUuAACdTsdT |
| 213 | CUGACCACUAAUGGGAGCC | 445 | GGCUCCCAUUAGUGGUCAG | 684 | cuGAccAcuAAuGGGAGccdTsdT | 762 | pGGCUCCcAUuAGUGGUcAGdTsdT |
| 214 | UAUUCUUAAUAGGGCUACU | 446 | AGUAGCCCUAUUAAGAAUA | 685 | uauucuuAAuAGGGcuAcudTsdT | 793 | pAGuAGCCCuAUuAAGAAuAdTsdT |
| 215 | GUAGUGUCCUGGGAUUCUC | 447 | GAGAAUCCCAGGACACUAC | 686 | GuAGuGuccuGGGAuucucdTsdT | 787 | pGAGAAUCCCAGGAcACuACdTsdT |
| 216 | UAUCUGGCAGAUGUAUAAG | 448 | CUUAUACAUCUGCCAGAUA | 687 | uaucuGGcAGAuGuAuAAGdTsdT | 824 | pCUuAuAcAUCUGCcAGAuAdTsdT |
| 217 | AGGCUACCUAUGGUGAACG | 449 | CGUUCACCAUAGGUAGCCU | 688 | AgGcuAccuAuGGuGAAcGdTsdT | 721 | pCGUUcACcAUAGGuAGCCUdTsdT |
| 218 | UCAGACCAUUUCCUAAUCA | 450 | UGAUUAGGAAAUGGUCUGA | 689 | ucAGAccAuuuccuAAucAdTsdT | 936 | pUGAUuAGGAAAUGGUCUGAdTsdT |
| 219 | UUACCUAAAGUUAAUCCAG | 451 | CUGGAUUAACUUUAGGUAA | 690 | uuAccuAAAGuuAAuccAGdTsdT | 806 | pCUGGAUuAACUUuAGGuAAdTsdT |
| 220 | GGUUUCUACACCAAAUACA | 452 | UGUAUUUGGUGUAGAAACC | 691 | GguuucuAcAccAAAuAcAdTsdT | 761 | pUGuAUUUGGUGuAGAAACCdTsdT |
| 221 | GUUGGUGCCAGAUAGAAGA | 453 | UCUUCUAUCUGGCACCAAC | 692 | GuuGGuGccAGAuAGAAGAdTsdT | 785 | pUCUUCuAUCUGGcACcAACdTsdT |
| 222 | GCUACCUAUGGUGAACGUG | 454 | CACGUUCACCAUAGGUAGC | 693 | GcuAccuAuGGuGAAcGuGdTsdT | 723 | pcACGUUcACcAUAGGuAGCdTsdT |
| 223 | UCACUAAGUGACUAAAGUA | 455 | UACUUUAGUCACUUAGUGA | 694 | ucAcuAAGuGAcuAAAGuAdTsdT | 766 | puACUUuAGUcACUuAGUGAdTsdT |
| 224 | UUAUUGUUACCUAAAGUUA | 456 | UAACUUUAGGUAACAAUAA | 695 | uuAuuGuuAccuAAAGuuAdTsdT | 802 | puAACUUuAGGuAAcAAuAAdTsdT |
| 225 | UAGCUGAAUAAUGUGAGGA | 457 | UCCUCACAUUAUUCAGCUA | 696 | uaGcuGAAuAAuGuGAGGAdTsdT | 808 | pUCCUcAcAUuAUUcAGCuAdTsdT |

TABLE 5-continued

| SEQ ID NO | sense strand sequence (5'-3') | SEQ ID NO | antisense strand sequence (5'-3') | SEQ ID NO | sense strand sequence (5'-3') | SEQ ID NO | antisense strand sequence (5'-3') |
|---|---|---|---|---|---|---|---|
| 226 | UGACCACUAAUGGGAGCCA | 458 | UGGCUCCCAUUAGUGGUCA | 697 | ugAccAcuAAuGGGAGccAdTsdT | 763 | pUGGCUCCcAUuAGUGGUcAdTsdT |
| 227 | GUAGCUACCUCACAACCAG | 459 | CUGGUUGUGAGGUAGCUAC | 698 | GuAGcuAccucAcAAccAGdTsdT | 898 | pCUGGUUGUGAGGUAGCuACdTsdT |
| 228 | UCCCGCUCGCGCCCAUCAC | 460 | GUGAUGGGCGCGAGCGGGA | 699 | ucccGcucGcGcccAucAcdTsdT | 812 | pGUGAUGGGCGCGAGCGGGAdTsdT |
| 229 | CUUGGCUUUAAAGUGAGGG | 461 | CCCUCACUUUAAAGCCAAG | 700 | cuuGGcuuuAAAGuGAGGGdTsdT | 906 | pCCCUcACUUUAAAGCcAAGdTsdT |
| 230 | AGAAGCCCGCUGUUUCUAU | 462 | AUAGAAACAGCGGGCUUCU | 701 | AgAAGcccGcuGuuucuAudTsdT | 834 | pAUAGAAAcAGCGGGCUUCUdTsdT |
| 230 | AGAAGCCCGCUGUUUCUAU | 462 | AUAGAAACAGCGGGCUUCU | 701 | AgAAGcccGcuGuuucuAudTsdT | 948 | pAuAGAAAcAGCGGGCUUCUdTsdT |
| 231 | ACUAAAGUAAGUUAAACUU | 463 | AAGUUUAACUUACUUUAGU | 702 | AcuAAAGuAAGuuAAAcuudTsdT | 773 | pAAGUUuAACUUACUUuAGUdTsdT |
| 232 | AGUAAGUUAAACUUGUGUA | 464 | UACACAAGUUUAACUUACU | 703 | AguAAGuuAAAcuuGuGuAdTsdT | 774 | puAcAcAAGUUuAACUuACUdTsdT |
| 233 | AAUAAUUAUCAAUGCUGUU | 465 | AACAGCAUUGAUAAUUAUU | 704 | AauAAuuAucAAuGcuGuudTsdT | 725 | pAAcAGcAUUGAuAAUuAUUdTsdT |

TABLE 6

| FPL Name | Function | Sequence | SEQ ID No. |
|---|---|---|---|
| hsRRM001 | CE | cgggtttcagggattcccagTTTTTctcttggaaagaaagt | 997 |
| hsRRM002 | CE | gcttgctgcaaagaaagccaTTTTTctcttggaaagaaagt | 998 |
| hsRRM003 | CE | cttcttggctaaatcgctccaTTTTTctcttggaaagaaagt | 999 |
| hsRRM004 | CE | agcgggcttctgtaatctgaaTTTTTctcttggaaagaaagt | 1000 |
| hsRRM005 | CE | gagaaattcccttctttgggaTTTTTctcttggaaagaaagt | 1001 |
| hsRRM006 | CE | ggtagcctctttgtccccaatTTTTTctcttggaaagaaagt | 1002 |
| hsRRM007 | LE | gaacatgggatataaatatctctcctTTTTTaggcataggacccgtgtct | 1003 |
| hsRRM008 | LE | ccaagttttcatttactatgccatcTTTTTaggcataggacccgtgtct | 1004 |
| hsRRM009 | LE | catttcagaatgtatgttttccatgTTTTTaggcataggacccgtgtct | 1005 |
| hsRRM010 | LE | catcgtttcaatggcattgaaTTTTTaggcataggacccgtgtct | 1006 |
| hsRRM011 | LE | ccagcgcaaggcccagtTTTTTaggcataggacccgtgtct | 1007 |
| hsRRM012 | LE | aaggctacaacacgttcaccataTTTTTaggcataggacccgtgtct | 1008 |
| hsRRM013 | LE | aatgccttccactgcagcaTTTTTaggcataggacccgtgtct | 1009 |
| hsRRM014 | BL | gcaatttggaagccatagaaac | 1010 |
| hsRRM015 | BL | tcttttatgtaagtgtcaataagaagactata | 1011 |
| hsRRM016 | BL | ctgccttcttcttgacacaagg | 1012 |

TABLE 7

| FPL Name | Function | Sequence | SEQ ID No. |
|---|---|---|---|
| hGAP001 | CE | gaatttgccatgggtggaatTTTTTctcttggaaagaaagt | 986 |
| hGAP002 | CE | ggagggatctcgctcctggaTTTTTctcttggaaagaaagt | 987 |
| hGAP003 | CE | ccccagccttctccatggtTTTTTctcttggaaagaaagt | 988 |
| hGAP004 | CE | gctccccctgcaaatgagTTTTTctcttggaaagaaagt | 989 |
| hGAP005 | LE | agccttgacggtgccatgTTTTTaggcataggacccgtgtct | 990 |
| hGAP006 | LE | gatgacaagcttcccgttctcTTTTTaggcataggacccgtgtct | 991 |

TABLE 7-continued

| FPL Name | Function | Sequence | SEQ ID No. |
|---|---|---|---|
| hGAP007 | LE | agatggtgatgggatttccattTTTTTaggcataggacccgtgtct | 992 |
| hGAP008 | LE | gcatcgccccacttgattttTTTTTaggcataggacccgtgtct | 993 |
| hGAP009 | LE | cacgacgtactcagcgccaTTTTTaggcataggacccgtgtct | 994 |
| hGAP010 | LE | ggcagagatgatgacccttttgTTTTTaggcataggacccgtgtct | 995 |
| hGAP011 | BL | ggtgaagacgccagtggactc | 996 |

TABLE 8

| | | bDNA | | | |
|---|---|---|---|---|---|
| | p53 status | expt. 1 | expt. 2 | Cell-Titer Glo | xCELLigence |
| SEQ ID 497/711 | | | | | |
| HepG2 | wt | 10.1 | 33 | 540 | 210 |
| HLF | mutant | 4.7 | 37 | 180 | 80 |
| A549 | wt | 5.2 | 165 | 520 | 140 |
| SEQ ID 477/839 | | | | | |
| HepG2 | wt | 3.6 | 28 | 380 | 130 |
| HLF | mutant | 0.73 | 21 | 120 | 69 |
| A549 | wt | 0.73 | 21 | 190 | 160 |

TABLE 9

| | 24 hr | 48 hr | 72 hr |
|---|---|---|---|
| SEQ ID 497/711 | | | |
| HepG2 | 81 | 85 | 85 |
| HLF | 90 | 90 | 83 |
| A549 | 84 | 59 | ND |
| SEQ ID 477/839 | | | |
| HepG2 | 87 | 76 | 75 |
| HLF | 96 | 92 | 62 |
| A549 | 91 | 54 | ND |

We claim:

1. A double-stranded ribonucleic acid molecule for inhibiting the expression of a ribonucleotide reductase M2 (RRM2) gene, wherein the double-stranded ribonucleic acid molecule comprises a sense strand and an antisense strand, wherein the antisense strand and the sense strand are each less than about 30 nucleotides in length, wherein the antisense strand comprises the nucleotide sequence of any of SEQ ID NO: 300, 331, 351, 369, 379, 393, 405 or 424, wherein the sense strand is at least substantially complementary to the antisense strand, and wherein the sense strand and/or the antisense strand comprises at least one modified nucleotide.

2. The double-stranded ribonucleic acid molecule of claim 1, wherein the antisense strand and the sense strand are each 19-24 nucleotides in length.

3. The double-stranded ribonucleic acid molecule of claim 2, wherein the modified nucleotide is selected from the group consisting of: 2'-O-methyl modified nucleotide, nucleotide comprising a 5'-phosphorothioate group, 2'-deoxy-2'-fluoro modified nucleotide, 2'-deoxy-modified nucleotide, locked nucleotide, abasic nucleotide, inverted deoxythymidine, 2'-amino-modified nucleotide, 2'-alkyl-modified nucleotide, morpholino nucleotide, phosphoramidate, and non-natural base comprising nucleotide.

4. The double-stranded ribonucleic acid molecule of claim 2, wherein the sense strand and the antisense strand each comprise at least one modified nucleotide.

5. The double-stranded ribonucleic acid molecule of claim 4, wherein the modified nucleotide in the sense strand and the modified nucleotide in the antisense strand is independently selected from the group consisting of: 2'-O-methyl modified nucleotide, nucleotide comprising a 5'-phosphorothioate group, 2'-deoxy-2'-fluoro modified nucleotide, 2'-deoxy-modified nucleotide, locked nucleotide, abasic nucleotide, inverted deoxythymidine, 2'-amino-modified nucleotide, 2'-alkyl-modified nucleotide, morpholino nucleotide, phosphoramidate, and non-natural base comprising nucleotide.

6. The double-stranded ribonucleic acid molecule of claim 1, wherein the sense strand comprises the nucleotide sequence of any of SEQ ID NO: 67, 98, 118, 136, 147, 161, 173, or 192.

7. The double-stranded ribonucleic acid molecule of claim 6, wherein the sense strand and/or the antisense strand further comprises a 3' overhang of 1-5 nucleotides in length.

8. The double-stranded ribonucleic acid molecule of claim 7, wherein the 3' overhang comprises nucleotides linked by one or more phosphorothioate groups.

9. The double-stranded ribonucleic acid molecule of claim 8, wherein the 3' overhang comprises uracil.

10. The double-stranded ribonucleic acid molecule of claim 1, wherein the antisense strand of the double-stranded ribonucleic acid molecule comprises at least one 2'-O-methyl modified nucleotide, at least one 2'-deoxy-2'-fluoro modified nucleotide, and at least one nucleotide comprising a 5'-phosphorothioate group.

11. The double-stranded ribonucleic acid molecule of claim 1, wherein the sense strand of the double-stranded ribonucleic acid molecule comprises at least one 2'-O-methyl modified nucleotide, at least one 2'-deoxy-2'-fluoro modified nucleotide, and at least one nucleotide comprising a 5'-phosphorothioate group.

12. The double-stranded ribonucleic acid molecule of claim 6, wherein the sense strand and the antisense strand of the double-stranded ribonucleic acid molecule each comprises at least one 2'-O-methyl modified nucleotide, at least one 2'-deoxy-2'-fluoro modified nucleotide, and at least one nucleotide comprising a 5'-phosphorothioate group.

13. The double-stranded ribonucleic acid molecule of claim 1, wherein the double-stranded ribonucleotic acid molecule is conjugated to a ligand.

14. The double-stranded ribonucleic acid molecule of claim 6, wherein said double-stranded ribonucleotic acid molecule is conjugated to a ligand.

15. The double stranded ribonucleic acid molecule of claim 1, wherein the antisense strand comprises any of SEQ ID NO: 717, 779, 837, 810, 826, 811, 752, or 743.

16. The double stranded ribonucleic acid molecule of claim 6, wherein the sense strand comprises any of SEQ ID NO: 537, 569, 589, 607, 618, 632, 644 or 663.

17. The double stranded ribonucleic acid molecule of claim 6, wherein the antisense strand comprises any of SEQ ID NO: 717, 779, 837, 810, 826, 811, 752, or 743, and wherein the sense strand comprises any of SEQ ID NO: 467 537, 569, 589, 607, 618, 632, 644 or 663.

18. The double-stranded ribonucleic acid molecule of claim 15, wherein the double-stranded ribonucleotic acid molecule is conjugated to a ligand.

19. The double-stranded ribonucleic acid molecule of claim 17, wherein the double-stranded ribonucleotic acid molecule is conjugated to a ligand.

20. A pharmaceutical composition comprising: (i) the double-stranded ribonucleic acid molecule of claim 1, and (ii) a pharmaceutically acceptable carrier.

21. A pharmaceutical composition comprising: (i) the double-stranded ribonucleic acid molecule of claim 6, and (ii) a pharmaceutically acceptable carrier.

* * * * *

SEQUENCE LISTING

<160> NUMBER OF SEQ ID NOS: 1015

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uuguggcaga cagacuuau                                              19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ccugauguuc aaacaccug                                              19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aguccaacag agaauucuu                                              19

```
<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uaggcgagua ucagaggau                                              19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggcgaguauc agaggaugg                                              19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uguucaaaca ccugguaca                                              19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggugacccu uuagugagc                                              19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gaaggaaaga cuacuucu                                               19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uucugaaaug uauagucuu                                              19
```

```
<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cuguguagcu accucacaa                                                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ugcacucuaa ugaagcaau                                                    19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cccauuugac uuuauggag                                                    19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aaauguauag ucuucuuau                                                    19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uacauugagu uuguggcag                                                    19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
caauacauug aguuugugg                                                    19
```

```
<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gaacaggagu uccucacug                                                    19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aucccauguu cuggcuuuc                                                    19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
guagguugug ugaguuaau                                                    19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
auagucuucu uauugacac                                                    19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
auugcacucu aaugaagca                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuaucaaugc uguucggau                                                    19

<210> SEQ ID NO 22
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
agaaacgagg acugaugcc                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cauugaguuu guggcagac                                                    19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
acauucagca cugggaauc                                                    19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ugauguucaa acaccuggu                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ggauagaaca ggaguuccu                                                    19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aauauuucac uggaaggaa                                                    19

<210> SEQ ID NO 28
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aauaaacauu guuuguacu                                                    19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucccauguuc uggcuuucu                                                    19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uucggauaga acaggaguu                                                    19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aaguagguug ugugaguua                                                    19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uuauagugcu gguaguauc                                                    19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cuucuuauug acacuuaca                                                    19

<210> SEQ ID NO 34
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 34
uacagaagcc cgcuguuuc                                                    19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gugacccuuu agugagcuu                                                    19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
auagaacagg aguuccuca                                                    19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cuggcacuuu acaaacaaa                                                    19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucuaaugaag caauacauu                                                    19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucuucuuauu gacacuuac                                                    19

<210> SEQ ID NO 40
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 40
uguucggaua gaacaggag                                                    19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
aguaccauga uaucuggca                                                    19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cagagaugag gguuuacac                                                    19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gaaacgagga cugaugccu                                                    19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
aagagaguag gcgaguauc                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cauuagcuga auaauguga                                                    19

<210> SEQ ID NO 46
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 46
aguagagaac ccauuugac                                                 19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aggcgaguau cagaggaug                                                 19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uagacuaagc auguaauuu                                                 19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aacauuguuu guacucaca                                                 19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gaugggagug augucaagu                                                 19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cagaccauuu ccuaaucag                                                 19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 52
gauuacagaa gcccgcugu                                                    19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cauugaaacg augccuugu                                                    19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
acuuaugcug gaacugggu                                                    19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gucgacaagg agaacacgc                                                    19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
aggaaagacu aacuucuuu                                                    19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
caagaccgcg aggaggauc                                                    19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gacaauggca gucuuggcu					19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
augccuugug ucaagaaga					19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gccucacugc uucaacgca					19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uaccucacaa ccaguccug					19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gagaagagag uaggcgagu					19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
agacuuaugc uggaacugg					19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 64
uuacagaagc ccgcuguuu                                                    19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uuaugcugga acugguuu                                                     19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
auaaacauug uuuguacuc                                                    19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ucaaugccau ugaaacgau                                                    19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
auagugcugg uaguaucac                                                    19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cagccucacu gcuucaacg                                                    19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
```
ucuuggcuuu aaagugagg                                               19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ggcugugacu uaccauagc                                               19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ggcuaccuau ggugaacgu                                               19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
cgcgaggagg aucuuccag                                               19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gccauugaaa cgaugccuu                                               19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
agccucacug cuucaacgc                                               19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76

```
ggcagacaga cuuaugcug                                               19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gugacuaaag uaaguuaaa                                               19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aguuauuguu accuaaagu                                               19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gccuuuaugu uugggagaa                                               19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uucagaguag agaacccau                                               19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
aaacgaggac ugaugccug                                               19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
guaggcgagu aucagagga                                               19
```

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
aagcccgcug uuucuaugg                                                19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ucagcacugg gaaucccug                                                19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gaauaaugug aggauuaac                                                19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uguggcagac agacuuaug                                                19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
agagauaaau guugaucuu                                                19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uaccaugaua ucuggcaga                                                19

```
<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cuuccaaauu gccauggaa                                                      19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
accgcgagga ggaucuucc                                                      19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gaaauguaua gucuucuua                                                      19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auguucaaac accugguac                                                      19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
agggaauuuc ucuucaaug                                                      19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cccuguuaag uggugaaau                                                      19
```

```
<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gaugaggguu uacacugug                                                19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ugugugaguu aauucauuu                                                19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uugccugaug uucaaacac                                                19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aaacuugugu agacuaagc                                                19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uauauuccau guucuggcu                                                19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uuguguagac uaagcaugu                                                19

<210> SEQ ID NO 101
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
augcuguucg gauagaaca                                                       19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aauuaucaau gcuguucgg                                                       19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gccugauguu caaacaccu                                                       19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
cauagcagug acaauggca                                                       19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ugugaguuaa uucauuuau                                                       19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
agugcuggua guaucaccu                                                       19

<210> SEQ ID NO 107
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uaucaaugcu guucggaua                                                19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gacuaaagua aguuaaacu                                                19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
aaugcuguuc ggauagaac                                                19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
agaauauuuc acuggaagg                                                19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aucuggcaga uguauaaga                                                19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uauagugcug guaguauca                                                19

<210> SEQ ID NO 113
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 113
ggccagcaag accgcgagg                                              19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ccaugauauc uggcagaug                                              19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuaaacuugu guagacuaa                                              19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uucaaugcca uugaaacga                                              19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
agaaagcuga gacauugca                                              19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cuauggcuuc caaauugcc                                              19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
aagugacuaa aguaaguua                                                   19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ugacuaaagu aaguuaaac                                                   19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
ugcuguucgg auagaacag                                                   19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gcgaguauca gaggaugggg                                                  19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gggccuugcg cuggauugg                                                   19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
accucacaac caguccugu                                                   19

<210> SEQ ID NO 125
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 125
acuaagugac uaaaguaag                                                19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
auuacagaag cccgcuguu                                                19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gaguaggcga guaucagag                                                19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
cagugacaau ggcagucuu                                                19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ggccuugcgc uggauuggg                                                19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
uucuuauuga cacuuacau                                                19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 131
uucacuaagu gacuaaagu                                                19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gugugaguua auucauuua                                                19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
cccgcucgcg cccaucacg                                                19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
guaaguuaaa cuuguguag                                                19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
cggaaguugg aaucagguu                                                19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
augugaggau uaacuucug                                                19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uuaaguggug aaaucaacu                                                        19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uguagacuaa gcauguaau                                                        19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
auaaugugag gauuaacuu                                                        19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ggcuggcugu gacuuacca                                                        19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
aagaggcuac cuaugguga                                                        19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
cagauuacag aagcccgcu                                                        19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ugaggccuug ccugugaag                                                    19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
auaauuauca augcuguuc                                                    19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gugacuuacc auagcagug                                                    19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
uagggcuacu uugaauuaa                                                    19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uggcagaugu auaagaagg                                                    19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
auagcuugau uuauuuggu                                                    19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
cagcaagacc gcgaggagg                                                19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gacugaugcc uggccucac                                                19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uuaccuugga ugcugacuu                                                19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
auucagcacu gggaauccc                                                19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
agcaagaccg cgaggagga                                                19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
agggcuacuu ugaauuaau                                                19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155

```
uaaguuauug uuaccuaaa                                              19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uuuauagugc ugguaguau                                              19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
gcaagaccgc gaggaggau                                              19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ucuauggcuu ccaaauugc                                              19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aaagacuaac uucuuugag                                              19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
accaugauau cuggcagau                                              19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gaccauuucc uaaucaguu                                              19
```

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uuaccauagc agugacaau                                                19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
aaugugagga uuaacuucu                                                19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
uaguguccug ggauucucu                                                19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uguuaagugg ugaaaucaa                                                19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
acaaauauuc uuaauaggg                                                19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gcggaaguug gaaucaggu                                                19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aacuugugua gacuaagca                                                19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
auucuuaaua gggcuacuu                                                19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ccuaaaguua auccagauu                                                19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uauuguuacc uaaaguuaa                                                19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gugcugguag uaucaccuu                                                19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cugugacuua ccauagcag                                                19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
gagcuucuua aguuaaauc                                                19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175 cguucggau agaacagga                                                 19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
guuauuguua ccuaaaguu                                                19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uaaugugagg auuaacuuc                                                19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
accacuaaug ggagccaau                                                19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uguguagacu aagcaugua                                                19

<210> SEQ ID NO 180

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ugggccuugc gcuggauug                                                      19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
aggagcuucu uaaguuaaa                                                      19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ggugacccuu uagugagcu                                                      19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
agaguaggcg aguaucaga                                                      19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gcagugacaa uggcagucu                                                      19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aaacgaugcc uugugucaa                                                      19

<210> SEQ ID NO 186
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ggacugaugc cuggccuca                                                  19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
ugagagauaa auguugauc                                                  19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ugguuucuac accaaauac                                                  19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
ucucuguaau augauacau                                                  19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gagagauaaa uguugaucu                                                  19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
acucuaauga agcaauaca                                                  19

<210> SEQ ID NO 192
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 192
ugaaguguua ccaacuagc                                              19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
aaugaagcaa uacauugag                                              19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
acgaugccuu gugucaaga                                              19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
agaccgcgag gaggaucuu                                              19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uuguuaccua aaguuaauc                                              19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
cagaagcccg cuguuucua                                              19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uuugacuuua uggagaaua                                                      19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uaccuaaagu uaauccaga                                                      19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uucaaacacc ugguacaca                                                      19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uugcacucua augaagcaa                                                      19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uguuaccuaa aguuaaucc                                                      19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
cacuaaguga cuaaaguaa                                                      19

<210> SEQ ID NO 204
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 204
ugccagauag aagacaggu                                                  19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
aauguauagu cuucuuauu                                                  19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
gaccacuaau gggagccaa                                                  19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
guuaccuaaa guuaaucca                                                  19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
ugaugccugg ccucacauu                                                  19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ccaacuuuaa agucagucc                                                  19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 210
uaaacuugug uagacuaag         19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
aguagguugu gugaguuaa         19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
guuaaacuug uguagacua         19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
cugaccacua augggagcc         19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
uauucuuaau agggcuacu         19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
guaguguccu gggauucuc         19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 216
uaucuggcag auguauaag                                                19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
aggcuaccua uggugaacg                                                19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ucagaccauu uccuaauca                                                19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uuaccuaaag uuaauccag                                                19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gguuucuaca ccaaauaca                                                19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
guuggugcca gauagaaga                                                19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 222
gcuaccuaug gugaacgug                                              19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ucacuaagug acuaaagua                                              19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uuauuguuac cuaaaguua                                              19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
uagcugaaua augugagga                                              19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ugaccacuaa ugggagcca                                              19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
guagcuaccu cacaaccag                                              19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
```
ucccgcucgc gcccaucac                                              19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
cuuggcuuua aagugaggg                                              19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
agaagcccgc uguuucuau                                              19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
acuaaaguaa guuaaacuu                                              19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
aguaaguuaa acuugugua                                              19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
aauaauuauc aaugcuguu                                              19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
auaagucugu cugccacaa                                                19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
cagguguuug aacaucagg                                                19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
aagaauucuc uguuggacu                                                19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
auccucugau acucgccua                                                19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
ccauccucug auacucgcc                                                19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
uguaccaggu guuugaaca                                                19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
gcucacuaaa gggucaccc                                                19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
agaaguuagu cuuccuuc                                              19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
aagacuauac auuucagaa                                             19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uugugaggua gcuacacag                                             19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
auugcuucau uagagugca                                             19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
cuccauaaag ucaaauggg                                             19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
auaagaagac uauacauuu                                             19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
cugccacaaa cucaaugua                                                19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
ccacaaacuc aauguauug                                                19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
cagugaggaa cuccuguuc                                                19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gaaagccaga acaugggau                                                19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
auuaacucac acaaccuac                                                19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gugucaauaa gaagacuau                                                19

```
<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ugcuucauua gagugcaau                                                   19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
auccgaacag cauugauaa                                                   19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ggcaucaguc cucguuucu                                                   19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gucugccaca aacucaaug                                                   19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gauucccagu gcugaaugu                                                   19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
accagguguu ugaacauca                                                   19

<210> SEQ ID NO 259
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
aggaacuccu guucuaucc                                                  19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uuccuuccag ugaaauauu                                                  19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aguacaaaca auguuuauu                                                  19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
agaaagccag aacauggga                                                  19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
aacuccuguu cuauccgaa                                                  19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uaacucacac aaccuacuu                                                  19

<210> SEQ ID NO 265
<211> LENGTH: 19
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gauacuacca gcacuauaa                                                    19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
uguaaguguc aauaagaag                                                    19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gaaacagcgg gcuucugua                                                    19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
aagcucacua aagggucac                                                    19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ugaggaacuc cuguucuau                                                    19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
uuuguuugua aagugccag                                                    19

<210> SEQ ID NO 271
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 271
aauguauugc uucauuaga                                                   19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
guaaguguca auaagaaga                                                   19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
cuccuguucu auccgaaca                                                   19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ugccagauau caugguacu                                                   19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
guguaaaccc ucaucucug                                                   19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
aggcaucagu ccucguuuc                                                   19

<210> SEQ ID NO 277
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 277
gauacucgcc uacucucuu                                                   19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
ucacauuauu cagcuaaug                                                   19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gucaaauggg uucucuacu                                                   19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
cauccucuga uacucgccu                                                   19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
aaauuacaug cuuagucua                                                   19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ugugaguaca aacaauguu                                                   19

<210> SEQ ID NO 283
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 283
acuugacauc acucccauc                                                  19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
cugauuagga aauggucug                                                  19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
acagcgggcu ucuguaauc                                                  19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
acaaggcauc guuucaaug                                                  19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
acccaguucc agcauaagu                                                  19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
gcguguucuc cuugucgac                                                  19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 289
aaagaaguua gucuuuccu                                                    19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gauccuccuc gcggucuug                                                    19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
agccaagacu gccauuguc                                                    19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ucuucuugac acaaggcau                                                    19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ugcguugaag cagugaggc                                                    19

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
caggacuggu ugugaggua                                                    19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
acucgccuac ucucuucuc                                            19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
ccaguuccag cauaagucu                                            19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
aaacagcggg cuucuguaa                                            19

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aaacccaguu ccagcauaa                                            19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
gaguacaaac aauguuuau                                            19

<210> SEQ ID NO 300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
aucguuucaa uggcauuga                                            19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 301
gugauacuac cagcacuau                                                    19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
cguugaagca gugaggcug                                                    19

<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ccucacuuua aagccaaga                                                    19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gcuaugguaa gucacagcc                                                    19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
acguucacca uagguagcc                                                    19

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
cuggaagauc cuccucgcg                                                    19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
```
aaggcaucgu uucaauggc                                         19

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
gcguugaagc agugaggcu                                         19

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
cagcauaagu cugucugcc                                         19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uuuaacuuac uuuagucac                                         19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
acuuuaggua acaauaacu                                         19

<210> SEQ ID NO 312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uucucccaaa cauaaaggc                                         19

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
auggguucuc uacucugaa					19

<210> SEQ ID NO 314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
caggcaucag uccucguuu					19

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
uccucugaua cucgccuac					19

<210> SEQ ID NO 316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
ccauagaaac agcgggcuu					19

<210> SEQ ID NO 317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
cagggauucc cagugcuga					19

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
guuaauccuc acauuauuc					19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
cauaagucug ucugccaca					19

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
aagaucaaca uuuaucucu                                                  19

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
ucugccagau aucauggua                                                  19

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uuccauggca auuuggaag                                                  19

<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
ggaagauccu ccucgcggu                                                  19

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uaagaagacu auacauuuc                                                  19

<210> SEQ ID NO 325
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
guaccaggug uuugaacau                                                  19

```
<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
cauugaagag aaauuccc u                                              19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
auuucaccac uuaacaggg                                               19

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
cacaguguaa acccucauc                                               19

<210> SEQ ID NO 329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
aaaugaauua acucacaca                                               19

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
guguuugaac aucaggcaa                                               19

<210> SEQ ID NO 331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
gcuuagucua cacaaguuu                                               19
```

-continued

```
<210> SEQ ID NO 332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
agccagaaca ugggauaua                                                  19

<210> SEQ ID NO 333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
acaugcuuag ucuacacaa                                                  19

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
uguucuaucc gaacagcau                                                  19

<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
ccgaacagca uugauaauu                                                  19

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
agguguuuga acaucaggc                                                  19

<210> SEQ ID NO 337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
ugccauuguc acugcuaug                                                  19

<210> SEQ ID NO 338
```

-continued

<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
auaaaugaau uaacucaca                                                   19

<210> SEQ ID NO 339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
aggugauacu accagcacu                                                   19

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
uauccgaaca gcauugaua                                                   19

<210> SEQ ID NO 341
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
aguuuaacuu acuuuaguc                                                   19

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342 guucuaccg aacagcauu                                                    19

<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ccuuccagug aaauauucu                                                   19

<210> SEQ ID NO 344
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
ucuuauacau cugccagau                                                      19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
ugauacuacc agcacuaua                                                      19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
ccucgcgguc uugcuggcc                                                      19

<210> SEQ ID NO 347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
caucugccag auaucaugg                                                      19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348 uuagcuaca caaguuuaa                                                       19

<210> SEQ ID NO 349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ucguuucaau ggcauugaa                                                      19

<210> SEQ ID NO 350
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 350
ugcaaugucu cagcuuucu                                                       19

<210> SEQ ID NO 351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ggcaauuugg aagccauag                                                       19

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uaacuuacuu uagucacuu                                                       19

<210> SEQ ID NO 353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
guuuaacuua cuuuaguca                                                       19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
cuguucuauc cgaacagca                                                       19

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
cccauccucu gauacucgc                                                       19

<210> SEQ ID NO 356
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 356
ccaauccagc gcaaggccc                                                  19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
acaggacugg uugugaggu                                                  19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
cuuacuuuag ucacuuagu                                                  19

<210> SEQ ID NO 359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
aacagcgggc uucuguaau                                                  19

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
cucugauacu cgccuacuc                                                  19

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
aagacugcca uugucacug                                                  19

<210> SEQ ID NO 362
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 362
cccaauccag cgcaaggcc                                                   19

<210> SEQ ID NO 363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
auguaagugu caauaagaa                                                   19

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
acuuuaguca cuuagugaa                                                   19

<210> SEQ ID NO 365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uaaaugaauu aacucacac                                                   19

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
cgugaugggc gcgagcggg                                                   19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
cuacacaagu uuaacuuac                                                   19

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 368
aaccugauuc caacuuccg                                                19

<210> SEQ ID NO 369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
cagaaguuaa uccucacau                                                19

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
aguugauuuc accacuuaa                                                19

<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
auuacaugcu uagucuaca                                                19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aaguuaaucc ucacauuau                                                19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
ugguaaguca cagccagcc                                                19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 374
ucaccauagg uagccucuu                                              19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
agcgggcuuc uguaaucug                                              19

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
cuucacaggc aaggccuca                                              19

<210> SEQ ID NO 377
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gaacagcauu gauaauuau                                              19

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
uuaauucaaa guagcccua                                              19

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ccuucuuaua caucugcca                                              19

<210> SEQ ID NO 380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 380
accaaauaaa ucaagcuau                                              19

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
ccuccucgcg gucuugcug                                              19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
gugaggccag gcaucaguc                                              19

<210> SEQ ID NO 383
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
aagucagcau ccaagguaa                                              19

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
gggauuccca gugcugaau                                              19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uccuccucgc ggucuugcu                                              19

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
```
auuaauucaa aguagcccu					19

<210> SEQ ID NO 387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
uuuagguaac aauaacuua					19

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
auacuaccag cacuauaaa					19

<210> SEQ ID NO 389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
auccuccucg cggucuugc					19

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
gcaauuugga agccauaga					19

<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
cucaaagaag uuagucuuu					19

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392

-continued aucugccaga uaucauggu					19

<210> SEQ ID NO 393
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aacugauuag gaaaugguc					19

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
auugucacug cuaugguaa					19

<210> SEQ ID NO 395
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
agaaguuaau ccucacauu					19

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
agagaauccc aggacacua					19

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uugauuucac cacuuaaca					19

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
cccuauuaag aauauuugu					19

<210> SEQ ID NO 399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
accugauucc aacuuccgc                                                 19

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ugcuuagucu acacaaguu                                                 19

<210> SEQ ID NO 401
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aaguagcccu auuaagaau                                                 19

<210> SEQ ID NO 402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
aaucuggauu aacuuuagg                                                 19

<210> SEQ ID NO 403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uuaacuuuag guaacaaua                                                 19

<210> SEQ ID NO 404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
aaggugauac uaccagcac                                                 19

-continued

<210> SEQ ID NO 405
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
cugcuauggu aagucacag                                                19

<210> SEQ ID NO 406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
gauuuaacuu aagaagcuc                                                19

<210> SEQ ID NO 407
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
uccuguucua uccgaacag                                                19

<210> SEQ ID NO 408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
aacuuuaggu aacaauaac                                                19

<210> SEQ ID NO 409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
gaaguuaauc cucacauua                                                19

<210> SEQ ID NO 410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
auuggcuccc auuaguggu                                                19

```
<210> SEQ ID NO 411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
uacaugcuua gucuacaca                                                19

<210> SEQ ID NO 412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412 cauccagcg caaggccca                                                 19

<210> SEQ ID NO 413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uuuaacuuaa gaagcuccu                                                19

<210> SEQ ID NO 414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
agcucacuaa agggucacc                                                19

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
ucugauacuc gccuacucu                                                19

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
agacugccau ugucacugc                                                19

<210> SEQ ID NO 417
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uugacacaag gcaucguuu                                                19

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
ugaggccagg caucagucc                                                19

<210> SEQ ID NO 419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
gaucaacauu uaucucuca                                                19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
guauuuggug uagaaacca                                                19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
auguaucaua uuacagaga                                                19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
agaucaacau uuaucucuc                                                19

<210> SEQ ID NO 423
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
uguauugcuu cauuagagu                                                      19

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
gcuaguuggu aacacuuca                                                      19

<210> SEQ ID NO 425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
cucaauguau ugcuucauu                                                      19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
ucuugacaca aggcaucgu                                                      19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
aagauccucc ucgcggucu                                                      19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gauuaacuuu agguaacaa                                                      19

<210> SEQ ID NO 429
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 429
uagaaacagc gggcuucug                                                    19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
uauucuccau aaagucaaa                                                    19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
ucuggauuaa cuuuaggua                                                    19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uguguaccag guguuugaa                                                    19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uugcuucauu agagugcaa                                                    19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ggauuaacuu uagguaaca                                                    19

<210> SEQ ID NO 435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
uuacuuuagu cacuuagug                                                    19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
accugucuuc uaucuggca                                                    19

<210> SEQ ID NO 437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
aauaagaaga cuauacauu                                                    19

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
uuggcuccca uuagugguc                                                    19

<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
uggauuaacu uuagguaac                                                    19

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
aaugugaggc caggcauca                                                    19

<210> SEQ ID NO 441
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 441
ggacugacuu uaaaguugg                                                       19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
cuuagucuac acaaguuua                                                       19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uuaacucaca caaccuacu                                                       19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
uagucuacac aaguuuaac                                                       19

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ggcucccauu aguggucag                                                       19

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
aguagcccua uuaagaaua                                                       19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 447
gagaauccca ggacacuac                              19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
cuuauacauc ugccagaua                              19

<210> SEQ ID NO 449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
cguucaccau agguagccu                              19

<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ugauuaggaa auggucuga                              19

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
cuggauuaac uuuagguaa                              19

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
uguauuuggu guagaaacc                              19

<210> SEQ ID NO 453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
ucuucuaucu ggcaccaac						19

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
cacguucacc auagguagc						19

<210> SEQ ID NO 455
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
uacuuuaguc acuuaguga						19

<210> SEQ ID NO 456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
uaacuuuagg uaacaauaa						19

<210> SEQ ID NO 457
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
uccucacauu auucagcua						19

<210> SEQ ID NO 458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uggcucccau uagugguca						19

<210> SEQ ID NO 459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 459
cugguuguga gguagcuac                                          19

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
gugaugggcg cgagcggga                                          19

<210> SEQ ID NO 461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
cccucacuuu aaagccaag                                          19

<210> SEQ ID NO 462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
auagaaacag cgggcuucu                                          19

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
aaguuuaacu uacuuuagu                                          19

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
uacacaaguu uaacuuacu                                          19

<210> SEQ ID NO 465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
```

-continued aacagcauug auaauuauu 19

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
cacugcuaug guaagucac 19

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
uuguggcaga cagacuuaut t 21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
ccugauguuc aaacaccugt t 21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
aguccaacag agaauucuut t 21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
aguccaacag agaauucuut t 21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
uaggcgagua ucagaggaut t                                              21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
ggcgaguauc agaggauggt t                                              21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
uguucaaaca ccugguacat t                                              21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
gggugacccu uuagugagct t                                              21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
gaaggaaaga cuaacuucut t                                    21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
gaaggaaaga cuaacuucut t                                    21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
uucugaaaug uauagucuut t                                    21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
cuguguagcu accucacaat t                                    21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
ugcacucuaa ugaagcaaut t                                    21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 480
cccauuugac uuuauggagt t                                              21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
aaauguauag ucuucuuaut t                                              21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
uacauugagu uguggcagt t                                               21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
caauacauug aguuuguggt t                                              21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
gaacaggagu uccucacugt t                                              21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
aucccauguu cuggcuuuct t                                                21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
guagguugug ugaguuaaut t                                                21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
auagucuucu uauugacact t                                                21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
auugcacucu aaugaagcat t                                                21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
uuaucaaugc uguucggaut t                                                21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 490
agaaacgagg acugaugcct t                                              21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
cauugaguuu guggcagact t                                              21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
acauucagca cugggaauct t                                              21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
ugauguucaa acaccuggut t                                              21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
ggauagaaca ggaguuccut t                                              21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 495
aauauuucac uggaaggaat t                                              21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
aauaaacauu guuuguacut t                                              21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
ucccauguuc uggcuuucut t                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
uucggauaga acaggaguut t                                              21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
aaguagguug ugugaguuat t                                              21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 500
uuauagugcu gguaguauct t                                                     21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
cuucuuauug acacuuacat t                                                     21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
uacagaagcc cgcuguuuct t                                                     21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
gugacccuuu agugagcuut t                                                     21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
auagaacagg aguuccucat t                                                     21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 505
cuggcacuuu acaaacaaat t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
ucuaaugaag caauacauut t                                              21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
ucuucuuauu gacacuuact t                                              21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
ucuucuuauu gacacuuact t                                              21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
uguucggaua gaacaggagt t                                              21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 510
aguaccauga uaucuggcat t                                              21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
cagagaugag gguuuacact t                                              21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
gaaacgagga cugaugccut t                                              21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
aagagaguag gcgaguauct t                                              21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
cauuagcuga auaaugugat t                                              21

<210> SEQ ID NO 515
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 515
aguagagaac ccauuugact t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 516
aggcgaguau cagaggaugt t                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 517
uagacuaagc auguaauuut t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 518
aacauuguuu guacucacat t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 519
gaugggagug augucaagut t                                              21

<210> SEQ ID NO 520
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
cagaccauuu ccuaaucagt t                                            21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
gauuacagaa gcccgcugut t                                            21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
cauugaaacg augccuugut t                                            21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
acuuaugcug gaacugggut t                                            21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
gucgacaagg agaacacgct t                                            21

<210> SEQ ID NO 525
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
aggaaagacu aacuucuuut t                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
aggaaagacu aacuucuuut t                                              21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
caagaccgcg aggaggauct t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
gacaauggca gucuuggcut t                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
augccuugug ucaagaagat t                                              21

<210> SEQ ID NO 530
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
gccucacugc uucaacgcat t                                            21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
uaccucacaa ccaguccugt t                                            21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
gagaagagag uaggcgagut t                                            21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
agacuuaugc uggaacuggt t                                            21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
uuacagaagc ccgcuguuut t                                            21

<210> SEQ ID NO 535
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
uuaugcugga acuggguuut t                                              21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
auaaacauug uuuguacuct t                                              21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
ucaaugccau ugaaacgaut t                                              21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
auagugcugg uaguaucact t                                              21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
cagccucacu gcuucaacgt t                                              21
```

```
<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
ucuuggcuuu aaagugaggt t                                                   21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
ggcugugacu uaccauagct t                                                   21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
ggcuaccuau ggugaacgut t                                                   21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
cgcgaggagg aucuuccagt t                                                   21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
gccauugaaa cgaugccuut t                                                   21
```

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 545
agccucacug cuucaacgct t                                               21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 546
ggcagacaga cuuaugcugt t                                               21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 547
gugacuaaag uaaguuaaat t                                               21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 548
aguuauuguu accuaaagut t                                               21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 549
gccuuuaugu uugggagaat t                                               21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 550
uucagaguag agaacccaut t                                              21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 551
aaacgaggac ugaugccugt t                                              21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 552
guaggcgagu aucagaggat t                                              21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 553
guaggcgagu aucagaggat t                                              21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 554
aagcccgcug uuucuauggt t                                              21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
ucagcacugg gaaucccugt t                                              21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 556
gaauaaugug aggauuaact t                                              21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 557
uguggcagac agacuuaugt t                                              21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
agagauaaau guugaucuut t                                              21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 559
uaccaugaua ucuggcagat t				21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
cuuccaaauu gccauggaat t				21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 561
accgcgagga ggaucuucct t				21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
gaaauguaua gucuucuuat t				21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
auguucaaac accugguact t				21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 564
agggaauuuc ucuucaaugt t                                               21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
cccuguuaag uggugaaaut t                                               21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
gaugaggguu uacacugugt t                                               21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
ugugugaguu aauucauuut t                                               21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
uugccugaug uucaaacact t                                               21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 569
aaacuugugu agacuaagct t                                              21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570 uauauacccau guucuggcut t                                             21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
uuguguagac uaagcaugut t                                              21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
augcuguucg gauagaacat t                                              21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
aauuaucaau gcuguucggt t                                              21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 574
gccugauguu caaacaccut t          21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
cauagcagug acaauggcat t          21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
ugugaguuaa uucauuuaut t          21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
agugcuggua guaucaccut t          21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
uaucaaugcu guucggauat t          21

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 579
gacuaaagua aguuaaacut t                                              21

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
aaugcuguuc ggauagaact t                                              21

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
agaauauuuc acuggaaggt t                                              21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide

<400> SEQUENCE: 582
aucuggcaga uguauaagat t                                              21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
uauagugcug guaguaucat t                                              21

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Description of Combined DNA/RNA Molecule:
      Synthetic oligonucleotide

<400> SEQUENCE: 584
ggccagcaag accgcgaggt t                                              21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
ccaugauauc uggcagaugt t                                              21

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
uuaaacuugu guagacuaat t                                              21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
uucaaugcca uugaaacgat t                                              21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
agaaagcuga gacauugcat t                                              21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 589
cuauggcuuc caaauugcct t                                              21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590
aagugacuaa aguaaguuat t                                              21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
ugacuaaagu aaguuaaact t                                              21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
ugcuguucgg auagaacagt t                                              21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
gcgaguauca gaggaugggt t                                              21

<210> SEQ ID NO 594
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
gggccuugcg cuggauuggt t                                              21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
accucacaac caguccugut t                                              21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
acuaagugac uaaaguaagt t                                              21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
auuacagaag cccgcuguut t                                              21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
gaguaggcga guaucagagt t                                              21

<210> SEQ ID NO 599
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
cagugacaau ggcagucuut t                                           21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
ggccuugcgc uggauugggt t                                           21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
uucuuauuga cacuuacaut t                                           21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
uucacuaagu gacuaaagut t                                           21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
gugugaguua auucauuuat t                                           21

<210> SEQ ID NO 604
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 604
cccgcucgcg cccaucacgt t                                              21

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 605
guaaguuaaa cuuguguagt t                                              21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 606
cggaaguugg aaucagguut t                                              21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 607
augugaggau uaacuucugt t                                              21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 608
uuaaguggug aaaucaacut t                                              21

<210> SEQ ID NO 609
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 609
uguagacuaa gcauguaaut t                                            21

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
auaaugugag gauuaacuut t                                            21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
ggcuggcugu gacuuaccat t                                            21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 612
aagaggcuac cuauggugat t                                            21

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 613
cagauuacag aagcccgcut t                                            21

<210> SEQ ID NO 614
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
ugaggccuug ccugugaagt t                                           21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 615
auaauuauca augcuguuct t                                           21

<210> SEQ ID NO 616
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
gugacuuacc auagcagugt t                                           21

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
uagggcuacu uugaauuaat t                                           21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618
uggcagaugu auaagaaggt t                                           21
```

```
<210> SEQ ID NO 619
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
auagcuugau uuauuuggut t                                              21

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
cagcaagacc gcgaggaggt t                                              21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
gacugaugcc uggccucact t                                              21

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 622
uuaccuugga ugcugacuut t                                              21

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
auucagcacu gggaauccct t                                              21
```

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 624
agcaagaccg cgaggaggat t                                             21

<210> SEQ ID NO 625
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 625
agggcuacuu ugaauuaaut t                                             21

<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 626
uaaguuauug uuaccuaaat t                                             21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 627
uuuauagugc ugguaguaut t                                             21

<210> SEQ ID NO 628
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 628
gcaagaccgc gaggaggaut t                                             21

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 629
ucuauggcuu ccaaauugct t     21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 630
aaagacuaac uucuuugagt t     21

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 631
accaugauau cuggcagaut t     21

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 632
gaccauuccc uaaucaguut t     21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 633
uuaccauagc agugacaaut t                                              21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 634
aaugugagga uuaacuucut t                                              21

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 635
uaguguccug ggauucucut t                                              21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 636
uguuaagugg ugaaaucaat t                                              21

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 637
acaaauauuc uuaauagggt t                                              21

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 638

```
gcggaaguug gaaucaggut t                                              21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 639
aacuugugua gacuaagcat t                                              21

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 640
auucuuaaua gggcuacuut t                                              21

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 641
ccuaaaguua auccagauut t                                              21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 642
uauuguuacc uaaaguuaat t                                              21

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 643
gugcugguag uaucaccuut t                                              21

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
cugugacuua ccauagcagt t                                              21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 645
gagcuucuua aguuaaauct t                                              21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 646
cuguucggau agaacaggat t                                              21

<210> SEQ ID NO 647
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647
guuauuguua ccuaaaguut t                                              21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 648
uaaugugagg auuaacuuct t                                              21

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
accacuaaug ggagccaaut t                                              21

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650
uguguagacu aagcauguat t                                              21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
ugggccuugc gcuggauugt t                                              21

<210> SEQ ID NO 652
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 652
aggagcuucu uaaguuaaat t                                              21

<210> SEQ ID NO 653
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 653
ggugacccuu uagugagcut t                                              21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
agaguaggcg aguaucagat t                                              21

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
gcagugacaa uggcagucut t                                              21

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
aaacgaugcc uugugucaat t                                              21

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 657
ggacugaugc cuggccucat t                                              21

<210> SEQ ID NO 658
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 658
ugagagauaa auguugauct t                                                 21

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
ugguuucuac accaaauact t                                                 21

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
ucucuguaau augauacaut t                                                 21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
gagagauaaa uguugaucut t                                                 21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
acucuaauga agcaauacat t                                                 21

<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 663
ugaaguguua ccaacuagct t                                              21

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
aaugaagcaa uacauugagt t                                              21

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
acgaugccuu gugucaagat t                                              21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
agaccgcgag gaggaucuut t                                              21

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 667
uuguuaccua aaguuaauct t                                              21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 668
cagaagcccg cguuucuat t                                              21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
uuugacuuua uggagaauat t                                             21

<210> SEQ ID NO 670
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 670
uaccuaaagu uaauccagat t                                             21

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
uucaaacacc ugguacacat t                                             21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
uugcacucua augaagcaat t                                             21

<210> SEQ ID NO 673
<211> LENGTH: 21
<212> TYPE: DNA
<213> ORGANISM: Artificial Sequence
<220> FEATURE:

<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 673
uguuaccuaa aguuaaucct t                                              21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 674
cacuaaguga cuaaaguaat t                                              21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 675
ugccagauag aagacaggut t                                              21

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 676
aauguauagu cuucuuauut t                                              21

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 677
gaccacuaau gggagccaat t                                              21

<210> SEQ ID NO 678
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 678
guuaccuaaa guuaauccat t                                              21

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679
ugaugccugg ccucacauut t                                              21

<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
ccaacuuuaa agucagucct t                                              21

<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
uaaacuugug uagacuaagt t                                              21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
aguagguugu gugaguuaat t                                              21

<210> SEQ ID NO 683
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
guuaaacuug uguagacuat t                                              21

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
cugaccacua augggagcct t                                              21

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 685
uauucuuaau agggcuacut t                                              21

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 686
guaguguccu gggauucuct t                                              21

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 687
uaucuggcag auguauaagt t                                              21

<210> SEQ ID NO 688
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 688
aggcuaccua uggugaacgt t                                              21

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
ucagaccauu uccuaaucat t                                              21

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690
uuaccuaaag uuaauccagt t                                              21

<210> SEQ ID NO 691
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 691
gguuucuaca ccaaauacat t                                              21

<210> SEQ ID NO 692
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 692
guuggugcca gauagaagat t                                              21

<210> SEQ ID NO 693
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 693
gcuaccuaug gugaacgugt t                                                 21

<210> SEQ ID NO 694
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 694
ucacuaagug acuaaaguat t                                                 21

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 695
uuauuguuac cuaaaguuat t                                                 21

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 696
uagcugaaua augugaggat t                                                 21

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
ugaccacuaa ugggagccat t                                                 21
```

```
<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
guagcuaccu cacaaccagt t                                               21

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699
ucccgcucgc gcccaucact t                                               21

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700
cuuggcuuua aagugagggt t                                               21

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 701
agaagcccgc uguuucuaut t                                               21

<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 702
acuaaaguaa guuaaacuut t                                               21
```

<210> SEQ ID NO 703
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 703
aguaaguuaa acuuguguat t                                              21

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence:
Synthetic oligonucleotide
<220> FEATURE:
<223> OTHER INFORMATION: Description of Combined DNA/RNA Molecule:
Synthetic oligonucleotide

<400> SEQUENCE: 704
aauaauuauc aaugcuguut t                                              21

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 705
gcguguucuc cuugucgact t                                              21

<210> SEQ ID NO 706
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 706
ccucgcgguc uugcuggcct t                                              21

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 707
ccuccucgcg gucuugcugt t                                              21

<210> SEQ ID NO 708
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 708 gauuccagu gcugaaugut t                                              21

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 709
gggauuccca gugcugaaut t                                              21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 710
gaaagccaga acaugggaut t                                              21

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 711
agaaagccag aacaugggat t                                              21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 712
acagcgggcu ucuguaauct t        21

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 713
uaagaagacu auacauuuct t        21

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 714
auaagaagac uauacauuut t        21

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 715
gugucaauaa gaagacuaut t        21

<210> SEQ ID NO 716
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 716
cauugaagag aaauucccut t        21

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 717

```
aucguuucaa uggcauugat t                                              21

<210> SEQ ID NO 718
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718
aaggcaucgu uucaauggct t                                              21

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 719
uugacacaag gcaucguuut t                                              21

<210> SEQ ID NO 720
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720
ucuugacaca aggcaucgut t                                              21

<210> SEQ ID NO 721
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 721
cguucaccau agguagccut t                                              21

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 722
acguucacca uagguagcct t                                              21

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
cacguucacc auagguagct t                                              21

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 724
caggcaucag uccucguuut t                                              21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
aacagcauug auaauuauut t                                              21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 726
gaacagcauu gauaauuaut t                                              21

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 727
ccgaacagca uugauaauut t				21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
auccgaacag cauugauaat t				21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 729
guucuauccg aacagcauut t				21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 730
uguucuaucc gaacagcaut t				21

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731
cuguucuauc cgaacagcat t				21

<210> SEQ ID NO 732
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 732
uccuguucua uccgaacagt t                                              21

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
cuccuguucu auccgaacat t                                              21

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
aacuccuguu cuauccgaat t                                              21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
ugcuucauua gagugcaaut t                                              21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
uguauugcuu cauuagagut t                                              21

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 737
auaagucugu cugccacaat t                                              21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
gucaaauggg uucucuacut t                                              21

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
cuccauaaag ucaaaugggt t                                              21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 740
ccuuccagug aaauauucut t                                              21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 741
uuccuuccag ugaaauauut t                                              21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 742
aagaauucuc uguuggacut t                                                   21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
gcuaguuggu aacacuucat t                                                   21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 744
uugugaggua gcuacacagt t                                                   21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 745
caggacuggu ugugagguat t                                                   21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
gauacuacca gcacuauaat t                                                   21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 747
ugauacuacc agcacuauat t                                              21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 748
gugauacuac cagcacuaut t                                              21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
aggugauacu accagcacut t                                              21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
aaggugauac uaccagcact t                                              21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 751
gcuaugguaa gucacagcct t                                              21

<210> SEQ ID NO 752
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
cugcuauggu aagucacagt t                                                    21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
cacugcuaug guaagucact t                                                    21

<210> SEQ ID NO 754
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754 augucacug cuaugguaat t                                                     21

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide

<400> SEQUENCE: 755
agccaagacu gccauuguct t                                                    21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 756
gcucacuaaa gggucaccct t                                                    21

<210> SEQ ID NO 757
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 757
agcucacuaa agggucacct t                                            21

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 758
gcguugaagc agugaggcut t                                            21

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 759
accaaauaaa ucaagcuaut t                                            21

<210> SEQ ID NO 760
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 760
guauuuggug uagaaaccat t                                            21

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 761
uguauuuggu guagaaacct t                                            21

<210> SEQ ID NO 762
<211> LENGTH: 21
<212> TYPE: DNA
```

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 762
ggcucccauu aguggucagt t                                              21

<210> SEQ ID NO 763
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 763
uggcucccau uaguggucat t                                              21

<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 764
auuggcuccc auuaguggut t                                              21

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 765
acuuuaguca cuuagugaat t                                              21

<210> SEQ ID NO 766
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 766
uacuuuaguc acuuagugat t                                              21

<210> SEQ ID NO 767
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 767
uuacuuuagu cacuuagugt t                                              21

<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 768
cuuacuuuag ucacuuagut t                                              21

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 769
uaacuuacuu uagucacuut t                                              21

<210> SEQ ID NO 770
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 770
uuuaacuuac uuuagucact t                                              21

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 771
guuuaacuua cuuuagucat t                                              21

<210> SEQ ID NO 772
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 772
aguuuaacuu acuuuaguct t                                              21

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 773
aaguuuaacu uacuuuagut t                                              21

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 774
uacacaaguu uaacuuacut t                                              21

<210> SEQ ID NO 775
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 775
cuacacaagu uuaacuuact t                                              21

<210> SEQ ID NO 776
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 776
uagucuacac aaguuuaact t                                              21
```

```
<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 777 uuagcuaca caaguuuaat t                                              21

<210> SEQ ID NO 778
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778 cuuagcuac acaaguuuat t                                              21

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 779 gcuuagcua cacaaguuut t                                              21

<210> SEQ ID NO 780
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 780 ugcuuagcu acacaaguut t                                              21

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 781
acaugcuuag ucuacacaat t                                             21
```

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 782
uacaugcuua gucuacacat t                                              21

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 783
auuacaugcu uagucuacat t                                              21

<210> SEQ ID NO 784
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 784
aaauuacaug cuuagucuat t                                              21

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 785
ucuucuaucu ggcaccaact t                                              21

<210> SEQ ID NO 786
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 786
accugucuuc uaucuggcat t                                              21

```
<210> SEQ ID NO 787
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 787
gagaauccca ggacacuact t                                              21

<210> SEQ ID NO 788
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 788
uuuaacuuaa gaagcuccut t                                              21

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 789
auuucaccac uuaacagggt t                                              21

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 790
uaacucacac aaccuacuut t                                              21

<210> SEQ ID NO 791
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 791
```
uaaaugaauu aacucacact t    21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 792
cccuauuaag aauauuugut t    21

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 793
aguagcccua uuaagaauat t    21

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 794
aaguagcccu auuaagaaut t    21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 795
uuaauucaaa guagcccuat t    21

<210> SEQ ID NO 796
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 796
auuaauucaa aguagcccut t                                              21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 797
gaucaacauu uaucucucat t                                              21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 798
aagaucaaca uuuaucucut t                                              21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 799
uuuagguaac aauaacuuat t                                              21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 800
acuuuaggua acaauaacut t                                              21

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 801
aacuuuaggu aacaauaact t                                                   21

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 802
uaacuuuagg uaacaauaat t                                                   21

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 803
uuaacuuuag guaacaauat t                                                   21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 804
gauuaacuuu agguaacaat t                                                   21

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 805
ggauuaacuu uagguaacat t                                                   21

<210> SEQ ID NO 806
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide
```

-continued

<400> SEQUENCE: 806
cuggauuaac uuuagguaat t                                              21

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 807
ucuggauuaa cuuuagguat t                                              21

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 808
uccucacauu auucagcuat t                                              21

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 809
agaaguuaau ccucacauut t                                              21

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 810
cagaaguuaa uccucacaut t                                              21

<210> SEQ ID NO 811
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 811
aacugauuag gaaaugguct t                                              21

<210> SEQ ID NO 812
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 812
gugaugggcg cgagcgggat t                                              21

<210> SEQ ID NO 813
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 813
cgugaugggc gcgagcgggt t                                              21

<210> SEQ ID NO 814
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 814
uccuccucgc ggucuugcut t                                              21

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 815
auccuccucg cggucuugct t                                              21

<210> SEQ ID NO 816
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 816
gauccuccuc gcggucuugt t                                        21

<210> SEQ ID NO 817
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 817
aagauccucc ucgcggucut t                                        21

<210> SEQ ID NO 818
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 818
ggaagauccu ccucgcggut t                                        21

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 819
cuggaagauc cuccucgcgt t                                        21

<210> SEQ ID NO 820
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 820
ugccagauau caugguacut t                                        21

<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic
      oligonucleotide

<400> SEQUENCE: 821
ucugccagau aucaugguat t                                             21

<210> SEQ ID NO 822
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 822
aucugccaga uaucauggut t                                             21

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 823
caucugccag auaucauggt t                                             21

<210> SEQ ID NO 824
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 824
cuuauacauc ugccagauat t                                             21

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 825
ucuuauacau cugccagaut t                                             21

<210> SEQ ID NO 826
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 826
ccuucuuaua caucugccat t                                              21

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 827
cagggauucc cagugcugat t                                              21

<210> SEQ ID NO 828
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 828
agccagaaca ugggauauat t                                              21

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 829
agcgggcuuc uguaaucugt t                                              21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830
aacagcgggc uucuguaaut t                                              21

<210> SEQ ID NO 831
<211> LENGTH: 21
<212> TYPE: DNA
<213> ORGANISM: Artificial Sequence
```

```
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide

<400> SEQUENCE: 831
aaacagcggg cuucuguaat t                                              21

<210> SEQ ID NO 832
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 832
gaaacagcgg gcuucuguat t                                              21

<210> SEQ ID NO 833
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 833
uagaaacagc gggcuucugt t                                              21

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 834
auagaaacag cgggcuucut t                                              21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 835
ccauagaaac agcgggcuut t                                              21

<210> SEQ ID NO 836
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 836
gcaauuugga agccauagat t                                              21

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 837
ggcaauuugg aagccauagt t                                              21

<210> SEQ ID NO 838
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 838
uuccauggca auuuggaagt t                                              21

<210> SEQ ID NO 839
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 839
aagacuauac auuucagaat t                                              21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 840
aauaagaaga cuauacauut t                                              21

<210> SEQ ID NO 841
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 841
guaaguguca auaagaagat t                                            21

<210> SEQ ID NO 842
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 842
uguaaguguc aauaagaagt t                                            21

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 843
auguaagugu caauaagaat t                                            21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 844
ucguuucaau ggcauugaat t                                            21

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 845
acaaggcauc guuucaaugt t                                            21

<210> SEQ ID NO 846
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 846
ucuucuugac acaaggcaut t                                              21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 847
caauccagcg caaggcccat t                                              21

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 848
ccaauccagc gcaaggccct t                                              21

<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 849
cccaauccag cgcaaggcct t                                              21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 850
ucaccauagg uagccucuut t                                              21
```

```
<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 851
ggcaucaguc cucguuucut t                                              21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 852
aggcaucagu ccucguuuct t                                              21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
ugaggccagg caucagucct t                                              21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 854
gugaggccag gcaucaguct t                                              21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 855
aaugugaggc caggcaucat t                                              21
```

```
<210> SEQ ID NO 856
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 856
guguaaaccc ucaucucugt t                                              21

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 857
cacaguguaa acccucauct t                                              21

<210> SEQ ID NO 858
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 858
guguuugaac aucaggcaat t                                              21

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 859
agguguuuga acaucaggct t                                              21

<210> SEQ ID NO 860
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 860
cagguguuug aacaucaggt t                                              21
```

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
accagguguu ugaacaucat t                                              21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 862
guaccaggug uuugaacaut t                                              21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 863
uguaccaggu guuugaacat t                                              21

<210> SEQ ID NO 864
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 864
uguguaccag guguuugaat t                                              21

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 865
uauccgaaca gcauugauau t                                              21

```
<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 866
```
aggaacuccu guucuaucct t                                              21

```
<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867
```
ugaggaacuc cuguucuaut t                                              21

```
<210> SEQ ID NO 868
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868
```
cagugaggaa cuccuguuct t                                              21

```
<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 869
```
cuucacaggc aaggccucat t                                              21

```
<210> SEQ ID NO 870
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 870
```
uugcuucauu agagugcaat t                                              21

<210> SEQ ID NO 871
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 871
auugcuucau uagagugcat t                                              21

<210> SEQ ID NO 872
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 872
aauguauugc uucauuagat t                                              21

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 873
cucaauguau ugcuucauut t                                              21

<210> SEQ ID NO 874
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 874
ccacaaacuc aauguauugt t                                              21

<210> SEQ ID NO 875
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 875
cugccacaaa cucaauguat t                                                21

<210> SEQ ID NO 876
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 876
gucugccaca aacucaaugt t                                                21

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 877
cauaagucug ucugccacat t                                                21

<210> SEQ ID NO 878
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 878
cagcauaagu cugucugcct t                                                21

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 879
ccaguuccag cauaagucut t                                                21

<210> SEQ ID NO 880
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 880
acccaguucc agcauaagut t                                              21

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 881
aaacccaguu ccagcauaat t                                              21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 882
auggguucuc uacucugaat t                                              21

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 883
uauucuccau aaagucaaat t                                              21

<210> SEQ ID NO 884
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
agaaguuagu cuuccuuct t                                               21

<210> SEQ ID NO 885
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 885
aaagaaguua gucuuuccut t                                              21

<210> SEQ ID NO 886
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
cucaaagaag uuagucuuut t                                              21

<210> SEQ ID NO 887
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 887
acucgccuac ucucuuucut t                                              21

<210> SEQ ID NO 888
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 888
gauacucgcc uacucucuut t                                              21

<210> SEQ ID NO 889
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 889
ucugauacuc gccuacucut t                                              21

<210> SEQ ID NO 890
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<223> OTHER INFORMATION: Description of Combined DNA/RNA Molecule:
      Synthetic oligonucleotide

<400> SEQUENCE: 890
cucugauacu cgccuacuct t                                              21

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 891
uccucugaua cucgccuact t                                              21

<210> SEQ ID NO 892
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 892
auccucugau acucgccuat t                                              21

<210> SEQ ID NO 893
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 893
cauccucuga uacucgccut t                                              21

<210> SEQ ID NO 894
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 894
ccauccucug auacucgcct t                                              21

<210> SEQ ID NO 895
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 895
cccauccucu gauacucgct t                                              21

<210> SEQ ID NO 896
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 896
acuugacauc acucccauct t                                              21

<210> SEQ ID NO 897
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 897
aagucagcau ccaagguaat t                                              21

<210> SEQ ID NO 898
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
cugguuguga gguagcuact t                                              21

<210> SEQ ID NO 899
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 899
acaggacugg uugugaggut t                                              21

<210> SEQ ID NO 900
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 900
auacuaccag cacuauaaat t                                              21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 901
ugguaaguca cagccagcct t                                              21

<210> SEQ ID NO 902
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 902
ugccauuguc acugcuaugt t                                              21

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
agacugccau ugucacugct t                                              21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 904
aagacugcca uugucacugt t                                              21

<210> SEQ ID NO 905
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 905
ccucacuuua aagccaagat t                                              21

<210> SEQ ID NO 906
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 906
cccucacuuu aaagccaagt t                                              21

<210> SEQ ID NO 907
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 907
aagcucacua aagggucact t                                              21

<210> SEQ ID NO 908
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 908
cguugaagca gugaggcugt t                                              21

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 909
ugcguugaag cagugaggct t                                              21

<210> SEQ ID NO 910
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 910
uuuguuugua aagugccagt t                                              21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 911
aguacaaaca auguuuauut t                                              21

<210> SEQ ID NO 912
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 912
gaguacaaac aauguuuaut t                                              21

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 913
ugugaguaca aacaauguut t                                              21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 914
uuggcuccca uuagugguct t                                              21

<210> SEQ ID NO 915
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 915
ggacugacuu uaaaguuggt t                                              21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 916
agagaauccc aggacacuat t                                              21

<210> SEQ ID NO 917
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 917
gauuuaacuu aagaagcuct t                                              21

<210> SEQ ID NO 918
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 918
uugauuucac cacuuaacat t                                              21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 919
aguugauuuc accacuuaat t                                              21

<210> SEQ ID NO 920
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 920
uuaacucaca caaccuacut t                                              21

<210> SEQ ID NO 921
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 921
auuaacucac acaaccuact t                                              21

<210> SEQ ID NO 922
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 922
aaaugaauua acucacacat t                                              21

<210> SEQ ID NO 923
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 923
auaaaugaau uaacucacat t                                              21

<210> SEQ ID NO 924
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 924
uucucccaaa cauaaaggct t                                              21

<210> SEQ ID NO 925
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 925
ugcaaugucu cagcuuucut t                                              21

<210> SEQ ID NO 926
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 926
agaucaacau uuaucucuct t                                              21

<210> SEQ ID NO 927
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 927
auguaucaua uuacagagat t                                              21

<210> SEQ ID NO 928
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 928
uggauuaacu uuagguaact t                                              21

<210> SEQ ID NO 929
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 929
aaucuggauu aacuuuaggt t                                              21
```

```
<210> SEQ ID NO 930
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 930
accugauucc aacuuccgct t                                              21

<210> SEQ ID NO 931
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 931
aaccugauuc caacuuccgt t                                              21

<210> SEQ ID NO 932
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 932
ucacauuauu cagcuaaugt t                                              21

<210> SEQ ID NO 933
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 933
guuaauccuc acauuauuct t                                              21

<210> SEQ ID NO 934
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 934
aaguuaaucc ucacauuaut t                                              21
```

<210> SEQ ID NO 935
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 935
gaaguuaauc cucacauuat t                                              21

<210> SEQ ID NO 936
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 936
ugauuaggaa auggucugat t                                              21

<210> SEQ ID NO 937
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 937
cugauuagga aauggucugt t                                              21

<210> SEQ ID NO 938
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 938
acagcgggcu ucuguaauct t                                              21

<210> SEQ ID NO 939
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 939
auaagaagac uauacauuut t                                              21

<210> SEQ ID NO 940
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 940
auaagucugu cugccacaat t                                            21

<210> SEQ ID NO 941
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 941
guauuuggug uagaaaccat t                                            21

<210> SEQ ID NO 942
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 942
uuacuuuagu cacuuagugt t                                            21

<210> SEQ ID NO 943
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 943
cuacacaagu uuaacuuact t                                            21

<210> SEQ ID NO 944
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 944 uuagcuaca caaguuuaat t								21

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 945
acaugcuuag ucuacacaat t								21

<210> SEQ ID NO 946
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 946
uuaauucaaa guagcccuat t								21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 947
uuaacuuuag guaacaauat t								21

<210> SEQ ID NO 948
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 948
auagaaacag cgggcuucut t								21

<210> SEQ ID NO 949
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 949

-continued guaaguguca auaagaagat t                                           21

<210> SEQ ID NO 950
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 950
acaaggcauc guuucaaugt t                                           21

<210> SEQ ID NO 951
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 951
ucaccauagg uagccucuut t                                           21

<210> SEQ ID NO 952
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 952
guaccaggug uuugaacaut t                                           21

<210> SEQ ID NO 953
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 953
ccacaaacuc aauguauugt t                                           21

<210> SEQ ID NO 954
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 954
ccaguuccag cauaagucut t                                            21

<210> SEQ ID NO 955
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 955
ccauccucug auacucgcct t                                            21

<210> SEQ ID NO 956
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 956
acaggacugg uugugaggut t                                            21

<210> SEQ ID NO 957
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 957
auacuaccag cacuauaaat t                                            21

<210> SEQ ID NO 958
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 958
uuaacucaca caaccuacut t                                            21

<210> SEQ ID NO 959
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 959
auaaaugaau uaacucacat t                                              21

<210> SEQ ID NO 960
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 960
ucacauuauu cagcuaaugt t                                              21

<210> SEQ ID NO 961
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 961
agaaagccag aacaugggat t                                              21

<210> SEQ ID NO 962
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 962
aagaauucuc uguuggacut t                                              21

<210> SEQ ID NO 963
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 963
aagacuauac auuucagaat t                                              21

<210> SEQ ID NO 964
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 964
guaaguguca auaagaagat t                                              21

<210> SEQ ID NO 965
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 965
uguaaguguc aauaagaagt t                                              21

<210> SEQ ID NO 966
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 966
agaaguuagu cuuccuuct t                                               21

<210> SEQ ID NO 967
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 967
aaagaaguua gucuuuccut t                                              21

<210> SEQ ID NO 968
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 968
uccucugaua cucgccuact t                                              21

<210> SEQ ID NO 969
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 969
agaaagccag aacaugggat t                                              21

<210> SEQ ID NO 970
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 970
aagaauucuc uguuggacut t                                              21

<210> SEQ ID NO 971
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 971
aagacuauac auuucagaat t                                              21

<210> SEQ ID NO 972
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 972
guaaguguca auaagaagat t                                              21

<210> SEQ ID NO 973
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 973
uguaaguguc aauaagaagt t                                              21

<210> SEQ ID NO 974
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Description of Combined DNA/RNA Molecule:
      Synthetic oligonucleotide

<400> SEQUENCE: 974
agaaguuagu cuuuccuuct t                                              21

<210> SEQ ID NO 975
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 975
aaagaaguua gucuuuccut t                                              21

<210> SEQ ID NO 976
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 976
uccucugaua cucgccuact t                                              21

<210> SEQ ID NO 977
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 977
agaaagccag aacaugggat t                                              21

<210> SEQ ID NO 978
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 978
aagaauucuc uguuggacut t                                              21

<210> SEQ ID NO 979
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 979
aagacuauac auuucagaat t                                              21

<210> SEQ ID NO 980
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 980
guaaguguca auaagaagat t                                              21

<210> SEQ ID NO 981
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 981
uguaaguguc aauaagaagt t                                              21

<210> SEQ ID NO 982
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 982
agaaguuagu cuuccuuct t                                               21

<210> SEQ ID NO 983
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 983
aaagaaguua gucuuuccut t                                              21

<210> SEQ ID NO 984
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 984
uccucugaua cucgccuact t                                              21

<210> SEQ ID NO 985
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 985
guaaguguca auaagaagat t                                              21

<210> SEQ ID NO 986
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 986
gaatttgcca tgggtggaat tttttctctt ggaaagaaag t                        41

<210> SEQ ID NO 987
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 987
ggagggatct cgctcctgga tttttctctt ggaaagaaag t                        41

<210> SEQ ID NO 988
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 988
ccccagcctt ctccatggtt ttttctcttg gaaagaaagt                          40

<210> SEQ ID NO 989
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 989
gctcccccct gcaaatgagt ttttctcttg gaaagaaagt                          40
```

```
<210> SEQ ID NO 990
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 990
agccttgacg gtgccatgtt tttaggcata ggacccgtgt ct                              42

<210> SEQ ID NO 991
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 991
gatgacaagc ttcccgttct cttttttaggc ataggacccg tgtct                         45

<210> SEQ ID NO 992
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 992
agatggtgat gggatttcca ttttttttagg cataggaccc gtgtct                        46

<210> SEQ ID NO 993
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 993
gcatcgcccc acttgatttt tttttaggca taggacccgt gtct                           44

<210> SEQ ID NO 994
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 994
cacgacgtac tcagcgccat ttttaggcat aggacccgtg tct                            43

<210> SEQ ID NO 995
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 995
ggcagagatg atgacccttt tgtttttagg cataggaccc gtgtct                         46

<210> SEQ ID NO 996
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 996
ggtgaagacg ccagtggact c                                              21

<210> SEQ ID NO 997
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 997
cgggtttcag ggattcccag tttttctctt ggaaagaaag t                        41

<210> SEQ ID NO 998
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 998
gcttgctgca aagaaagcca tttttctctt ggaaagaaag t                        41

<210> SEQ ID NO 999
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 999
cttcttggct aaatcgctcc attttctct tggaaagaaa gt                        42

<210> SEQ ID NO 1000
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1000
agcgggcttc tgtaatctga attttctct tggaaagaaa gt                        42

<210> SEQ ID NO 1001
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1001
gagaaattcc ctttctttgg gattttctc ttggaaagaa agt                       43

<210> SEQ ID NO 1002
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1002
ggtagcctct ttgtccccaa tttttctct tggaaagaaa gt                        42

<210> SEQ ID NO 1003
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1003
gaacatggga tataaaatat ctctcctttt ttaggcatag gacccgtgtc t             51

<210> SEQ ID NO 1004
<211> LENGTH: 49
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1004
ccaagttttc atttactatg ccatctttt aggcatagga cccgtgtct                 49

<210> SEQ ID NO 1005
<211> LENGTH: 49
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1005
catttcagaa tgtatgtttt ccatgttttt aggcatagga cccgtgtct                49

<210> SEQ ID NO 1006
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1006
catcgtttca atggcattga atttttaggc ataggacccg tgtct                    45

<210> SEQ ID NO 1007
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1007
ccagcgcaag gcccagtttt ttaggcatag gacccgtgtc t                        41

<210> SEQ ID NO 1008
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 1008
aaggctacaa cacgttcacc atatttttag gcataggacc cgtgtct            47

<210> SEQ ID NO 1009
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1009
aatgccttcc actgcagcat ttttaggcat aggacccgtg tct                43

<210> SEQ ID NO 1010
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1010
gcaatttgga agccatagaa ac                                       22

<210> SEQ ID NO 1011
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1011
tcttttatgt aagtgtcaat aagaagacta ta                            32

<210> SEQ ID NO 1012
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1012
ctgccttctt cttgacacaa gg                                       22

<210> SEQ ID NO 1013
<211> LENGTH: 3284
<212> TYPE: DNA
<213> ORGANISM: Homo sapiens

<400> SEQUENCE: 1013
cccgtgcacc ctgtcccagc cgtcctgtcc tggctgctcg ctctgcttcg ctgcgcctcc    60
actatgctct ccctccgtgt cccgctcgcg cccatcacgg acccgcagca gctgcagctc   120
tcgccgctga aggggctcag cttggtcgac aaggagaaca cgccgccggc cctgagcggg   180
acccgcgtcc tggccagcaa gaccgcgagg aggatcttcc aggagcccac ggagccgaaa   240
actaaagcag ctgcccccgg cgtggaggat gagccgctgc tgagagaaaa ccccgccgc    300
```

```
tttgtcatct tccccatcga gtaccatgat atctggcaga tgtataagaa ggcagaggct    360
tccttttgga ccgccgagga ggtggacctc tccaaggaca ttcagcactg ggaatccctg    420
aaacccgagg agagatattt tatatcccat gttctggctt tctttgcagc aagcgatggc    480
atagtaaatg aaaacttggt ggagcgattt agccaagaag ttcagattac agaagcccgc    540
tgtttctatg gcttccaaat tgccatggaa acatacatt ctgaaatgta tagtcttctt     600
attgacactt acataaaaga tcccaaagaa agggaatttc tcttcaatgc cattgaaacg    660
atgccttgtg tcaagaagaa ggcagactgg gccttgcgct ggattgggga caaagaggct    720
acctatggtg aacgtgttgt agcctttgct gcagtggaag cattttctt tccggttct     780
tttgcgtcga tattctggct caagaaacga ggactgatgc ctggcctcac attttctaat    840
gaacttatta gcagagatga gggtttacac tgtgattttg cttgcctgat gttcaaacac    900
ctggtacaca aaccatcgga ggagagagta agagaaataa ttatcaatgc tgttcggata    960
gaacaggagt tcctcactga ggccttgcct gtgaagctca ttgggatgaa ttgcactcta   1020
atgaagcaat acattgagtt gtggcagac agacttatgc tggaactggg ttttagcaag    1080
gttttcagag tagagaaccc atttgacttt atggagaata tttcactgga aggaaagact   1140
aacttctttg agaagagagt aggcgagtat cagaggatgg gagtgatgtc aagtccaaca   1200
gagaattctt ttaccttgga tgctgacttc taaatgaact gaagatgtgc ccttacttgg   1260
ctgatttttt ttttccatct cataagaaaa atcagctgaa gtgttaccaa ctagccacac   1320
catgaattgt ccgtaatgtt cattaacagc atctttaaaa ctgtgtagct acctcacaac   1380
cagtcctgtc tgtttatagt gctggtagta tcacctttg ccagaaggcc tggctggctg    1440
tgacttacca tagcagtgac aatggcagtc ttggctttaa agtgagggt gacccttag     1500
tgagcttagc acagcgggat taaacagtcc tttaaccagc acagccagtt aaaagatgca   1560
gcctcactgc ttcaacgcag attttaatgt ttacttaaat ataaacctgg cactttacaa   1620
acaaataaac attgtttgta ctcacaaggc gataatagct tgatttattt ggtttctaca   1680
ccaaatacat tctcctgacc actaatggga gccaattcac aattcactaa gtgactaaag   1740
taagttaaac ttgtgtagac taagcatgta attttttaagt tttatttaa tgaattaaaa    1800
tatttgttaa ccaactttaa agtcagtcct gtgtatacct agatattagt cagttggtgc   1860
cagatagaag acaggttgtg ttttatcct gtggcttgtg tagtgtcctg ggattctctg    1920
cccctctga gtagagtgtt gtgggataaa ggaatctctc agggcaagga gcttcttaag    1980
ttaaatcact agaaatttag gggtgatctg ggccttcata tgtgtgagaa gccgtttcat   2040
tttatttctc actgtatttt cctcaacgtc tggttgatga gaaaaaattc ttgaagagtt   2100
ttcatatgtg ggagctaagg tagtattgta aaatttcaag tcatccttaa acaaaatgat   2160
ccacctaaga tcttgcccct gttaagtggt gaaatcaact agaggtggtt cctacaagtt   2220
gttcattcta gttttgtttg gtgtaagtag gttgtgtgag ttaattcatt tatatttact   2280
atgtctgtta aatcagaaat ttttattat ctatgttctt ctagatttta cctgtagttc    2340
atacttcagt cacccagtgt cttattctgg cattgtctaa atctgagcat tgtctagggg   2400
gatcttaaac tttagtagga aaccatgagc tgttaataca gtttccattc aaatattaat   2460
ttcagaatga aacataattt tttttttttt ttttgagatg gagtctcgct ctgttgccca   2520
ggctggagtg cagtggcgcg attttggctc actgtaacct ccatctcctg ggttcaagca   2580
attctcctgt ctcagcctcc ctagtagctg ggactgcagg tatgtgctac cacacctggc   2640
taatttttgt atttttagta gagatggagt ttcaccatat tggtcaggct ggtcttgaac   2700
```

| | |
|---|---|
| tcctgacctc aggtgatcca cccacctcgg cctcccaaag tgctgggatt gcaggcgtga | 2760 |
| taaacaaata ttcttaatag ggctactttg aattaatctg cctttatgtt tgggagaaga | 2820 |
| aagctgagac attgcatgaa agatgatgag agataaatgt tgatcttttg gccccatttg | 2880 |
| ttaattgtat tcagtatttg aacgtcgtcc tgtttattgt tagttttctt catcatttat | 2940 |
| tgtatagaca atttttaaat ctctgtaata tgatacattt tcctatcttt taagttattg | 3000 |
| ttacctaaag ttaatccaga ttatatggtc cttatatgtg tacaacatta aaatgaaagg | 3060 |
| ctttgtcttg cattgtgagg tacaggcgga agttggaatc aggttttagg attctgtctc | 3120 |
| tcattagctg aataatgtga ggattaactt ctgccagctc agaccatttc ctaatcagtt | 3180 |
| gaaagggaaa caagtatttc agtctcaaaa ttgaataatg cacaagtctt aagtgattaa | 3240 |
| aataaaactg ttcttatgtc agtttcaaaa aaaaaaaaaa aaaa | 3284 |

<210> SEQ ID NO 1014
<211> LENGTH: 3452
<212> TYPE: DNA
<213> ORGANISM: Homo sapiens

<400> SEQUENCE: 1014

| | |
|---|---|
| aaaatcgcgc gcggccccgc ggccagcctg ggtaggggca aggcgcagcc aatgggaagg | 60 |
| gtcggaggca tggcacagcc aatgggaagg gccggggcac caaagccaat gggaagggcc | 120 |
| gggagcgcgc ggcgcgggag atttaaaggc tgctggagtg aggggtcgcc cgtgcaccct | 180 |
| gtcccagccg tcctgtcctg gctgctcgct ctgcttcgct cgcgcctcca tatgctctcc | 240 |
| ctccgtgtcc cgctcgcgcc catcacggac ccgcagcagc tgcagctctc gccgctgaag | 300 |
| gggctcagct tggtcgacaa ggagaacacg ccgccggccc tgagcgggac ccgcgtcctg | 360 |
| gccagcaaga ccgcgaggag gatcttccag gagcccacgg agccgaaaac taaagcagct | 420 |
| gcccccggcg tggaggatga gccgctgctg agagaaaacc cccgccgctt tgtcatcttc | 480 |
| cccatcgagt accatgatat ctggcagatg tataagaagg cagaggcttc cttttggacc | 540 |
| gccgaggagg tggacctctc caaggacatt cagcactggg aatccctgaa acccgaggag | 600 |
| agatatttta tatcccatgt tctggctttc tttgcagcaa gcgatggcat agtaaatgaa | 660 |
| aacttggtgg agcgatttag ccaagaagtt cagattacag aagcccgctg tttctatggc | 720 |
| ttccaaattg ccatgaaaaa catacattct gaaatgtata gtcttcttat tgacacttac | 780 |
| ataaaagatc ccaaagaaag ggaatttctc ttcaatgcca ttgaaacgat gccttgtgtc | 840 |
| aagaagaagg cagactgggc cttgcgctgg attgggggaca aagaggctac ctatggtgaa | 900 |
| cgtgttgtag cctttgctgc agtggaaggc attttctttt ccggttcttt tgcgtcgata | 960 |
| ttctggctca agaaacgagg actgatgcct ggcctcacat tttctaatga acttattagc | 1020 |
| agagatgagg gtttacactg tgattttgct tgcctgatgt tcaaacacct ggtacacaaa | 1080 |
| ccatcggagg agagagtaag agaaataatt atcaatgctg ttcggataga acaggagttc | 1140 |
| ctcactgagg ccttgcctgt gaagctcatt gggatgaatt gcactctaat gaagcaatac | 1200 |
| attgagtttg tggcagacag acttatgctg gaactgggtt ttagcaaggt tttcagagta | 1260 |
| gagaacccat ttgactttat ggagaatatt tcactggaag gaaagactaa cttctttgag | 1320 |
| aagagagtag gcgagtatca gaggatggga gtgatgtcaa gtccaacaga gaattctttt | 1380 |
| accttggatg ctgacttcta aatgaactga agatgtgccc ttacttggct gattttttt | 1440 |
| ttccatctca taagaaaaat cagctgaagt gttaccaact agccacacca tgaattgtcc | 1500 |

-continued

```
gtaatgttca ttaacagcat ctttaaaact gtgtagctac ctcacaacca gtcctgtctg    1560
tttatagtgc tggtagtatc accttttgcc agaaggcctg gctggctgtg acttaccata    1620
gcagtgacaa tggcagtctt ggctttaaag tgaggggtga cccttagtg agcttagcac     1680 agcgggatta acagtcctt taaccagcac agccagttaa aagatgcagc ctcactgctt     1740
caacgcagat tttaatgttt acttaaatat aaacctggca ctttacaaac aaataaacat    1800
tgtttgtact cacaaggcga taatagcttg atttatttgg tttctacacc aaatacattc    1860
tcctgaccac taatgggagc caattcacaa ttcactaagt gactaaagta agttaaactt    1920
gtgtagacta agcatgtaat ttttaagttt tattttaatg aattaaaata tttgttaacc    1980
aactttaaag tcagtcctgt gtatacctag atattagtca gttggtgcca gatagaagac    2040
aggttgtgtt tttatcctgt ggcttgtgta gtgtcctggg attctctgcc ccctctgagt    2100
agagtgttgt gggataaagg aatctctcag ggcaaggagc ttcttaagtt aaatcactag    2160
aaatttaggg gtgatctggg ccttcatatg tgtgagaagc cgtttcattt tatttctcac    2220
tgtattttcc tcaacgtctg gttgatgaga aaaaattctt gaagagtttt catatgtggg    2280
agctaaggta gtattgtaaa atttcaagtc atccttaaac aaaatgatcc acctaagatc    2340
ttgcccctgt taagtggtga aatcaactag aggtggttcc tacaagttgt tcattctagt    2400
tttgtttggt gtaagtaggt tgtgtgagtt aattcattta tatttactat gtctgttaaa    2460
tcagaaattt tttattatct atgttcttct agattttacc tgtagttcat acttcagtca    2520
cccagtgtct tattctggca ttgtctaaat ctgagcattg tctaggggga tcttaaactt    2580
tagtaggaaa ccatgagctg ttaatacagt ttccattcaa atattaattt cagaatgaaa    2640
cataattttt ttttttttt ttgagatgga gtctcgctct gttgcccagg ctggagtgca    2700
gtggcgcgat tttggctcac tgtaacctcc atctcctggg ttcaagcaat tctcctgtct    2760
cagcctccct agtagctggg actgcaggta tgtgctacca cacctggcta atttttgtat    2820
ttttagtaga gatggagttt caccatattg gtcaggctgg tcttgaactc ctgacctcag    2880
gtgatccacc cacctcggcc tcccaaagtg ctgggattgc aggcgtgata aacaaatatt    2940
cttaataggg ctactttgaa ttaatctgcc tttatgtttg ggagaagaaa gctgagacat    3000
tgcatgaaag atgatgagag ataaatgttg atcttttggc cccatttgtt aattgtattc    3060
agtatttgaa cgtcgtcctg tttattgtta gttttcttca tcatttattg tatagacaat    3120
ttttaaatct ctgtaatatg atacattttc ctatctttta agttattgtt acctaaagtt    3180
aatccagatt atatggtcct tatatgtgta caacattaaa atgaaaggct ttgtcttgca    3240
ttgtgaggta caggcggaag ttggaatcag gttttaggat tctgtctctc attagctgaa    3300
taatgtgagg attaacttct gccagctcag accatttcct aatcagttga aagggaaaca    3360
agtatttcag tctcaaaatt gaataatgca caagtcttaa gtgattaaaa taaaactgtt    3420
cttatgtcag tttcaaaaaa aaaaaaaaaa aa                                  3452
```

<210> SEQ ID NO 1015
<211> LENGTH: 3262
<212> TYPE: DNA
<213> ORGANISM: Macaca fascicularis
<220> FEATURE:
<221> NAME/KEY: modified_base
<222> LOCATION: (2354)..(2371)
<223> OTHER INFORMATION: a, c, t, g, unknown or other

<400> SEQUENCE: 1015

```
aaaatcgcgc gctgtcccgc ggccagcctg ggtggggtca aggtgcagcc aatggaaggg      60
```

```
tcggggcac ggcacagcca atgggaaggg ccggggcgcc aaagcgaatg ggaagggccg      120
gcacgggaga tttaaaggct gctggaccga ggggtcgccc gtgcttcgcg tcccagccat     180
cctgttctgg cctgtcgctg tacttcgctg cgccgccact atgctctccg tccgcatccc    240
gctcgcgccc atcacgaacc cgcagcagct gcagctctcg ccgctgaagg ggctaagcct    300
ggtcgacaag gagaacacgc cgccagccct gagcggggcc cgcgtcctgg ccagcaagac    360
cgcgaggagg atcttccagg agcccgcgga gccgaaaact aaagcagctg cccccggcgt    420
ggaggatgaa ccgctgctga gagaaaaccc ccgccgcttt gtcatcttcc ccatcgagta    480
ccatgatatc tggcagatgt ataagaaggc ggaggcttcc ttctggactg ccgaggaggt    540
ggacctgtcc aaggacattc agcactggga atccctgaag cccgaggaga gatattttat    600
atcccatgtt ctggctttct tgcagcaag tgatggcata gtaaatgaaa acttggtgga     660
gcgatttagc caagaagttc agattacaga agcccgctgt ttctatggct tccaaattgc    720
catggaaaac atacattctg aaatgtatag tcttcttatt gacacttaca taaaagatcc    780
caaagaaagg gaatttctct tcaatgccat tgaaacgatg ccttgtgtca agaagaaggc    840
agattgggcc ttgcgctgga ttggggacaa agaggctacc tatggtgaac gtgtcgtagc    900 cttttgccgca gtggaaggca tcttctttc cggttctttt gcatcgatat tctggctcaa    960
gaaacgagga ctgatgcctg gcctcacatt ttccaatgaa cttatcagca gagatgaggg    1020
tttacactgt gattttgctt gcctgatgtt caaacacctg gtacacaaac catcagagga    1080
gagagtaaga gaaataatta tcaatgctgt tcggatagaa caggagttcc tcactgaggc    1140
cttgcctgtg aagctaattg ggatgaattg cactctaatg aagcaataca ttgagtttgt    1200
ggcagacaga cttatgctgg aactgggttt tagcaaggtt ttcagagtag agaacccatt    1260
tgactttatg gagaatattt cactggaagg aaagactaac ttctttgaga agagagtagg    1320
cgagtatcag aggatgggag tgatgtcaag tccaacagag aattctttta ccttggatgc    1380
tgacttctaa atgaactgaa gatatgccct tatttgctg atttttttc ccatgtcata     1440 aagaaaatca gctgaagtgt taccaactag caacaccgtg aattgtccat aatgttcatt    1500
aacagcatct ttaaaactgt gtagctacct cacaaccagt cctgtttatt tatagtgctg    1560
gtagtatcac cttttgccag caggcctggc tggctgtgac ttaccatagc agtgacaatg    1620
gcagtcttgg ctttaaagtg aggggtgacc ctttagtgag cttggcacag caggattaaa    1680
cagtctttta accagcacag ccaattgaaa gaagcagcct cactgcttca acgcacgttt    1740
taatgtttac ttaaatataa aactggcact ttacaaacaa ataaacattg tttgtactca    1800
caaggtaata atagcttgat ttatttggtt tctacaccaa atacaaagca ttctgaccac    1860
taatgggagc caattcacag ttcactaagt gactaaagta agttaaactt gtgtagacta    1920
agcatgtaat ttctaagttt tattttaatg gattgaaata ctcattaacc aactttaaag    1980
tcagtcccgt gtatagctag atattagtct gttggtgcca gatagaagac aggttgtgtt    2040
tttatcctgt ggcttgggta gtgtcctggg attctctgcg ccatctgagt agtgttgtgg    2100
gttaaaggaa tctctcagga caaggagctt cttaagttaa atcattagaa atttaggcat    2160
gatctgggcc ttcatatgtg taagaagcca tttcatctta tttctcactg tattttcctc    2220
aacttctagt tgataaaaaa ttcttgaaga gttttcatat gtgggatcta aggtagtact    2280
gtaaaatttc aagtcatcct taaacaaagt gacccaccta agatcttgcc cctgttaagt    2340
ggtgaaatca actnnnnnnn nnnnnnnnnn nttgttgttt attctagttt tgtttgtaag    2400
```

```
taggttgtgt gagttaattc atttatattt actatgtctt tttttttttt tttttttttt    2460
tgagacggag tctcgctctg ttgcccaggc tagagtgcag tagtgcgatt tcggctcact    2520
gcaacctccg cctcctgggc tcaagcaatt ctcctgtctc agcctcctga gtagctgaaa    2580
ctgcaggtat gtgccaccac acctggctaa tttttgtatt tttagtagag acggagtttc    2640
actatattgg tcaggctggt cttgaactcc tgacctcagg tgatccgccc acctgggcct    2700
cccaaagtgc tgggattaca ggcatgataa acaaatattc ttaatagggc tactttgaat    2760
taatttgcct ttatgtttgg gagaagaaag ctgagacatt gcaagaaaga tgatgagaga    2820
taaatgttga tcttttggcc ccatttgttc attgtattcg ctatttgaac attgtcctgt    2880
tctattgtta gttttcttct tcatttattg tatagtcaat ttttaaatct ctgtaatatg    2940
atacattttc ctatcttaag ttattgttac ctaaagttaa tccagattac attgtcctta    3000
tacttgtaca acattaaaat gaaaggcttt gctttgcatt gtgaggttca ggcggaagtt    3060
ggaatcaggt tttagggttc tgtgtctcat tagctgaata atgtgaggat taacttctgc    3120
caactcagac catttcctaa tcagttgaaa gggaaacaag tatttcaatc tcaaaattga    3180
ataatgcaca agtgttaagt gattaaaata aaactgttct tatgtcagtt tcttgattgg    3240
taaaatttgc attttaattc ag                                            3262
```